US010583174B2

(12) United States Patent
Göbel et al.

(10) Patent No.: US 10,583,174 B2
(45) Date of Patent: Mar. 10, 2020

(54) FGF21 COMPOUND / GLP-1R AGONIST COMBINATIONS WITH OPTIMIZED ACTIVITY RATIO

(71) Applicant: SANOFI, Paris (FR)

(72) Inventors: Britta Göbel, Frankfurt am Main (DE); Mark Sommerfeld, Frankfurt am Main (DE); Oliver Boscheinen, Frankfurt am Main (DE); Thomas Langer, Frankfurt am Main (DE); Christine Rudolph, Frankfurt am Main (DE); Andreas Evers, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/851,963

(22) Filed: Dec. 22, 2017

(65) Prior Publication Data

US 2018/0236037 A1 Aug. 23, 2018

(30) Foreign Application Priority Data

Dec. 22, 2016 (EP) .................................. 16306776

(51) Int. Cl.

| A61K 38/26 | (2006.01) |
| C07K 14/50 | (2006.01) |
| A61K 38/18 | (2006.01) |
| C07K 14/605 | (2006.01) |
| A61K 47/60 | (2017.01) |
| A61P 3/10 | (2006.01) |
| A61K 38/39 | (2006.01) |
| C07K 19/00 | (2006.01) |

(52) U.S. Cl.
CPC .............. *A61K 38/26* (2013.01); *A61K 38/18* (2013.01); *A61K 38/1825* (2013.01); *A61K 38/39* (2013.01); *A61K 47/60* (2017.08); *A61P 3/10* (2018.01); *C07K 14/50* (2013.01); *C07K 14/605* (2013.01); *C07K 19/00* (2013.01); *C07K 2319/00* (2013.01)

(58) Field of Classification Search
CPC ............ A61K 2300/00; A61K 38/1825; A61K 38/00; A61K 38/22; A61K 38/2278; C07K 2319/00; C07K 14/50; C07K 14/575; C07K 14/503; C07K 14/5759; C07K 16/2863; C12N 2320/31
See application file for complete search history.

(56) References Cited

U.S. PATENT DOCUMENTS

| 7,459,540 B1 | 12/2008 | Thomason et al. |
| 2009/0018076 A1 | 1/2009 | Thomason et al. |
| 2010/0226921 A1 | 9/2010 | Thomason et al. |
| 2012/0238496 A1 | 9/2012 | Fan et al. |
| 2013/0203651 A1* | 8/2013 | Sommerfeld ...... A61K 38/1825 514/1.9 |
| 2014/0073563 A1 | 3/2014 | Boscheinen et al. |
| 2015/0166622 A1 | 6/2015 | Boettcher et al. |

FOREIGN PATENT DOCUMENTS

| WO | 2009/149171 A2 | 12/2009 |
| WO | 2010/042747 A2 | 4/2010 |
| WO | 2010/129503 A2 | 11/2010 |
| WO | 2010/129600 A2 | 11/2010 |
| WO | 2011/089203 A1 | 7/2011 |
| WO | 2013/003449 A2 | 1/2013 |
| WO | 2013/188182 A1 | 12/2013 |

OTHER PUBLICATIONS

International Search Report with Written Opinion corresponding to International Patent Application No. PCT/EP2017/084310, dated Mar. 7, 2018.
Brunetti et al. (2008) "Glucagon-like peptide 1 (7-36) amide (GLP-1) and exendin-4 stimulate serotonin release in rat hypothalamus," Peptides. 29(8):1377-1381.
Gaich et al. (Sep. 1, 2013) "The effects of LY2405319, an FGF21 analog, in obese human subjects with type 2 diabetes," Cell Metabol. 18(3):333-340.
International Preliminary Report on Patentability of PCT/EP2016/079551 dated Jun. 14, 2018, 20 pp.

* cited by examiner

*Primary Examiner* — Soren Harward
*Assistant Examiner* — Jia-Hai Lee
(74) *Attorney, Agent, or Firm* — Lathrop GPM LLP; James H. Velema, Esq.

(57) ABSTRACT

The present invention relates to combinations, pharmaceutical compositions and fusion molecules comprising an FGF21 (fibroblast growth factor 21) compound and a GLP-1R (glucagon-like peptide-1 receptor) agonist with optimized GLP-1R agonist/FGF21 compound activity ratio. It further relates to their use as medicaments, in particular for the treatment of obesity, being overweight, metabolic syndrome, diabetes mellitus, diabetic retinopathy, hyperglycemia, dyslipidemia, Non-Alcoholic SteatoHepatitis (NASH) and/or atherosclerosis.

22 Claims, 5 Drawing Sheets
Specification includes a Sequence Listing.

SEQUENCE LISTING

<160> NUMBER OF SEQ ID NOS: 43

<210> SEQ ID NO 1
<211> LENGTH: 209
<212> TYPE: PRT
<213> ORGANISM: Homo sapiens

<400> SEQUENCE: 1

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 2
<211> LENGTH: 181
<212> TYPE: PRT
<213> ORGANISM: Homo sapiens

<400> SEQUENCE: 2

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 3
<211> LENGTH: 181
<212> TYPE: PRT
<213> ORGANISM: Artificial Sequence
<220> FEATURE:
<223> OTHER INFORMATION: FGF21(His29-Ser209) A59C,G71C

<400> SEQUENCE: 3

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 4
<211> LENGTH: 181
<212> TYPE: PRT
<213> ORGANISM: Artificial Sequence
<220> FEATURE:
<223> OTHER INFORMATION: FGF21(His29-Ser209) Q55C,N149C,G198Y

<400> SEQUENCE: 4

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser

```
                 35                  40                  45
Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Cys Lys Ser Pro His Arg Asp Pro
                115                 120                 125

Ala Pro Arg Gly Pro Ala Arg Phe Leu Pro Leu Pro Gly Leu Pro Pro
                130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Tyr Pro Ser Gln Gly Arg Ser
                165                 170                 175

Pro Ser Tyr Ala Ser
                180

<210> SEQ ID NO 5
<211> LENGTH: 180
<212> TYPE: PRT
<213> ORGANISM: Artificial Sequence
<220> FEATURE:
<223> OTHER INFORMATION: FGF21(His29-Ser209) Q55C,P147C,delP199

<400> SEQUENCE: 5

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Cys Gln Thr Glu Ala His
                 20                  25                  30

Leu Glu Ile Arg Glu Asp Gly Thr Val Gly Gly Ala Ala Asp Gln Ser
                 35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Cys Gly Asn Lys Ser Pro His Arg Asp Pro
                115                 120                 125

Ala Pro Arg Gly Pro Ala Arg Phe Leu Pro Leu Pro Gly Leu Pro Pro
                130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser Pro
                165                 170                 175

Ser Tyr Ala Ser
                180

<210> SEQ ID NO 6
<211> LENGTH: 180
<212> TYPE: PRT
```

<213> ORGANISM: Artificial Sequence
<220> FEATURE:
<223> OTHER INFORMATION: FGF21(His29-Ser209) Q55C,N149C,delP199

<400> SEQUENCE: 6

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65              70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Cys Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser Pro
                165                 170                 175

Ser Tyr Ala Ser
            180
```

<210> SEQ ID NO 7
<211> LENGTH: 30
<212> TYPE: PRT
<213> ORGANISM: Homo sapiens

<400> SEQUENCE: 7

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

<210> SEQ ID NO 8
<211> LENGTH: 39
<212> TYPE: PRT
<213> ORGANISM: Artificial Sequence
<220> FEATURE:
<223> OTHER INFORMATION: GLP1(7-36)
    A8G,V16L,S18K,Y19Q,L20M,G22E,Q23E,A25V,K26R,E27L,A30E,V33K,K34N,R
    36G, insPSSGAPPPS

<400> SEQUENCE: 8

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 9

```
<211> LENGTH: 39
<212> TYPE: PRT
<213> ORGANISM: Artificial Sequence
<220> FEATURE:
<223> OTHER INFORMATION: GLP1(7-36)
      A8G,V16L,S18K,Y19Q,G22E,Q23E,A25V,K26Q,E27L,A30E,V33L,K34A,G35T,R
      36G,insPSSGAPPPS

<400> SEQUENCE: 9

His Gly Glu Gly Thr Phe Thr Ser Asp Leu Ser Lys Gln Leu Glu Glu
1               5                   10                  15

Glu Ala Val Gln Leu Phe Ile Glu Trp Leu Leu Ala Thr Gly Pro Ser
            20                  25                  30

Ser Gly Ala Pro Pro Pro Ser
            35

<210> SEQ ID NO 10
<211> LENGTH: 39
<212> TYPE: PRT
<213> ORGANISM: Artificial Sequence
<220> FEATURE:
<223> OTHER INFORMATION: GLP1(7-36)
      A8G,V16L,S18I,Y19Q,E21D,G22E,Q23E,A25V,K26R,E27L,A30E,V33L,K34A,G
      35T,R36G,insPVSGAPPPS

<400> SEQUENCE: 10

His Gly Glu Gly Thr Phe Thr Ser Asp Leu Ser Ile Gln Leu Asp Glu
1               5                   10                  15

Glu Ala Val Arg Leu Phe Ile Glu Trp Leu Leu Ala Thr Gly Pro Val
            20                  25                  30

Ser Gly Ala Pro Pro Pro Ser
            35

<210> SEQ ID NO 11
<211> LENGTH: 39
<212> TYPE: PRT
<213> ORGANISM: Artificial Sequence
<220> FEATURE:
<223> OTHER INFORMATION: GLP1(7-36)
      A8G,V16L,S18I,Y19Q,E21D,G22E,Q23E,A25V,K26R,E27L,A30E,V33E,K34A,G
      35T,R36G,insPVSGAPPPS

<400> SEQUENCE: 11

His Gly Glu Gly Thr Phe Thr Ser Asp Leu Ser Ile Gln Leu Asp Glu
1               5                   10                  15

Glu Ala Val Arg Leu Phe Ile Glu Trp Leu Glu Ala Thr Gly Pro Val
            20                  25                  30

Ser Gly Ala Pro Pro Pro Ser
            35

<210> SEQ ID NO 12
<211> LENGTH: 40
<212> TYPE: PRT
<213> ORGANISM: Artificial Sequence
<220> FEATURE:
<223> OTHER INFORMATION: GLP1(7-36)
      insG,A8G,V16L,S18I,Y19Q,G22E,Q23E,A25V,K26R,E27L,A30E,V33L,K34A,R
      36G,insPSSGAPPPS

<400> SEQUENCE: 12

Gly His Gly Glu Gly Thr Phe Thr Ser Asp Leu Ser Ile Gln Leu Glu
1               5                   10                  15

Glu Glu Ala Val Arg Leu Phe Ile Glu Trp Leu Leu Ala Gly Gly Pro
            20                  25                  30
```

Ser Ser Gly Ala Pro Pro Pro Ser
            35                  40

<210> SEQ ID NO 13
<211> LENGTH: 40
<212> TYPE: PRT
<213> ORGANISM: Artificial Sequence
<220> FEATURE:
<223> OTHER INFORMATION: GLP1(7-36)
      insG,A8G,V16L,S18I,Y19Q,G22E,Q23E,A25V,K26R,E27L,A30E,V33L,K34A,G
      35T,R36G,insPSSGAPPPS

<400> SEQUENCE: 13

Gly His Gly Glu Gly Thr Phe Thr Ser Asp Leu Ser Ile Gln Leu Glu
1               5                   10                  15

Glu Glu Ala Val Arg Leu Phe Ile Glu Trp Leu Leu Ala Thr Gly Pro
            20                  25                  30

Ser Ser Gly Ala Pro Pro Pro Ser
            35                  40

<210> SEQ ID NO 14
<211> LENGTH: 40
<212> TYPE: PRT
<213> ORGANISM: Artificial Sequence
<220> FEATURE:
<223> OTHER INFORMATION: GLP1(7-36)
      A8G,V16L,S18K,Y19Q,E21D,G22E,Q23E,A25V,K26Q,E27L,A30E,V33L,K34A,G
      35T,R36G,insPSSGEPPPES

<400> SEQUENCE: 14

His Gly Glu Gly Thr Phe Thr Ser Asp Leu Ser Lys Gln Leu Glu Glu
1               5                   10                  15

Glu Ala Val Gln Leu Phe Ile Glu Trp Leu Leu Ala Thr Gly Pro Ser
            20                  25                  30

Ser Gly Glu Pro Pro Pro Glu Ser
            35                  40

<210> SEQ ID NO 15
<211> LENGTH: 30
<212> TYPE: PRT
<213> ORGANISM: Artificial Sequence
<220> FEATURE:
<223> OTHER INFORMATION: GLP1(7-36)
      A8G,V16L,S18K,Y19Q,L20M,E21D,G22E,Q23E,A25V,K26R,E27L,A30E,V33K,K
      34N,R36G

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: GLP1(7-36)
      A8G,V16L,S18K,Y19Q,G22E,Q23E,A25V,K26Q,E27L,A30E,V33L,K34A,G35T,R
      36G

<400> SEQUENCE: 16

His Gly Glu Gly Thr Phe Thr Ser Asp Leu Ser Lys Gln Leu Glu Glu
1               5                   10                  15

Glu Ala Val Gln Leu Phe Ile Glu Trp Leu Leu Ala Thr Gly

<210> SEQ ID NO 17
<211> LENGTH: 39
<212> TYPE: PRT
<213> ORGANISM: Artificial Sequence
<220> FEATURE:
<223> OTHER INFORMATION: GLP1(7-36)
A8G,V16L,S18K,Y19Q,G22E,Q23E,A25V,K26Q,E27L,A30E,V33L,K34A,G35T,R
36G,insPSSGEPPPE

<400> SEQUENCE: 17

His Gly Glu Gly Thr Phe Thr Ser Asp Leu Ser Lys Gln Leu Glu Glu
1               5                   10                  15

Glu Ala Val Gln Leu Phe Ile Glu Trp Leu Leu Ala Thr Gly Pro Ser
            20                  25                  30

Ser Gly Glu Pro Pro Glu
        35

<210> SEQ ID NO 18
<211> LENGTH: 40
<212> TYPE: PRT
<213> ORGANISM: Artificial Sequence
<220> FEATURE:
<223> OTHER INFORMATION: GLP1(7-36)
insG,A8G,V16L,S18K,Y19Q,G22E,Q23E,A24R,A25V,K26Q,A30E,insPSSGAPPP
S

<400> SEQUENCE: 18

Gly His Gly Glu Gly Thr Phe Thr Ser Asp Leu Ser Lys Gln Leu Glu
1               5                   10                  15

Glu Glu Arg Val Gln Glu Phe Ile Glu Trp Leu Val Lys Gly Arg Pro
            20                  25                  30

Ser Ser Gly Ala Pro Pro Pro Ser
        35                  40

<210> SEQ ID NO 19
<211> LENGTH: 39
<212> TYPE: PRT
<213> ORGANISM: Artificial Sequence
<220> FEATURE:
<223> OTHER INFORMATION: GLP1(7-36)
A8G,V16L,S18K,Y19Q,G22E,Q23E,A25V,K26Q,E27L,A30E,V33E,K34A,G35T,R
36G,insPSSGAPPPS

<400> SEQUENCE: 19

His Gly Glu Gly Thr Phe Thr Ser Asp Leu Ser Lys Gln Leu Glu Glu
1               5                   10                  15

Glu Ala Val Gln Leu Phe Ile Glu Trp Leu Glu Ala Thr Gly Pro Ser
            20                  25                  30

Ser Gly Ala Pro Pro Ser
        35

<210> SEQ ID NO 20
<211> LENGTH: 38
<212> TYPE: PRT
<213> ORGANISM: Artificial Sequence
<220> FEATURE:
<223> OTHER INFORMATION: GLP1(7-36)
insG,A8G,V16L,S18I,Y19Q,G22E,Q23E,A25V,K26R,E27L,A30E,V33L,K34A,R
36G,insPKKQRLS

<400> SEQUENCE: 20

Gly His Gly Glu Gly Thr Phe Thr Ser Asp Leu Ser Ile Gln Leu Glu
1               5                   10                  15

```
Glu Glu Ala Val Arg Leu Phe Ile Glu Trp Leu Leu Ala Gly Gly Pro
                20                  25                  30

Lys Lys Gln Arg Leu Ser
        35
```

<210> SEQ ID NO 21
<211> LENGTH: 228
<212> TYPE: PRT
<213> ORGANISM: Artificial Sequence
<220> FEATURE:
<223> OTHER INFORMATION: IgG4 Fc variant, IGHG4_HUMAN (Glu99-Gly326)

<400> SEQUENCE: 21

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225
```

<210> SEQ ID NO 22
<211> LENGTH: 19
<212> TYPE: PRT
<213> ORGANISM: Artificial Sequence
<220> FEATURE:
<223> OTHER INFORMATION: (G7S)(G4S)(G4S)A Linker (19GS)

<400> SEQUENCE: 22

```
Gly Gly Gly Gly Gly Gly Gly Ser Gly Gly Gly Gly Ser Gly Gly Gly
1               5                   10                  15

Gly Ser Ala
```

<210> SEQ ID NO 23

-continued

```
<211> LENGTH: 7
<212> TYPE: PRT
<213> ORGANISM: Artificial Sequence
<220> FEATURE:
<223> OTHER INFORMATION: (G3S)(GS)A Linker (7GS)

<400> SEQUENCE: 23

Gly Gly Gly Ser Gly Ser Ala
1               5

<210> SEQ ID NO 24
<211> LENGTH: 474
<212> TYPE: PRT
<213> ORGANISM: Artificial Sequence
<220> FEATURE:
<223> OTHER INFORMATION: GLP1(7-36)
      A8G,V16L,S18K,Y19Q,L20M,G22E,Q23E,A25V,K26R,E27L,A30E,V33K,K34N,R
      36G, insPSSGAPPPS_[19GS]_IgG4 Fc_variant [7GS]_
      FGF21(His29-Ser209)_A59C,G71C

<400> SEQUENCE: 24

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser Gly Gly Gly Gly Gly Gly Ser Gly
            35                  40                  45

Gly Gly Gly Ser Gly Gly Gly Ser Ala Glu Ser Lys Tyr Gly Pro
        50                  55                  60

Pro Cys Pro Pro Cys Pro Ala Pro Glu Phe Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser Gln Glu Asp Pro Glu
            100                 105                 110

Val Gln Phe Asn Trp Tyr Val Asp Gly Val Glu Val His Asn Ala Lys
        115                 120                 125

Thr Lys Pro Arg Glu Glu Gln Phe Asn Ser Thr Tyr Arg Val Val Ser
130                 135                 140

Val Leu Thr Val Leu His Gln Asp Trp Leu Asn Gly Lys Glu Tyr Lys
145                 150                 155                 160

Cys Lys Val Ser Asn Lys Gly Leu Pro Ser Ser Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Gln Glu Glu Met Thr Lys Asn Gln Val Ser Leu Thr Cys Leu
        195                 200                 205

Val Lys Gly Phe Tyr Pro Ser Asp Ile Ala Val Glu Trp Glu Ser Asn
210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Arg Leu Thr Val Asp Lys Ser Arg
                245                 250                 255

Trp Gln Glu Gly Asn Val Phe Ser Cys Ser Val Met His Glu Ala Leu
            260                 265                 270

His Asn His Tyr Thr Gln Lys Ser Leu Ser Leu Ser Leu Gly Gly Gly
        275                 280                 285

Gly Ser Gly Ser Ala His Pro Ile Pro Asp Ser Ser Pro Leu Leu Gln
```

```
                290             295             300
Phe Gly Gly Gln Val Arg Gln Arg Tyr Leu Tyr Thr Asp Asp Ala Gln
305                     310                 315                 320

Gln Thr Glu Cys His Leu Glu Ile Arg Glu Asp Gly Thr Val Gly Cys
                325                 330                 335

Ala Ala Asp Gln Ser Pro Glu Ser Leu Leu Gln Leu Lys Ala Leu Lys
                340                 345                 350

Pro Gly Val Ile Gln Ile Leu Gly Val Lys Thr Ser Arg Phe Leu Cys
                355                 360                 365

Gln Arg Pro Asp Gly Ala Leu Tyr Gly Ser Leu His Phe Asp Pro Glu
                370                 375                 380

Ala Cys Ser Phe Arg Glu Leu Leu Leu Glu Asp Gly Tyr Asn Val Tyr
385                 390                 395                 400

Gln Ser Glu Ala His Gly Leu Pro Leu His Leu Pro Gly Asn Lys Ser
                405                 410                 415

Pro His Arg Asp Pro Ala Pro Arg Gly Pro Ala Arg Phe Leu Pro Leu
                420                 425                 430

Pro Gly Leu Pro Pro Ala Pro Pro Glu Pro Pro Gly Ile Leu Ala Pro
                435                 440                 445

Gln Pro Pro Asp Val Gly Ser Ser Asp Pro Leu Ser Met Val Gly Pro
                450                 455                 460

Ser Gln Gly Arg Ser Pro Ser Tyr Ala Ser
465                 470

<210> SEQ ID NO 25
<211> LENGTH: 474
<212> TYPE: PRT
<213> ORGANISM: Artificial Sequence
<220> FEATURE:
<223> OTHER INFORMATION: GLP1(7-36)
      A8G,V16L,S18K,Y19Q,G22E,Q23E,A25V,K26Q,E27L,A30E,V33L,K34A,G35T,R
      36G,insPSSGAPPPS_[19GS]_IgG4 Fc
      variant_[7GS]_FGF21(His29-Ser209)Q55C,N149C,G198Y

<400> SEQUENCE: 25

His Gly Glu Gly Thr Phe Thr Ser Asp Leu Ser Lys Gln Leu Glu Glu
1                   5                   10                  15

Glu Ala Val Gln Leu Phe Ile Glu Trp Leu Leu Ala Thr Gly Pro Ser
                20                  25                  30

Ser Gly Ala Pro Pro Ser Gly Gly Gly Gly Gly Ser Gly
                35                  40                  45

Gly Gly Ser Gly Gly Gly Ser Ala Glu Ser Lys Tyr Gly Pro
50                  55                  60

Pro Cys Pro Pro Cys Pro Ala Pro Glu Phe Glu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser Gln Glu Asp Pro Glu
                100                 105                 110

Val Gln Phe Asn Trp Tyr Val Asp Gly Val Glu Val His Asn Ala Lys
                115                 120                 125

Thr Lys Pro Arg Glu Glu Gln Phe Asn Ser Thr Tyr Arg Val Val Ser
                130                 135                 140

Val Leu Thr Val Leu His Gln Asp Trp Leu Asn Gly Lys Glu Tyr Lys
145                 150                 155                 160

Cys Lys Val Ser Asn Lys Gly Leu Pro Ser Ser Ile Glu Lys Thr Ile
```

165                 170                 175
Ser Lys Ala Lys Gly Gln Pro Arg Glu Pro Gln Val Tyr Thr Leu Pro
            180                 185                 190

Pro Ser Gln Glu Glu Met Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Arg Leu Thr Val Asp Lys Ser Arg
                245                 250                 255

Trp Gln Glu Gly Asn Val Phe Ser Cys Ser Val Met His Glu Ala Leu
            260                 265                 270

His Asn His Tyr Thr Gln Lys Ser Leu Ser Leu Ser Leu Gly Gly Gly
        275                 280                 285

Gly Ser Gly Ser Ala His Pro Ile Pro Asp Ser Ser Pro Leu Leu Gln
    290                 295                 300

Phe Gly Gly Gln Val Arg Gln Arg Tyr Leu Tyr Thr Asp Asp Ala Cys
305                 310                 315                 320

Gln Thr Glu Ala His Leu Glu Ile Arg Glu Asp Gly Thr Val Gly Gly
                325                 330                 335

Ala Ala Asp Gln Ser Pro Glu Ser Leu Leu Gln Leu Lys Ala Leu Lys
            340                 345                 350

Pro Gly Val Ile Gln Ile Leu Gly Val Lys Thr Ser Arg Phe Leu Cys
        355                 360                 365

Gln Arg Pro Asp Gly Ala Leu Tyr Gly Ser Leu His Phe Asp Pro Glu
    370                 375                 380

Ala Cys Ser Phe Arg Glu Leu Leu Leu Glu Asp Gly Tyr Asn Val Tyr
385                 390                 395                 400

Gln Ser Glu Ala His Gly Leu Pro Leu His Leu Pro Gly Cys Lys Ser
                405                 410                 415

Pro His Arg Asp Pro Ala Pro Arg Gly Pro Ala Arg Phe Leu Pro Leu
            420                 425                 430

Pro Gly Leu Pro Pro Ala Pro Pro Glu Pro Pro Gly Ile Leu Ala Pro
        435                 440                 445

Gln Pro Pro Asp Val Gly Ser Ser Asp Pro Leu Ser Met Val Tyr Pro
    450                 455                 460

Ser Gln Gly Arg Ser Pro Ser Tyr Ala Ser
465                 470

<210> SEQ ID NO 26
<211> LENGTH: 473
<212> TYPE: PRT
<213> ORGANISM: Artificial Sequence
<220> FEATURE:
<223> OTHER INFORMATION: GLP1(7-36)
      A8G,V16L,S18I,Y19Q,E21D,G22E,Q23E,A25V,K26R,E27L,A30E,V33L,K34A,G
      35T,R36G,insPVSGAPPPS_[19GS]_IgG4 Fc_variant
      [7GS]_FGF21(His29-Ser209)Q55C,P147C,delP199

<400> SEQUENCE: 26

His Gly Glu Gly Thr Phe Thr Ser Asp Leu Ser Ile Gln Leu Asp Glu
1               5                   10                  15

Glu Ala Val Arg Leu Phe Ile Glu Trp Leu Leu Ala Thr Gly Pro Val
            20                  25                  30

Ser Gly Ala Pro Pro Pro Ser Gly Gly Gly Gly Gly Gly Gly Ser Gly

-continued

```
            35                  40                  45
Gly Gly Gly Ser Gly Gly Gly Ser Ala Glu Ser Lys Tyr Gly Pro
        50                  55                  60
Pro Cys Pro Pro Cys Pro Ala Pro Glu Phe Glu Gly Gly Pro Ser Val
65                      70                  75                  80
Phe Leu Phe Pro Pro Lys Pro Lys Asp Thr Leu Met Ile Ser Arg Thr
                    85                  90                  95
Pro Glu Val Thr Cys Val Val Val Asp Val Ser Gln Glu Asp Pro Glu
                100                 105                 110
Val Gln Phe Asn Trp Tyr Val Asp Gly Val Glu Val His Asn Ala Lys
            115                 120                 125
Thr Lys Pro Arg Glu Glu Gln Phe Asn Ser Thr Tyr Arg Val Val Ser
        130                 135                 140
Val Leu Thr Val Leu His Gln Asp Trp Leu Asn Gly Lys Glu Tyr Lys
145                 150                 155                 160
Cys Lys Val Ser Asn Lys Gly Leu Pro Ser Ser Ile Glu Lys Thr Ile
                165                 170                 175
Ser Lys Ala Lys Gly Gln Pro Arg Glu Pro Gln Val Tyr Thr Leu Pro
            180                 185                 190
Pro Ser Gln Glu Glu Met Thr Lys Asn Gln Val Ser Leu Thr Cys Leu
        195                 200                 205
Val Lys Gly Phe Tyr Pro Ser Asp Ile Ala Val Glu Trp Glu Ser Asn
210                 215                 220
Gly Gln Pro Glu Asn Asn Tyr Lys Thr Thr Pro Pro Val Leu Asp Ser
225                 230                 235                 240
Asp Gly Ser Phe Phe Leu Tyr Ser Arg Leu Thr Val Asp Lys Ser Arg
                245                 250                 255
Trp Gln Glu Gly Asn Val Phe Ser Cys Ser Val Met His Glu Ala Leu
            260                 265                 270
His Asn His Tyr Thr Gln Lys Ser Leu Ser Leu Ser Leu Gly Gly Gly
        275                 280                 285
Gly Ser Gly Ser Ala His Pro Ile Pro Asp Ser Ser Pro Leu Leu Gln
290                 295                 300
Phe Gly Gly Gln Val Arg Gln Arg Tyr Leu Tyr Thr Asp Asp Ala Cys
305                 310                 315                 320
Gln Thr Glu Ala His Leu Glu Ile Arg Glu Asp Gly Thr Val Gly Gly
                325                 330                 335
Ala Ala Asp Gln Ser Pro Glu Ser Leu Leu Gln Leu Lys Ala Leu Lys
            340                 345                 350
Pro Gly Val Ile Gln Ile Leu Gly Val Lys Thr Ser Arg Phe Leu Cys
        355                 360                 365
Gln Arg Pro Asp Gly Ala Leu Tyr Gly Ser Leu His Phe Asp Pro Glu
    370                 375                 380
Ala Cys Ser Phe Arg Glu Leu Leu Leu Glu Asp Gly Tyr Asn Val Tyr
385                 390                 395                 400
Gln Ser Glu Ala His Gly Leu Pro Leu His Leu Cys Gly Asn Lys Ser
                405                 410                 415
Pro His Arg Asp Pro Ala Pro Arg Gly Pro Ala Arg Phe Leu Pro Leu
            420                 425                 430
Pro Gly Leu Pro Pro Ala Pro Pro Glu Pro Gly Ile Leu Ala Pro
        435                 440                 445
Gln Pro Pro Asp Val Gly Ser Ser Asp Pro Leu Ser Met Val Gly Ser
        450                 455                 460
```

Gln Gly Arg Ser Pro Ser Tyr Ala Ser
465                 470

<210> SEQ ID NO 27
<211> LENGTH: 473
<212> TYPE: PRT
<213> ORGANISM: Artificial Sequence
<220> FEATURE:
<223> OTHER INFORMATION: GLP1(7-36)
    A8G,V16L,S18I,Y19Q,E21D,G22E,Q23E,A25V,K26R,E27L,A30E,V33E,K34A,G
    35T,R36G,insPVSGAPPPS_[19GS]_IgG4 Fc_variant
    [7GS]_FGF21(His29-Ser209)Q55C,N149C,delP199

<400> SEQUENCE: 27

His Gly Glu Gly Thr Phe Thr Ser Asp Leu Ser Ile Gln Leu Asp Glu
1               5                   10                  15

Glu Ala Val Arg Leu Phe Ile Glu Trp Leu Ala Thr Gly Pro Val
            20                  25                  30

Ser Gly Ala Pro Pro Pro Ser Gly Gly Gly Gly Gly Gly Ser Gly
            35                  40                      45

Gly Gly Gly Ser Gly Gly Gly Ser Ala Glu Ser Lys Tyr Gly Pro
    50                  55                  60

Pro Cys Pro Pro Cys Pro Ala Pro Glu Phe Glu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser Gln Glu Asp Pro Glu
            100                 105                 110

Val Gln Phe Asn Trp Tyr Val Asp Gly Val Glu Val His Asn Ala Lys
        115                 120                 125

Thr Lys Pro Arg Glu Glu Gln Phe Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Gly Leu Pro Ser Ser Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Gln Glu Glu Met Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Arg Leu Thr Val Asp Lys Ser Arg
                245                 250                 255

Trp Gln Glu Gly Asn Val Phe Ser Cys Ser Val Met His Glu Ala Leu
            260                 265                 270

His Asn His Tyr Thr Gln Lys Ser Leu Ser Leu Ser Leu Gly Gly Gly
        275                 280                 285

Gly Ser Gly Ser Ala His Pro Ile Pro Asp Ser Ser Pro Leu Leu Gln
    290                 295                 300

Phe Gly Gly Gln Val Arg Gln Arg Tyr Leu Tyr Thr Asp Asp Ala Cys
305                 310                 315                 320

Gln Thr Glu Ala His Leu Glu Ile Arg Glu Asp Gly Thr Val Gly Gly
                325                 330                 335

Ala Ala Asp Gln Ser Pro Glu Ser Leu Leu Gln Leu Lys Ala Leu Lys
                340                 345                 350

Pro Gly Val Ile Gln Ile Leu Gly Val Lys Thr Ser Arg Phe Leu Cys
            355                 360                 365

Gln Arg Pro Asp Gly Ala Leu Tyr Gly Ser Leu His Phe Asp Pro Glu
        370                 375                 380

Ala Cys Ser Phe Arg Glu Leu Leu Glu Asp Gly Tyr Asn Val Tyr
385                 390                 395                 400

Gln Ser Glu Ala His Gly Leu Pro Leu His Leu Pro Gly Cys Lys Ser
                405                 410                 415

Pro His Arg Asp Pro Ala Pro Arg Gly Pro Ala Arg Phe Leu Pro Leu
            420                 425                 430

Pro Gly Leu Pro Pro Ala Pro Pro Glu Pro Gly Ile Leu Ala Pro
        435                 440                 445

Gln Pro Pro Asp Val Gly Ser Ser Asp Pro Leu Ser Met Val Gly Ser
    450                 455                 460

Gln Gly Arg Ser Pro Ser Tyr Ala Ser
465                 470

<210> SEQ ID NO 28
<211> LENGTH: 474
<212> TYPE: PRT
<213> ORGANISM: Artificial Sequence
<220> FEATURE:
<223> OTHER INFORMATION: GLP1(7-36)
      insG,A8G,V16L,S18I,Y19Q,G22E,Q23E,A25V,K26R,E27L,A30E,V33L,K34A,R
      36G,insPSSGAPPPS_[19GS]_IgG4 Fc_variant
      [7GS]_FGF21(His29-Ser209)Q55C,N149C,delP199

<400> SEQUENCE: 28

Gly His Gly Glu Gly Thr Phe Thr Ser Asp Leu Ser Ile Gln Leu Glu
1               5                   10                  15

Glu Glu Ala Val Arg Leu Phe Ile Glu Trp Leu Leu Ala Gly Gly Pro
                20                  25                  30

Ser Ser Gly Ala Pro Pro Pro Ser Gly Gly Gly Gly Gly Gly Gly Ser
            35                  40                  45

Gly Gly Gly Gly Ser Gly Gly Gly Ser Ala Glu Ser Lys Tyr Gly
        50                  55                  60

Pro Pro Cys Pro Pro Cys Pro Ala Pro Glu Phe Glu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser Gln Glu Asp Pro
            100                 105                 110

Glu Val Gln Phe Asn Trp Tyr Val Asp Gly Val Glu Val His Asn Ala
        115                 120                 125

Lys Thr Lys Pro Arg Glu Glu Gln Phe Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Gly Leu Pro Ser Ser Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Gln Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
            210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Arg Leu Thr Val Asp Lys Ser
                245                 250                 255

Arg Trp Gln Glu Gly Asn Val Phe Ser Cys Ser Val Met His Glu Ala
                260                 265                 270

Leu His Asn His Tyr Thr Gln Lys Ser Leu Ser Leu Ser Leu Gly Gly
            275                 280                 285

Gly Gly Ser Gly Ser Ala His Pro Ile Pro Asp Ser Ser Pro Leu Leu
            290                 295                 300

Gln Phe Gly Gly Gln Val Arg Gln Arg Tyr Leu Tyr Thr Asp Asp Ala
305                 310                 315                 320

Cys Gln Thr Glu Ala His Leu Glu Ile Arg Glu Asp Gly Thr Val Gly
                325                 330                 335

Gly Ala Ala Asp Gln Ser Pro Glu Ser Leu Leu Gln Leu Lys Ala Leu
                340                 345                 350

Lys Pro Gly Val Ile Gln Ile Leu Gly Val Lys Thr Ser Arg Phe Leu
            355                 360                 365

Cys Gln Arg Pro Asp Gly Ala Leu Tyr Gly Ser Leu His Phe Asp Pro
370                 375                 380

Glu Ala Cys Ser Phe Arg Glu Leu Leu Leu Glu Asp Gly Tyr Asn Val
385                 390                 395                 400

Tyr Gln Ser Glu Ala His Gly Leu Pro Leu His Leu Pro Gly Cys Lys
                405                 410                 415

Ser Pro His Arg Asp Pro Ala Pro Arg Gly Pro Ala Arg Phe Leu Pro
            420                 425                 430

Leu Pro Gly Leu Pro Pro Ala Pro Pro Glu Pro Pro Gly Ile Leu Ala
            435                 440                 445

Pro Gln Pro Pro Asp Val Gly Ser Ser Asp Pro Leu Ser Met Val Gly
450                 455                 460

Ser Gln Gly Arg Ser Pro Ser Tyr Ala Ser
465                 470

<210> SEQ ID NO 29
<211> LENGTH: 474
<212> TYPE: PRT
<213> ORGANISM: Artificial Sequence
<220> FEATURE:
<223> OTHER INFORMATION: GLP1(7-36)
      insG,A8G,V16L,S18I,Y19Q,G22E,Q23E,A25V,K26R,E27L,A30E,V33L,K34A,G
      35T,R36G,insPSSGAPPPS_[19GS]_Ig4G Fc_variant
      [7GS]_FGF21(His29-Ser209)Q55C,P147C,delP199

<400> SEQUENCE: 29

Gly His Gly Glu Gly Thr Phe Thr Ser Asp Leu Ser Ile Gln Leu Glu
1               5                   10                  15

Glu Glu Ala Val Arg Leu Phe Ile Glu Trp Leu Leu Ala Thr Gly Pro
            20                  25                  30

Ser Ser Gly Ala Pro Pro Ser Gly Gly Gly Gly Gly Gly Gly Gly Ser
            35                  40                  45

Gly Gly Gly Gly Ser Gly Gly Gly Ser Ala Glu Ser Lys Tyr Gly
            50                  55                  60

Pro Pro Cys Pro Pro Cys Pro Ala Pro Glu Phe Glu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Asp Val Ser Gln Glu Asp Pro
            100                 105                 110

Glu Val Gln Phe Asn Trp Tyr Val Asp Gly Val Glu Val His Asn Ala
            115                 120                 125

Lys Thr Lys Pro Arg Glu Glu Gln Phe Asn Ser Thr Tyr Arg Val Val
            130                 135                 140

Ser Val Leu Thr Val Leu His Gln Asp Trp Leu Asn Gly Lys Glu Tyr
145                 150                 155                 160

Lys Cys Lys Val Ser Asn Lys Gly Leu Pro Ser Ser Ile Glu Lys Thr
                165                 170                 175

Ile Ser Lys Ala Lys Gly Gln Pro Arg Glu Pro Gln Val Tyr Thr Leu
                180                 185                 190

Pro Pro Ser Gln Glu Glu Met Thr Lys Asn Gln Val Ser Leu Thr Cys
            195                 200                 205

Leu Val Lys Gly Phe Tyr Pro Ser Asp Ile Ala Val Glu Trp Glu Ser
            210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Arg Leu Thr Val Asp Lys Ser
                245                 250                 255

Arg Trp Gln Glu Gly Asn Val Phe Ser Cys Ser Val Met His Glu Ala
                260                 265                 270

Leu His Asn His Tyr Thr Gln Lys Ser Leu Ser Leu Ser Leu Gly Gly
                275                 280                 285

Gly Gly Ser Gly Ser Ala His Pro Ile Pro Asp Ser Ser Pro Leu Leu
            290                 295                 300

Gln Phe Gly Gly Gln Val Arg Gln Arg Tyr Leu Tyr Thr Asp Asp Ala
305                 310                 315                 320

Cys Gln Thr Glu Ala His Leu Glu Ile Arg Glu Asp Gly Thr Val Gly
                325                 330                 335

Gly Ala Ala Asp Gln Ser Pro Glu Ser Leu Leu Gln Leu Lys Ala Leu
            340                 345                 350

Lys Pro Gly Val Ile Gln Ile Leu Gly Val Lys Thr Ser Arg Phe Leu
            355                 360                 365

Cys Gln Arg Pro Asp Gly Ala Leu Tyr Gly Ser Leu His Phe Asp Pro
            370                 375                 380

Glu Ala Cys Ser Phe Arg Glu Leu Leu Leu Glu Asp Gly Tyr Asn Val
385                 390                 395                 400

Tyr Gln Ser Glu Ala His Gly Leu Pro Leu His Leu Cys Gly Asn Lys
                405                 410                 415

Ser Pro His Arg Asp Pro Ala Pro Arg Gly Pro Ala Arg Phe Leu Pro
            420                 425                 430

Leu Pro Gly Leu Pro Pro Ala Pro Glu Pro Gly Ile Leu Ala
            435                 440                 445

Pro Gln Pro Pro Asp Val Gly Ser Ser Asp Pro Leu Ser Met Val Gly
450                 455                 460

Ser Gln Gly Arg Ser Pro Ser Tyr Ala Ser
465                 470

<210> SEQ ID NO 30
<211> LENGTH: 475

```
<212> TYPE: PRT
<213> ORGANISM: Artificial Sequence
<220> FEATURE:
<223> OTHER INFORMATION: GLP1(7-36)
      A8G,V16L,S18K,Y19Q,E21D,G22E,Q23E,A25V,K26Q,E27L,A30E,V33L,K34A,G
      35T,R36G,insPSSGEPPPES_[19GS]_IgG4 Fc_variant
      [7GS]_FGF21(His29-Ser209)Q55C,N149C,G198Y

<400> SEQUENCE: 30
```

| His | Gly | Glu | Gly | Thr | Phe | Thr | Ser | Asp | Leu | Ser | Lys | Gln | Leu | Glu | Glu |
|---|---|---|---|---|---|---|---|---|---|---|---|---|---|---|---|
| 1 | | | | 5 | | | | | 10 | | | | | 15 | |

Glu Ala Val Gln Leu Phe Ile Glu Trp Leu Leu Ala Thr Gly Pro Ser
            20                  25                  30

Ser Gly Glu Pro Pro Glu Ser Gly Gly Gly Gly Gly Gly Ser
        35                  40                  45

Gly Gly Gly Gly Ser Gly Gly Gly Ser Ala Glu Ser Lys Tyr Gly
    50                  55                  60

Pro Pro Cys Pro Pro Cys Pro Ala Pro Glu Phe Glu Gly Gly Pro Ser
65              70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser Gln Glu Asp Pro
            100                 105                 110

Glu Val Gln Phe Asn Trp Tyr Val Asp Gly Val Glu Val His Asn Ala
            115                 120                 125

Lys Thr Lys Pro Arg Glu Glu Gln Phe Asn Ser Thr Tyr Arg Val Val
130                 135                 140

Ser Val Leu Thr Val Leu His Gln Asp Trp Leu Asn Gly Lys Glu Tyr
145                 150                 155                 160

Lys Cys Lys Val Ser Asn Lys Gly Leu Pro Ser Ser Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Gln Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Arg Leu Thr Val Asp Lys Ser
                245                 250                 255

Arg Trp Gln Glu Gly Asn Val Phe Ser Cys Ser Val Met His Glu Ala
            260                 265                 270

Leu His Asn His Tyr Thr Gln Lys Ser Leu Ser Leu Ser Leu Gly Gly
        275                 280                 285

Gly Gly Ser Gly Ser Ala His Pro Ile Pro Asp Ser Ser Pro Leu Leu
    290                 295                 300

Gln Phe Gly Gly Gln Val Arg Gln Arg Tyr Leu Tyr Thr Asp Asp Ala
305                 310                 315                 320

Cys Gln Thr Glu Ala His Leu Glu Ile Arg Glu Asp Gly Thr Val Gly
                325                 330                 335

Gly Ala Ala Asp Gln Ser Pro Glu Ser Leu Leu Gln Leu Lys Ala Leu
            340                 345                 350

Lys Pro Gly Val Ile Gln Ile Leu Gly Val Lys Thr Ser Arg Phe Leu
        355                 360                 365

```
Cys Gln Arg Pro Asp Gly Ala Leu Tyr Gly Ser Leu His Phe Asp Pro
    370                 375                 380

Glu Ala Cys Ser Phe Arg Glu Leu Leu Leu Glu Asp Gly Tyr Asn Val
385                 390                 395                 400

Tyr Gln Ser Glu Ala His Gly Leu Pro Leu His Leu Pro Gly Cys Lys
                405                 410                 415

Ser Pro His Arg Asp Pro Ala Pro Arg Gly Pro Ala Arg Phe Leu Pro
                420                 425                 430

Leu Pro Gly Leu Pro Pro Ala Pro Glu Pro Pro Gly Ile Leu Ala
            435                 440                 445

Pro Gln Pro Pro Asp Val Gly Ser Ser Asp Pro Leu Ser Met Val Tyr
450                 455                 460

Pro Ser Gln Gly Arg Ser Pro Ser Tyr Ala Ser
465                 470                 475

<210> SEQ ID NO 31
<211> LENGTH: 465
<212> TYPE: PRT
<213> ORGANISM: Artificial Sequence
<220> FEATURE:
<223> OTHER INFORMATION: GLP1(7-36)
      A8G,V16L,S18K,Y19Q,L20M,E21D,G22E,Q23E,A25V,K26R,E27L,A30E,V33K,K
      34N,R36G_[19GS]_IgG4 Fc_variant
      [7GS]_FGF21(His29-Ser209)Q55C,N149C,G198Y

<400> SEQUENCE: 31

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
                20                  25                  30

Gly Gly Gly Gly Gly Ser Gly Gly Gly Gly Ser Gly Gly Gly Gly Ser
            35                  40                  45

Ala Glu Ser Lys Tyr Gly Pro Pro Cys Pro Pro Cys Pro Ala Pro Glu
    50                  55                  60

Phe Glu Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser Gln Glu Asp Pro Glu Val Gln Phe Asn Trp Tyr Val Asp Gly
            100                 105                 110

Val Glu Val His Asn Ala Lys Thr Lys Pro Arg Glu Glu Gln Phe Asn
        115                 120                 125

Ser Thr Tyr Arg Val Val Ser Val Leu Thr Val Leu His Gln Asp Trp
130                 135                 140

Leu Asn Gly Lys Glu Tyr Lys Cys Lys Val Ser Asn Lys Gly Leu Pro
145                 150                 155                 160

Ser Ser Ile Glu Lys Thr Ile Ser Lys Ala Lys Gly Gln Pro Arg Glu
                165                 170                 175

Pro Gln Val Tyr Thr Leu Pro Pro Ser Gln Glu Glu Met Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Arg
225                 230                 235                 240
```

-continued

```
Leu Thr Val Asp Lys Ser Arg Trp Gln Glu Gly Asn Val Phe Ser Cys
            245                 250                 255

Ser Val Met His Glu Ala Leu His Asn His Tyr Thr Gln Lys Ser Leu
        260                 265                 270

Ser Leu Ser Leu Gly Gly Gly Gly Ser Gly Ser Ala His Pro Ile Pro
    275                 280                 285

Asp Ser Ser Pro Leu Leu Gln Phe Gly Gly Gln Val Arg Gln Arg Tyr
290                 295                 300

Leu Tyr Thr Asp Asp Ala Cys Gln Thr Glu Ala His Leu Glu Ile Arg
305                 310                 315                 320

Glu Asp Gly Thr Val Gly Gly Ala Ala Asp Gln Ser Pro Glu Ser Leu
                325                 330                 335

Leu Gln Leu Lys Ala Leu Lys Pro Gly Val Ile Gln Ile Leu Gly Val
            340                 345                 350

Lys Thr Ser Arg Phe Leu Cys Gln Arg Pro Asp Gly Ala Leu Tyr Gly
        355                 360                 365

Ser Leu His Phe Asp Pro Glu Ala Cys Ser Phe Arg Glu Leu Leu Leu
    370                 375                 380

Glu Asp Gly Tyr Asn Val Tyr Gln Ser Glu Ala His Gly Leu Pro Leu
385                 390                 395                 400

His Leu Pro Gly Cys Lys Ser Pro His Arg Asp Pro Ala Pro Arg Gly
                405                 410                 415

Pro Ala Arg Phe Leu Pro Leu Pro Gly Leu Pro Pro Ala Pro Pro Glu
            420                 425                 430

Pro Pro Gly Ile Leu Ala Pro Gln Pro Pro Asp Val Gly Ser Ser Asp
        435                 440                 445

Pro Leu Ser Met Val Tyr Pro Ser Gln Gly Arg Ser Pro Ser Tyr Ala
    450                 455                 460

Ser
465

<210> SEQ ID NO 32
<211> LENGTH: 465
<212> TYPE: PRT
<213> ORGANISM: Artificial Sequence
<220> FEATURE:
<223> OTHER INFORMATION: GLP1(7-36)
      A8G,V16L,S18K,Y19Q,G22E,Q23E,A25V,K26Q,E27L,A30E,V33L,K34A,G35T,R
      36G_[19GS]_IgG4 Fc_variant [7GS]
      FGF21(His29-Ser209)Q55C,N149C,G198Y

<400> SEQUENCE: 32

His Gly Glu Gly Thr Phe Thr Ser Asp Leu Ser Lys Gln Leu Glu Glu
1               5                   10                  15

Glu Ala Val Gln Leu Phe Ile Glu Trp Leu Leu Ala Thr Gly Gly Gly
            20                  25                  30

Gly Gly Gly Gly Gly Ser Gly Gly Gly Ser Gly Gly Gly Gly Gly Ser
        35                  40                  45

Ala Glu Ser Lys Tyr Gly Pro Pro Cys Pro Pro Cys Pro Ala Pro Glu
    50                  55                  60

Phe Glu Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser Gln Glu Asp Pro Glu Val Gln Phe Asn Trp Tyr Val Asp Gly
            100                 105                 110
```

```
Val Glu Val His Asn Ala Lys Thr Lys Pro Arg Glu Gln Phe Asn
            115                 120                 125
Ser Thr Tyr Arg Val Val Ser Val Leu Thr Val Leu His Gln Asp Trp
130                 135                 140
Leu Asn Gly Lys Glu Tyr Lys Cys Lys Val Ser Asn Lys Gly Leu Pro
145                 150                 155                 160
Ser Ser Ile Glu Lys Thr Ile Ser Lys Ala Lys Gly Gln Pro Arg Glu
                165                 170                 175
Pro Gln Val Tyr Thr Leu Pro Pro Ser Gln Glu Glu Met Thr Lys Asn
            180                 185                 190
Gln Val Ser Leu Thr Cys Leu Val Lys Gly Phe Tyr Pro Ser Asp Ile
        195                 200                 205
Ala Val Glu Trp Glu Ser Asn Gly Gln Pro Glu Asn Asn Tyr Lys Thr
    210                 215                 220
Thr Pro Pro Val Leu Asp Ser Asp Gly Ser Phe Phe Leu Tyr Ser Arg
225                 230                 235                 240
Leu Thr Val Asp Lys Ser Arg Trp Gln Glu Gly Asn Val Phe Ser Cys
                245                 250                 255
Ser Val Met His Glu Ala Leu His Asn His Tyr Thr Gln Lys Ser Leu
            260                 265                 270
Ser Leu Ser Leu Gly Gly Gly Gly Ser Gly Ser Ala His Pro Ile Pro
        275                 280                 285
Asp Ser Ser Pro Leu Leu Gln Phe Gly Gly Gln Val Arg Gln Arg Tyr
    290                 295                 300
Leu Tyr Thr Asp Asp Ala Cys Gln Thr Glu Ala His Leu Glu Ile Arg
305                 310                 315                 320
Glu Asp Gly Thr Val Gly Gly Ala Ala Asp Gln Ser Pro Glu Ser Leu
                325                 330                 335
Leu Gln Leu Lys Ala Leu Lys Pro Gly Val Ile Gln Ile Leu Gly Val
            340                 345                 350
Lys Thr Ser Arg Phe Leu Cys Gln Arg Pro Asp Gly Ala Leu Tyr Gly
        355                 360                 365
Ser Leu His Phe Asp Pro Glu Ala Cys Ser Phe Arg Glu Leu Leu Leu
    370                 375                 380
Glu Asp Gly Tyr Asn Val Tyr Gln Ser Glu Ala His Gly Leu Pro Leu
385                 390                 395                 400
His Leu Pro Gly Cys Lys Ser Pro His Arg Asp Pro Ala Pro Arg Gly
                405                 410                 415
Pro Ala Arg Phe Leu Pro Leu Pro Gly Leu Pro Pro Ala Pro Pro Glu
            420                 425                 430
Pro Pro Gly Ile Leu Ala Pro Gln Pro Pro Asp Val Gly Ser Ser Asp
        435                 440                 445
Pro Leu Ser Met Val Tyr Pro Ser Gln Gly Arg Ser Pro Ser Tyr Ala
    450                 455                 460
Ser
465

<210> SEQ ID NO 33
<211> LENGTH: 474
<212> TYPE: PRT
<213> ORGANISM: Artificial Sequence
<220> FEATURE:
<223> OTHER INFORMATION: GLP1(7-36)
      A8G,V16L,S18K,Y19Q,G22E,Q23E,A25V,K26Q,E27L,A30E,V33L,K34A,G35T,R
      36G,insPSSGEPPPE_[19GS]_IgG4 Fc_variant
      [7GS]_FGF21(His29-Ser209)Q55C,N149C,G198Y
```

<400> SEQUENCE: 33

```
His Gly Glu Gly Thr Phe Thr Ser Asp Leu Ser Lys Gln Leu Glu Glu
1               5                   10                  15

Glu Ala Val Gln Leu Phe Ile Glu Trp Leu Ala Thr Gly Pro Ser
            20                  25                  30

Ser Gly Glu Pro Pro Gly Gly Gly Gly Gly Gly Ser Gly
        35                  40                  45

Gly Gly Gly Ser Gly Gly Gly Ser Ala Glu Ser Lys Tyr Gly Pro
50                  55                  60

Pro Cys Pro Pro Cys Pro Ala Pro Glu Phe Glu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser Gln Glu Asp Pro Glu
                100                 105                 110

Val Gln Phe Asn Trp Tyr Val Asp Gly Val Glu Val His Asn Ala Lys
            115                 120                 125

Thr Lys Pro Arg Glu Glu Gln Phe Asn Ser Thr Tyr Arg Val Val Ser
130                 135                 140

Val Leu Thr Val Leu His Gln Asp Trp Leu Asn Gly Lys Glu Tyr Lys
145                 150                 155                 160

Cys Lys Val Ser Asn Lys Gly Leu Pro Ser Ser Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Gln Glu Glu Met Thr Lys Asn Gln Val Ser Leu Thr Cys Leu
            195                 200                 205

Val Lys Gly Phe Tyr Pro Ser Asp Ile Ala Val Glu Trp Glu Ser Asn
210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Arg Leu Thr Val Asp Lys Ser Arg
                245                 250                 255

Trp Gln Glu Gly Asn Val Phe Ser Cys Ser Val Met His Glu Ala Leu
            260                 265                 270

His Asn His Tyr Thr Gln Lys Ser Leu Ser Leu Ser Leu Gly Gly Gly
            275                 280                 285

Gly Ser Gly Ser Ala His Pro Ile Pro Asp Ser Ser Pro Leu Leu Gln
290                 295                 300

Phe Gly Gly Gln Val Arg Gln Arg Tyr Leu Tyr Thr Asp Asp Ala Cys
305                 310                 315                 320

Gln Thr Glu Ala His Leu Glu Ile Arg Glu Asp Gly Thr Val Gly Gly
                325                 330                 335

Ala Ala Asp Gln Ser Pro Glu Ser Leu Leu Gln Leu Lys Ala Leu Lys
            340                 345                 350

Pro Gly Val Ile Gln Ile Leu Gly Val Lys Thr Ser Arg Phe Leu Cys
            355                 360                 365

Gln Arg Pro Asp Gly Ala Leu Tyr Gly Ser Leu His Phe Asp Pro Glu
        370                 375                 380

Ala Cys Ser Phe Arg Glu Leu Leu Glu Asp Gly Tyr Asn Val Tyr
385                 390                 395                 400

Gln Ser Glu Ala His Gly Leu Pro Leu His Leu Pro Gly Cys Lys Ser
```

```
                    405                 410                 415
Pro His Arg Asp Pro Ala Pro Arg Gly Pro Ala Arg Phe Leu Pro Leu
                420                 425                 430

Pro Gly Leu Pro Pro Ala Pro Pro Glu Pro Pro Gly Ile Leu Ala Pro
            435                 440                 445

Gln Pro Pro Asp Val Gly Ser Ser Asp Pro Leu Ser Met Val Tyr Pro
        450                 455                 460

Ser Gln Gly Arg Ser Pro Ser Tyr Ala Ser
465                 470

<210> SEQ ID NO 34
<211> LENGTH: 474
<212> TYPE: PRT
<213> ORGANISM: Artificial Sequence
<220> FEATURE:
<223> OTHER INFORMATION: GLP1(7-36)
      insG,A8G,V16L,S18K,Y19Q,G22E,Q23E,A24R,A25V,K26Q,A30E,insPSSGAPPP
      S_[19GS]_IgG4 Fc_variant
      [7GS]_FGF21(His29-Ser209)Q55C,N149C,delP199

<400> SEQUENCE: 34

Gly His Gly Glu Gly Thr Phe Thr Ser Asp Leu Ser Lys Gln Leu Glu
1               5                   10                  15

Glu Glu Arg Val Gln Glu Phe Ile Glu Trp Leu Val Lys Gly Arg Pro
            20                  25                  30

Ser Ser Gly Ala Pro Pro Pro Ser Gly Gly Gly Gly Ser Gly Gly Ser
        35                  40                  45

Gly Gly Gly Gly Ser Gly Gly Gly Ser Ala Glu Ser Lys Tyr Gly
    50                  55                  60

Pro Pro Cys Pro Pro Cys Pro Ala Pro Glu Phe Glu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser Gln Glu Asp Pro
            100                 105                 110

Glu Val Gln Phe Asn Trp Tyr Val Asp Gly Val Glu Val His Asn Ala
        115                 120                 125

Lys Thr Lys Pro Arg Glu Glu Gln Phe Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Gly Leu Pro Ser Ser Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Gln Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Arg Leu Thr Val Asp Lys Ser
                245                 250                 255

Arg Trp Gln Glu Gly Asn Val Phe Ser Cys Ser Val Met His Glu Ala
            260                 265                 270

Leu His Asn His Tyr Thr Gln Lys Ser Leu Ser Leu Ser Leu Gly Gly
```

```
                275                 280                 285
Gly Gly Ser Gly Ser Ala His Pro Ile Pro Asp Ser Ser Pro Leu Leu
            290                 295                 300
Gln Phe Gly Gly Gln Val Arg Gln Arg Tyr Leu Tyr Thr Asp Asp Ala
305                 310                 315                 320
Cys Gln Thr Glu Ala His Leu Glu Ile Arg Glu Asp Gly Thr Val Gly
                325                 330                 335
Gly Ala Ala Asp Gln Ser Pro Glu Ser Leu Leu Gln Leu Lys Ala Leu
            340                 345                 350
Lys Pro Gly Val Ile Gln Ile Leu Gly Val Lys Thr Ser Arg Phe Leu
            355                 360                 365
Cys Gln Arg Pro Asp Gly Ala Leu Tyr Gly Ser Leu His Phe Asp Pro
370                 375                 380
Glu Ala Cys Ser Phe Arg Glu Leu Leu Leu Glu Asp Gly Tyr Asn Val
385                 390                 395                 400
Tyr Gln Ser Glu Ala His Gly Leu Pro Leu His Leu Pro Gly Cys Lys
                405                 410                 415
Ser Pro His Arg Asp Pro Ala Pro Arg Gly Pro Ala Arg Phe Leu Pro
            420                 425                 430
Leu Pro Gly Leu Pro Pro Ala Pro Pro Glu Pro Pro Gly Ile Leu Ala
            435                 440                 445
Pro Gln Pro Pro Asp Val Gly Ser Ser Asp Pro Leu Ser Met Val Gly
450                 455                 460
Ser Gln Gly Arg Ser Pro Ser Tyr Ala Ser
465                 470

<210> SEQ ID NO 35
<211> LENGTH: 473
<212> TYPE: PRT
<213> ORGANISM: Artificial Sequence
<220> FEATURE:
<223> OTHER INFORMATION: GLP1(7-36)
      A8G,V16L,S18K,Y19Q,G22E,Q23E,A25V,K26Q,E27L,A30E,V33E,K34A,G35T,R
      36G,insPSSGAPPPS_[19GS]_IgG4 Fc_variant
      [7GS]_FGF21(His29-Ser209)Q55C,N149C,delP199

<400> SEQUENCE: 35

His Gly Glu Gly Thr Phe Thr Ser Asp Leu Ser Lys Gln Leu Glu Glu
1               5                   10                  15
Glu Ala Val Gln Leu Phe Ile Glu Trp Leu Glu Ala Thr Gly Pro Ser
                20                  25                  30
Ser Gly Ala Pro Pro Pro Ser Gly Gly Gly Gly Gly Gly Ser Gly
            35                  40                  45
Gly Gly Ser Gly Gly Gly Gly Ser Ala Glu Ser Lys Tyr Gly Pro
        50                  55                  60
Pro Cys Pro Pro Cys Pro Ala Pro Glu Phe Glu Gly Gly Pro Ser Val
65                  70                  75                  80
Phe Leu Phe Pro Pro Lys Pro Lys Asp Thr Leu Met Ile Ser Arg Thr
                85                  90                  95
Pro Glu Val Thr Cys Val Val Val Asp Val Ser Gln Glu Asp Pro Glu
                100                 105                 110
Val Gln Phe Asn Trp Tyr Val Asp Gly Val Glu Val His Asn Ala Lys
            115                 120                 125
Thr Lys Pro Arg Glu Glu Gln Phe Asn Ser Thr Tyr Arg Val Val Ser
        130                 135                 140
Val Leu Thr Val Leu His Gln Asp Trp Leu Asn Gly Lys Glu Tyr Lys
```

```
            145                 150                 155                 160
Cys Lys Val Ser Asn Lys Gly Leu Pro Ser Ser Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Gln Glu Glu Met Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Arg Leu Thr Val Asp Lys Ser Arg
                245                 250                 255

Trp Gln Glu Gly Asn Val Phe Ser Cys Ser Val Met His Glu Ala Leu
            260                 265                 270

His Asn His Tyr Thr Gln Lys Ser Leu Ser Leu Ser Leu Gly Gly Gly
        275                 280                 285

Gly Ser Gly Ser Ala His Pro Ile Pro Asp Ser Ser Pro Leu Leu Gln
    290                 295                 300

Phe Gly Gly Gln Val Arg Gln Arg Tyr Leu Tyr Thr Asp Asp Ala Cys
305                 310                 315                 320

Gln Thr Glu Ala His Leu Glu Ile Arg Glu Asp Gly Thr Val Gly Gly
                325                 330                 335

Ala Ala Asp Gln Ser Pro Glu Ser Leu Leu Gln Leu Lys Ala Leu Lys
            340                 345                 350

Pro Gly Val Ile Gln Ile Leu Gly Val Lys Thr Ser Arg Phe Leu Cys
        355                 360                 365

Gln Arg Pro Asp Gly Ala Leu Tyr Gly Ser Leu His Phe Asp Pro Glu
    370                 375                 380

Ala Cys Ser Phe Arg Glu Leu Leu Leu Glu Asp Gly Tyr Asn Val Tyr
385                 390                 395                 400

Gln Ser Glu Ala His Gly Leu Pro Leu His Leu Pro Gly Cys Lys Ser
                405                 410                 415

Pro His Arg Asp Pro Ala Pro Arg Gly Pro Ala Arg Phe Leu Pro Leu
            420                 425                 430

Pro Gly Leu Pro Pro Ala Pro Pro Glu Pro Gly Ile Leu Ala Pro
        435                 440                 445

Gln Pro Pro Asp Val Gly Ser Ser Asp Pro Leu Ser Met Val Gly Ser
    450                 455                 460

Gln Gly Arg Ser Pro Ser Tyr Ala Ser
465                 470

<210> SEQ ID NO 36
<211> LENGTH: 472
<212> TYPE: PRT
<213> ORGANISM: Artificial Sequence
<220> FEATURE:
<223> OTHER INFORMATION: GLP1(7-36)
      insG,A8G,V16L,S18I,Y19Q,G22E,Q23E,A25V,K26R,E27L,A30E,V33L,K34A,R
      36G,insPKKQRLS_[19GS]_IgG4 Fc_variant
      [7GS]_FGF21(His29-Ser209)Q55C,N149C,delP199

<400> SEQUENCE: 36

Gly His Gly Glu Gly Thr Phe Thr Ser Asp Leu Ser Ile Gln Leu Glu
1               5                   10                  15

Glu Glu Ala Val Arg Leu Phe Ile Glu Trp Leu Leu Ala Gly Gly Pro
```

```
            20                  25                  30
Lys Lys Gln Arg Leu Ser Gly Gly Gly Gly Gly Ser Gly Gly
            35                  40                  45
Gly Gly Ser Gly Gly Gly Ser Ala Glu Ser Lys Tyr Gly Pro Pro
            50                  55                  60
Cys Pro Pro Cys Pro Ala Pro Glu Phe Glu Gly Gly Pro Ser Val Phe
 65                  70                  75                  80
Leu Phe Pro Pro Lys Pro Lys Asp Thr Leu Met Ile Ser Arg Thr Pro
                    85                  90                  95
Glu Val Thr Cys Val Val Val Asp Val Ser Gln Glu Asp Pro Glu Val
                100                 105                 110
Gln Phe Asn Trp Tyr Val Asp Gly Val Glu Val His Asn Ala Lys Thr
            115                 120                 125
Lys Pro Arg Glu Glu Gln Phe Asn Ser Thr Tyr Arg Val Val Ser Val
        130                 135                 140
Leu Thr Val Leu His Gln Asp Trp Leu Asn Gly Lys Glu Tyr Lys Cys
145                 150                 155                 160
Lys Val Ser Asn Lys Gly Leu Pro Ser Ser Ile Glu Lys Thr Ile Ser
                165                 170                 175
Lys Ala Lys Gly Gln Pro Arg Glu Pro Gln Val Tyr Thr Leu Pro Pro
            180                 185                 190
Ser Gln Glu Glu Met Thr Lys Asn Gln Val Ser Leu Thr Cys Leu Val
            195                 200                 205
Lys Gly Phe Tyr Pro Ser Asp Ile Ala Val Glu Trp Glu Ser Asn Gly
            210                 215                 220
Gln Pro Glu Asn Asn Tyr Lys Thr Thr Pro Pro Val Leu Asp Ser Asp
225                 230                 235                 240
Gly Ser Phe Phe Leu Tyr Ser Arg Leu Thr Val Asp Lys Ser Arg Trp
                245                 250                 255
Gln Glu Gly Asn Val Phe Ser Cys Ser Val Met His Glu Ala Leu His
            260                 265                 270
Asn His Tyr Thr Gln Lys Ser Leu Ser Leu Ser Leu Gly Gly Gly Gly
            275                 280                 285
Ser Gly Ser Ala His Pro Ile Pro Asp Ser Ser Pro Leu Leu Gln Phe
    290                 295                 300
Gly Gly Gln Val Arg Gln Arg Tyr Leu Tyr Thr Asp Asp Ala Cys Gln
305                 310                 315                 320
Thr Glu Ala His Leu Glu Ile Arg Glu Asp Gly Thr Val Gly Gly Ala
                325                 330                 335
Ala Asp Gln Ser Pro Glu Ser Leu Leu Gln Leu Lys Ala Leu Lys Pro
            340                 345                 350
Gly Val Ile Gln Ile Leu Gly Val Lys Thr Ser Arg Phe Leu Cys Gln
            355                 360                 365
Arg Pro Asp Gly Ala Leu Tyr Gly Ser Leu His Phe Asp Pro Glu Ala
    370                 375                 380
Cys Ser Phe Arg Glu Leu Leu Leu Glu Asp Gly Tyr Asn Val Tyr Gln
385                 390                 395                 400
Ser Glu Ala His Gly Leu Pro Leu His Leu Pro Gly Cys Lys Ser Pro
                405                 410                 415
His Arg Asp Pro Ala Pro Arg Gly Pro Ala Arg Phe Leu Pro Leu Pro
            420                 425                 430
Gly Leu Pro Pro Ala Pro Pro Glu Pro Pro Gly Ile Leu Ala Pro Gln
            435                 440                 445
```

-continued

Pro Pro Asp Val Gly Ser Ser Asp Pro Leu Ser Met Val Gly Ser Gln
      450                 455                 460

Gly Arg Ser Pro Ser Tyr Ala Ser
465                 470

<210> SEQ ID NO 37
<211> LENGTH: 30
<212> TYPE: PRT
<213> ORGANISM: Artificial Sequence
<220> FEATURE:
<223> OTHER INFORMATION: GLP-1RA, general sequence
<220> FEATURE:
<221> NAME/KEY: misc_feature
<222> LOCATION: (10)..(10)
<223> OTHER INFORMATION: Xaa is any amino acid, e.g., L or K
<220> FEATURE:
<221> NAME/KEY: misc_feature
<222> LOCATION: (12)..(12)
<223> OTHER INFORMATION: Xaa is any amino acid, e.g., K or I
<220> FEATURE:
<221> NAME/KEY: misc_feature
<222> LOCATION: (14)..(14)
<223> OTHER INFORMATION: Xaa is any amino acid, e.g., L or M
<220> FEATURE:
<221> NAME/KEY: misc_feature
<222> LOCATION: (15)..(15)
<223> OTHER INFORMATION: Xaa is any amino acid, e.g., E or D
<220> FEATURE:
<221> NAME/KEY: misc_feature
<222> LOCATION: (18)..(18)
<223> OTHER INFORMATION: Xaa is any amino acid, e.g., A or R
<220> FEATURE:
<221> NAME/KEY: misc_feature
<222> LOCATION: (20)..(20)
<223> OTHER INFORMATION: Xaa is any amino acid, e.g., R or Q
<220> FEATURE:
<221> NAME/KEY: misc_feature
<222> LOCATION: (21)..(21)
<223> OTHER INFORMATION: Xaa is any amino acid, e.g., L or E
<220> FEATURE:
<221> NAME/KEY: misc_feature
<222> LOCATION: (27)..(27)
<223> OTHER INFORMATION: Xaa is any amino acid, e.g., L, E, K or V
<220> FEATURE:
<221> NAME/KEY: misc_feature
<222> LOCATION: (28)..(28)
<223> OTHER INFORMATION: Xaa is any amino acid, e.g., A, N or K
<220> FEATURE:
<221> NAME/KEY: misc_feature
<222> LOCATION: (29)..(29)
<223> OTHER INFORMATION: Xaa is any amino acid, e.g., T or G
<220> FEATURE:
<221> NAME/KEY: misc_feature
<222> LOCATION: (30)..(30)
<223> OTHER INFORMATION: Xaa is any amino acid, e.g., G or R

<400> SEQUENCE: 37

His Gly Glu Gly Thr Phe Thr Ser Asp Xaa Ser Xaa Gln Xaa Xaa Glu
1               5                   10                  15

Glu Xaa Val Xaa Xaa Phe Ile Glu Trp Leu Xaa Xaa Xaa Xaa
            20                  25                  30

<210> SEQ ID NO 38
<211> LENGTH: 9
<212> TYPE: PRT
<213> ORGANISM: Artificial Sequence
<220> FEATURE:
<223> OTHER INFORMATION: C-terminal peptide extension I

<400> SEQUENCE: 38

Pro Ser Ser Gly Ala Pro Pro Ser
1               5

```
<210> SEQ ID NO 39
<211> LENGTH: 9
<212> TYPE: PRT
<213> ORGANISM: Artificial Sequence
<220> FEATURE:
<223> OTHER INFORMATION: C-terminal peptide extension II

<400> SEQUENCE: 39

Pro Val Ser Gly Ala Pro Pro Pro Ser
1               5

<210> SEQ ID NO 40
<211> LENGTH: 10
<212> TYPE: PRT
<213> ORGANISM: Artificial Sequence
<220> FEATURE:
<223> OTHER INFORMATION: C-terminal peptide extension III

<400> SEQUENCE: 40

Pro Ser Ser Gly Glu Pro Pro Pro Glu Ser
1               5                   10

<210> SEQ ID NO 41
<211> LENGTH: 9
<212> TYPE: PRT
<213> ORGANISM: Artificial Sequence
<220> FEATURE:
<223> OTHER INFORMATION: C-terminal peptide extension IV

<400> SEQUENCE: 41

Pro Ser Ser Gly Glu Pro Pro Pro Glu
1               5

<210> SEQ ID NO 42
<211> LENGTH: 7
<212> TYPE: PRT
<213> ORGANISM: Artificial Sequence
<220> FEATURE:
<223> OTHER INFORMATION: C-terminal peptide extension V

<400> SEQUENCE: 42

Pro Lys Lys Gln Arg Leu Ser
1               5

<210> SEQ ID NO 43
<211> LENGTH: 7
<212> TYPE: PRT
<213> ORGANISM: Artificial Sequence
<220> FEATURE:
<223> OTHER INFORMATION: C-terminal peptide extension VI

<400> SEQUENCE: 43

Pro Lys Lys Ile Arg Tyr Ser
1               5
```

FGF21 COMPOUND / GLP-1R AGONIST COMBINATIONS WITH OPTIMIZED ACTIVITY RATIO

RELATED APPLICATION

This application claims the benefit of European Patent Application No. 16306776.2, filed Dec. 22, 2016, the entire disclosure of which are hereby incorporated herein by reference.

TECHNICAL FIELD OF THE INVENTION

The present invention relates to combinations, pharmaceutical compositions and fusion molecules comprising an FGF21 (fibroblast growth factor 21) compound and a GLP-1R (glucagon-like peptide-1 receptor) agonist with optimized GLP-1R agonist/FGF21 compound activity ratio. It further relates to their use as medicaments, in particular for the treatment of obesity, being overweight, metabolic syndrome, diabetes mellitus, diabetic retinopathy, hyperglycemia, dyslipidemia, Non-Alcoholic SteatoHepatitis (NASH) and/or atherosclerosis.

BACKGROUND OF THE INVENTION

Administration of fibroblast growth factor 21 (FGF21) compounds, e.g., recombinantly produced FGF21 polypeptides, results in substantial decrease in body weight, blood glucose and plasma lipids as well as in improved insulin sensitivity, as demonstrated, for example, by Gaich et al. (2013) Cell Metab 18(3): 333-340 and Dong et al. (2015) Br J Clin Pharmacol 80(5): 1051-1063. Glucagon-like peptide-1 receptor (GLP-1R) agonists provide effective glucose and body weight lowering in humans, as shown, for example, by Astrup et al. (2012) Int J Obes (Lond) 36(6): 843-854 and Nauck et al. (2013) Diabetes Obes Metab 15(3): 204-212. Combining the beneficial effects of FGF21 administration with the glucose-lowering effects of GLP-1 receptor agonists surprisingly resulted in synergistic effects (see, e.g., WO 2011/089203 A1 and WO 2014/037373 A1) that provide a more comprehensive treatment of diseases/disorders, such as obesity, being overweight, metabolic syndrome, diabetes mellitus, diabetic retinopathy, hyperglycemia, dyslipidemia, Non-Alcoholic SteatoHepatitis (NASH) and/or atherosclerosis.

SUMMARY OF THE INVENTION

A combination of an FGF21 compound and a GLP-1R agonist, e.g., in the form of a fusion protein, can, for example, be used for improving glycemic control in overweight to obese dyslipidemic patients with type 2 diabetes mellitus.

Notably, FGF21 and GLP-1 (as the primary GLP-1R agonist) exert their pharmacological effects at different plasma concentrations. More particularly, FGF21 effects kick in at higher plasma levels as compared to GLP-1 effects. In addition, at higher levels, GLP-1 is known to have adverse effects, e.g., nausea and vomiting. Taken together, this implies a potential risk of GLP-1-mediated adverse effects when administering a combination of an FGF21 compound and a GLP-1R agonist, e.g., in the form of a fusion protein.

Accordingly, it was an object of the present invention to determine the optimal GLP-1R agonist/FGF21 compound activity ratio in order to achieve the beneficial effects while avoiding potential adverse effects (e.g., nausea and vomiting). It was a further object of the present invention to provide corresponding combinations, pharmaceutical compositions and fusion molecules with optimized GLP-1R agonist/FGF21 compound activity ratio.

In one aspect, the present invention relates to a combination comprising an FGF21 (fibroblast growth factor 21) compound and a GLP-1R (glucagon-like peptide-1 receptor) agonist,
wherein the FGF21 compound has an FGF21 activity which is the same or substantially the same as the FGF21 activity of native FGF21, and
wherein the GLP-1R agonist has a GLP-1R agonistic activity which is 9- to 531-fold (or 9.449- to 531.0-fold) reduced as compared to the GLP-1R agonistic activity of native GLP-1(7-36).

In one embodiment, the FGF21 activity refers to activation of the FGF21 receptor. In one embodiment, the term refers to the activity in vitro. In one embodiment, activation of the FGF21 receptor is determined by measuring FGF21 receptor autophosphorylation upon contact with the FGF21 compound in vitro. In one embodiment, FGF21 activity is determined by using an In-Cell Western (ICW) assay, e.g., essentially as described in Example 3.

In one embodiment, the GLP-1R agonistic activity refers to activation of the GLP-1 receptor. In one embodiment, the term refers to the agonistic activity in vitro. In one embodiment, activation of the GLP-1 receptor is determined by measuring the cAMP response of cells stably expressing GLP-1 receptor upon contact with the agonist in vitro. In one embodiment, activation of the GLP-1 receptor is determined essentially as described in Example 4.

In one embodiment, the GLP-1R agonist has a GLP-1R agonistic activity which is 9- to 482-fold (or 9.449- to 482.396-fold) or 9- to 319-fold (or 9.449- to 319.311-fold) or 9- to 121-fold (or 9.449- to 121.189-fold) reduced as compared to the GLP-1R agonistic activity of native GLP-1 (7-36).

In one embodiment, the GLP-1R agonist has a GLP-1R agonistic activity which is 9- to 319-fold reduced as compared to the GLP-1R agonistic activity of native GLP-1(7-36).

In one embodiment, the GLP-1R agonist has a GLP-1R agonistic activity which is at least 9.4-fold or at least 9.45-fold or at least 9.5-fold reduced as compared to the GLP-1R agonistic activity of native GLP-1(7-36).

In one embodiment, the GLP-1R agonist has a GLP-1R agonistic activity which is at least 10-fold reduced as compared to the GLP-1R agonistic activity of native GLP-1(7-36).

In one embodiment, the GLP-1R agonist has a GLP-1R agonistic activity which is at most 482.4-fold or at most 482.35-fold reduced as compared to the GLP-1R agonistic activity of native GLP-1(7-36).

In one embodiment, the GLP-1R agonist has a GLP-1R agonistic activity which is at most 482-fold reduced as compared to the GLP-1R agonistic activity of native GLP-1(7-36).

In one embodiment, the GLP-1R agonist has a GLP-1R agonistic activity which is 10- to 482-reduced as compared to the GLP-1R agonistic activity of native GLP-1(7-36).

In one embodiment, the GLP-1R agonist has a GLP-1R agonistic activity which is 10- to 319-reduced as compared to the GLP-1R agonistic activity of native GLP-1(7-36).

In one embodiment, the GLP-1R agonist has a GLP-1R agonistic activity which is 90- to 100-fold reduced as compared to the GLP-1R agonistic activity of native GLP-1(7-36).

In one embodiment, the GLP-1R agonist has a GLP-1R agonistic activity which is at least 18-fold (or at least 18.268-fold) reduced as compared to the GLP-1R agonistic activity of native GLP-1(7-36).

In one embodiment, the GLP-1R agonist has a GLP-1R agonistic activity which is 18- to 501-fold (or 18.268- to 500.686-fold) or 18- to 469-fold (or 18.268- to 468.679-fold) or 18- to 313-fold (or 18.268- to 313.214-fold) or 18- to 123-fold (or 18.268- to 123.466-fold) reduced as compared to the GLP-1R agonistic activity of native GLP-1(7-36).

In one embodiment, the GLP-1R agonist has a GLP-1R agonistic activity which is 18- to 313-fold reduced as compared to the GLP-1R agonistic activity of native GLP-1(7-36).

In one of the above embodiments, the GLP-1R agonist has a GLP-1R agonistic activity which is at least 18.2-fold or at least 18.3-fold reduced as compared to the GLP-1R agonistic activity of native GLP-1(7-36).

In one embodiment, the FGF21 compound is native FGF21 or an FGF21 variant having at least 80% or at least 90% or at least 95% amino acid sequence identity to the amino acid sequence of native FGF21.

In one embodiment, the GLP-1R agonist comprises or consists of the amino acid sequence (SEQ ID NO: 37)
H-G-E-G-T-F-T-S-D-$X_{10}$-S-$X_{12}$-Q-$X_{14}$-$X_{15}$-E-E-$X_{18}$-V-

$X_{20}$-$X_{21}$-F-I-E-W-L-$X_{27}$-$X_{28}$-$X_{29}$-$X_{30}$, wherein
$X_{10}$ is L or K;
$X_{12}$ is K or I;
$X_{14}$ is L or M;
$X_{15}$ is E or D;
$X_{18}$ is A or R;
$X_{20}$ is R or Q;
$X_{21}$ is L or E;
$X_{27}$ is L, E, K or V;
$X_{28}$ is A, N or K;
$X_{29}$ is T or G;
$X_{30}$ is G or R;
wherein, optionally, the amino acid sequence comprises at least one additional amino acid residue at its N-terminus; and wherein, optionally, the amino acid sequence comprises a peptide extension consisting of up to 12, 11 or 10 amino acid residues at its C-terminus.

In one embodiment, the GLP-1R agonist comprises or consists of an amino acid sequence selected from the group consisting of SEQ ID NOs: 9, 10, 12, 14, 15, 16, 17, 19 and 20.

In another aspect, the present invention relates to a pharmaceutical composition comprising an FGF21 (fibroblast growth factor 21) compound and a GLP-1R (glucagon-like peptide-1 receptor) agonist together with a pharmaceutically acceptable carrier and/or excipient, wherein the FGF21 compound has an FGF21 activity which is the same or substantially the same as the FGF21 activity of native FGF21, and wherein the GLP-1R agonist has a GLP-1R agonistic activity which is 9- to 531-fold (or 9.449- to 531.0-fold) reduced as compared to the GLP-1R agonistic activity of native GLP-1(7-36).

In one embodiment, the GLP-1R agonist and/or the FGF21 compound are as defined above.

In yet another aspect, the present invention relates to a fusion molecule comprising an FGF21 (fibroblast growth factor 21) compound and a GLP-1R (glucagon-like peptide-1 receptor) agonist, wherein the FGF21 compound has an FGF21 activity which is the same or substantially the same as the FGF21 activity of native FGF21, and wherein the GLP-1R agonist has a GLP-1R agonistic activity which is 9- to 531-fold (or 9.449- to 531.0-fold) reduced as compared to the GLP-1R agonistic activity of native GLP-1(7-36).

In one embodiment, the GLP-1R agonist and/or the FGF21 compound are as defined above.

In another aspect, the present invention relates to a nucleic acid molecule encoding a fusion molecule as defined above.

In another aspect, the present invention relates to a host cell containing a nucleic acid molecule as defined above.

In another aspect, the present invention relates to a kit comprising a combination as defined above, a pharmaceutical composition as defined above, a fusion molecule as defined above, a nucleic acid molecule as defined above or a host cell as defined above.

In another aspect, the present invention relates to a combination as defined above, a pharmaceutical composition as defined above, a fusion molecule as defined above, a nucleic acid molecule as defined above or a host cell as defined above for use as a medicament.

In another aspect, the present invention relates to a combination as defined above, a pharmaceutical composition as defined above, a fusion molecule as defined above, a nucleic acid molecule as defined above or a host cell as defined above for use in the treatment of a disease or disorder selected from the group consisting of obesity, being overweight, metabolic syndrome, diabetes mellitus, diabetic retinopathy, hyperglycemia, dyslipidemia, Non-Alcoholic SteatoHepatitis (NASH) and atherosclerosis.

In one embodiment, the disease or disorder is diabetes mellitus. In one embodiment, the diabetes mellitus is type 1 diabetes mellitus or type 2 diabetes mellitus.

In another aspect, the present invention relates to the use of a combination as defined above, a pharmaceutical composition as defined above, a fusion molecule as defined above, a nucleic acid molecule as defined above or a host cell as defined above in the manufacture of a medicament for the treatment of a disease or disorder selected from the group consisting of obesity, being overweight, metabolic syndrome, diabetes mellitus, diabetic retinopathy, hyperglycemia, dyslipidemia, Non-Alcoholic SteatoHepatitis (NASH) and atherosclerosis.

In one embodiment, the disease or disorder is diabetes mellitus. In one embodiment, the diabetes mellitus is type 1 diabetes mellitus or type 2 diabetes mellitus.

In another aspect, the present invention relates to a method of treating a disease or disorder selected from the group consisting of obesity, being overweight, metabolic syndrome, diabetes mellitus, diabetic retinopathy, hyperglycemia, dyslipidemia, Non-Alcoholic SteatoHepatitis (NASH) and atherosclerosis, the method comprising administering a combination as defined above, a pharmaceutical composition as defined above, a fusion molecule as defined above, a nucleic acid molecule as defined above or a host cell as defined above to a subject in need thereof.

In one embodiment, the disease or disorder is diabetes mellitus. In one embodiment, the diabetes mellitus is type 1 diabetes mellitus or type 2 diabetes mellitus.

In another aspect, the present invention relates to a GLP-1R agonist having a GLP-1R agonistic activity which is 9- to 531-fold (or 9.449- to 531.0-fold) reduced as compared to the GLP-1R agonistic activity of native GLP-1 (7-36).

In one embodiment, the GLP-1R agonist is as defined above.

In one embodiment, the GLP-1R agonist comprises or consists of the amino acid sequence (SEQ ID NO: 37)
H-G-E-G-T-F-T-S-D-$X_{10}$-S-$X_{12}$-Q-$X_{14}$-$X_{15}$-E-E-$X_{18}$-V-

$X_{20}$-$X_{21}$-F-I-E-W-L-$X_{27}$-$X_{28}$-$X_{29}$-$X_{30}$, wherein
$X_{10}$ is L or K;
$X_{12}$ is K or I;
$X_{14}$ is L or M;
$X_{15}$ is E or D;
$X_{18}$ is A or R;
$X_{20}$ is R or Q;
$X_{21}$ is L or E;
$X_{27}$ is L, E, K or V;
$X_{28}$ is A, N or K;
$X_{29}$ is T or G;
$X_{30}$ is G or R;
wherein, optionally, the amino acid sequence comprises at least one additional amino acid residue at its N-terminus; and
wherein, optionally, the amino acid sequence comprises a peptide extension consisting of up to 12, 11 or 10 amino acid residues at its C-terminus.

In one embodiment, the GLP-1R agonist comprises or consists of an amino acid sequence selected from the group consisting of SEQ ID NOs: 9, 10, 12, 14, 15, 16, 17, 19 and 20.

In another aspect, the present invention relates to a nucleic acid molecule encoding a GLP-1R agonist as defined above.

In another aspect, the present invention relates to a host cell containing a nucleic acid molecule as defined above.

In another aspect, the present invention relates to a pharmaceutical composition or kit comprising a GLP-1R agonist as defined above, a nucleic acid molecule as defined above or a host cell as defined above.

In another aspect, the present invention relates to a GLP-1R agonist as defined above, a pharmaceutical composition as defined above, a nucleic acid molecule as defined above or a host cell as defined above for use as a medicament.

In another aspect, the present invention relates to a GLP-1R agonist as defined above, a pharmaceutical composition as defined above, a nucleic acid molecule as defined above or a host cell as defined above for use in the treatment of a disease or disorder selected from the group consisting of obesity, being overweight, metabolic syndrome, diabetes mellitus, diabetic retinopathy, hyperglycemia, dyslipidemia, Non-Alcoholic SteatoHepatitis (NASH) and atherosclerosis.

In one embodiment, the disease or disorder is diabetes mellitus. In one embodiment, the diabetes mellitus is type 1 diabetes mellitus or type 2 diabetes mellitus.

In another aspect, the present invention relates to the use of a GLP-1R agonist as defined above, a pharmaceutical composition as defined above, a nucleic acid molecule as defined above or a host cell as defined above in the manufacture of a medicament for the treatment of a disease or disorder selected from the group consisting of obesity, being overweight, metabolic syndrome, diabetes mellitus, diabetic retinopathy, hyperglycemia, dyslipidemia, Non-Alcoholic SteatoHepatitis (NASH) and atherosclerosis.

In one embodiment, the disease or disorder is diabetes mellitus. In one embodiment, the diabetes mellitus is type 1 diabetes mellitus or type 2 diabetes mellitus.

In another aspect, the present invention relates to a method of treating a disease or disorder selected from the group consisting of obesity, being overweight, metabolic syndrome, diabetes mellitus, diabetic retinopathy, hyperglycemia, dyslipidemia, Non-Alcoholic SteatoHepatitis (NASH) and atherosclerosis, the method comprising administering a GLP-1R agonist as defined above, a pharmaceutical composition as defined above, a nucleic acid molecule as defined above or a host cell as defined above to a subject in need thereof.

In one embodiment, the disease or disorder is diabetes mellitus. In one embodiment, the diabetes mellitus is type 1 diabetes mellitus or type 2 diabetes mellitus.

Figure 2:
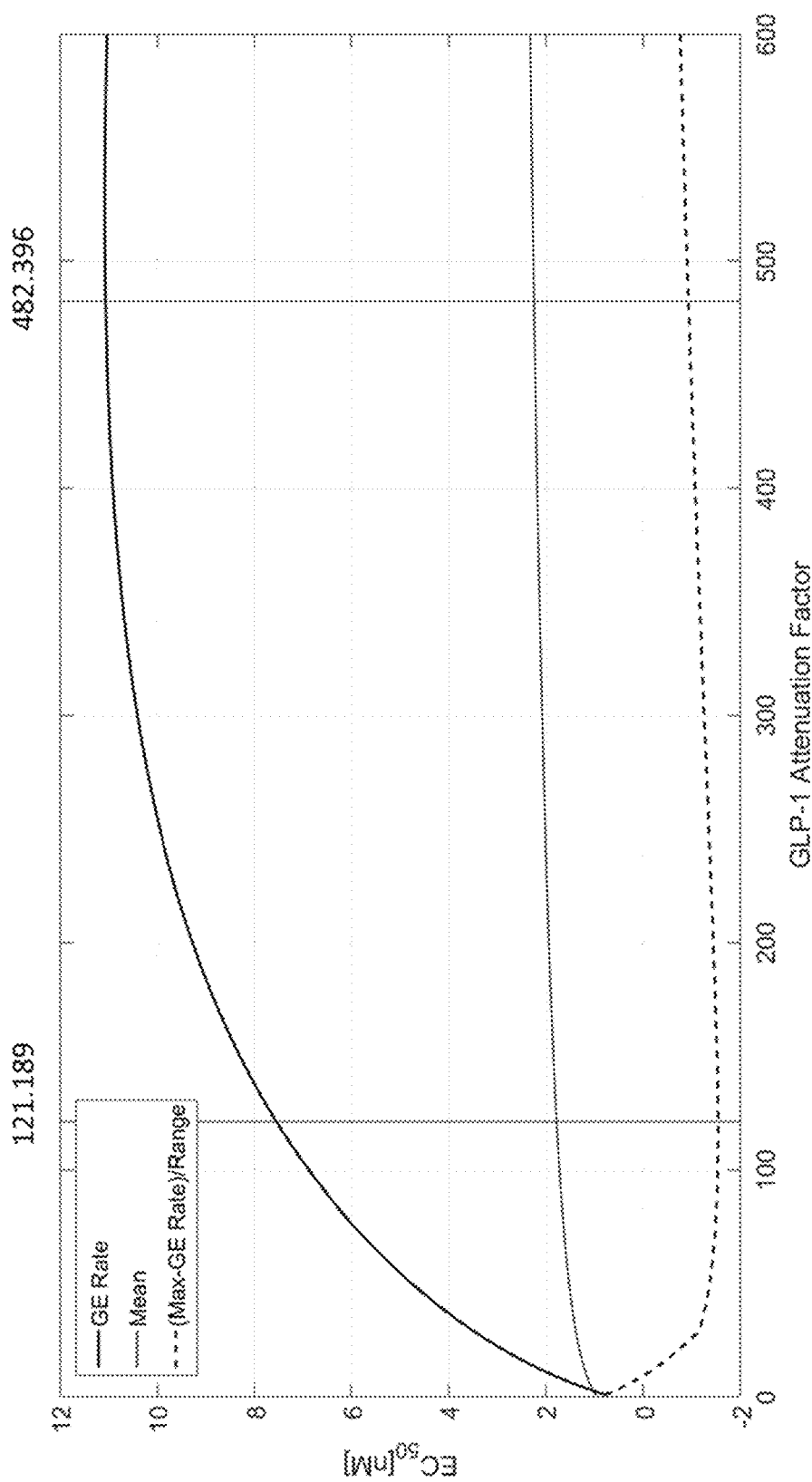

For GLP-1 attenuation factors greater than 9.449 (can be rounded to 9), EC50 of GLP-1-mediated gastrointestinal adverse effect (gastric emptying; GE-Rate) was greater than EC50 of pharmacodynamic effects (i.e., HbA1c, Adipose Mass, Non-HDL, Fatty Acids, Triglycerides);

Maximal distance between maximum of pharmacodynamics (HbA1c) and adverse effect (GE-Rate) normalized by spreading of FGF21- (lipids) and GLP-1-mediated effects (HbA1c) was 121.189; i.e. at 121.189 (can be rounded to 121), there is a maximal distance between maximum of pharmacodynamics effects (HbA1c) and adverse effect (GE-Rate) at a minimum distance between GLP-1-mediated effects (HbA1c) and mean FGF21-mediated effects (i.e., Adipose Mass, Non-HDL, Fatty Acids, Triglycerides) (see FIG. 2);

Maximal distance between maximum of pharmacodynamics (HbA1c) and adverse effect (GE-Rate) was 319.311 (can be rounded to 319);

Maximal distance between mean pharmacodynamics (i.e., HbA1c, Adipose Mass, Non-HDL, Fatty Acids, Triglycerides) and adverse effect (GE-Rate) was 482.396 (see FIG. 2; can be rounded to 482);

Maximum of gastric emptying rate at 531.0;

(all: vertical lines).

FIG. 2 is a graph showing EC50 of gastric emptying (GE) rate and mean pharmacodynamic effects (i.e., HbA1c, Triglycerides, Fatty Acids, Non-HDL, Adipose Mass) depending on GLP-1 attenuation factor (12-months simulation):

Maximal distance between mean pharmacodynamics (i.e., HbA1c, Adipose Mass, Non-HDL, Fatty Acids, Triglycerides) and adverse effect (GE-Rate) was 482.396 (right vertical line; can be rounded to 482);

Maximal distance between maximum of pharmacodynamics (HbA1c) and adverse effect (GE-Rate) normalized by spreading of FGF21- (lipids) and GLP-1-mediated effects (HbA1c) was 121.189 (left vertical line; can be rounded to 121). The curve "(Max-GE Rate)/Range" represents the ratio between the maximum distance between HbA1c and GE-Rate and the minimum distance between HbA1c and mean FGF21-mediated effects (i.e., Adipose Mass, Non-HDL, Fatty Acids, Triglycerides). At the minimum of the "(Max-GE Rate)/Range" curve (i.e. at 121.189), there is a maximal distance between maximum of pharmacodynamics effects (HbA1c) and adverse effect (GE-Rate) at a minimum distance between GLP-1-mediated effects (HbA1c) and FGF21-mediated effects (i.e., Adipose Mass, Non-HDL, Fatty Acids, Triglycerides).

Figure 3:
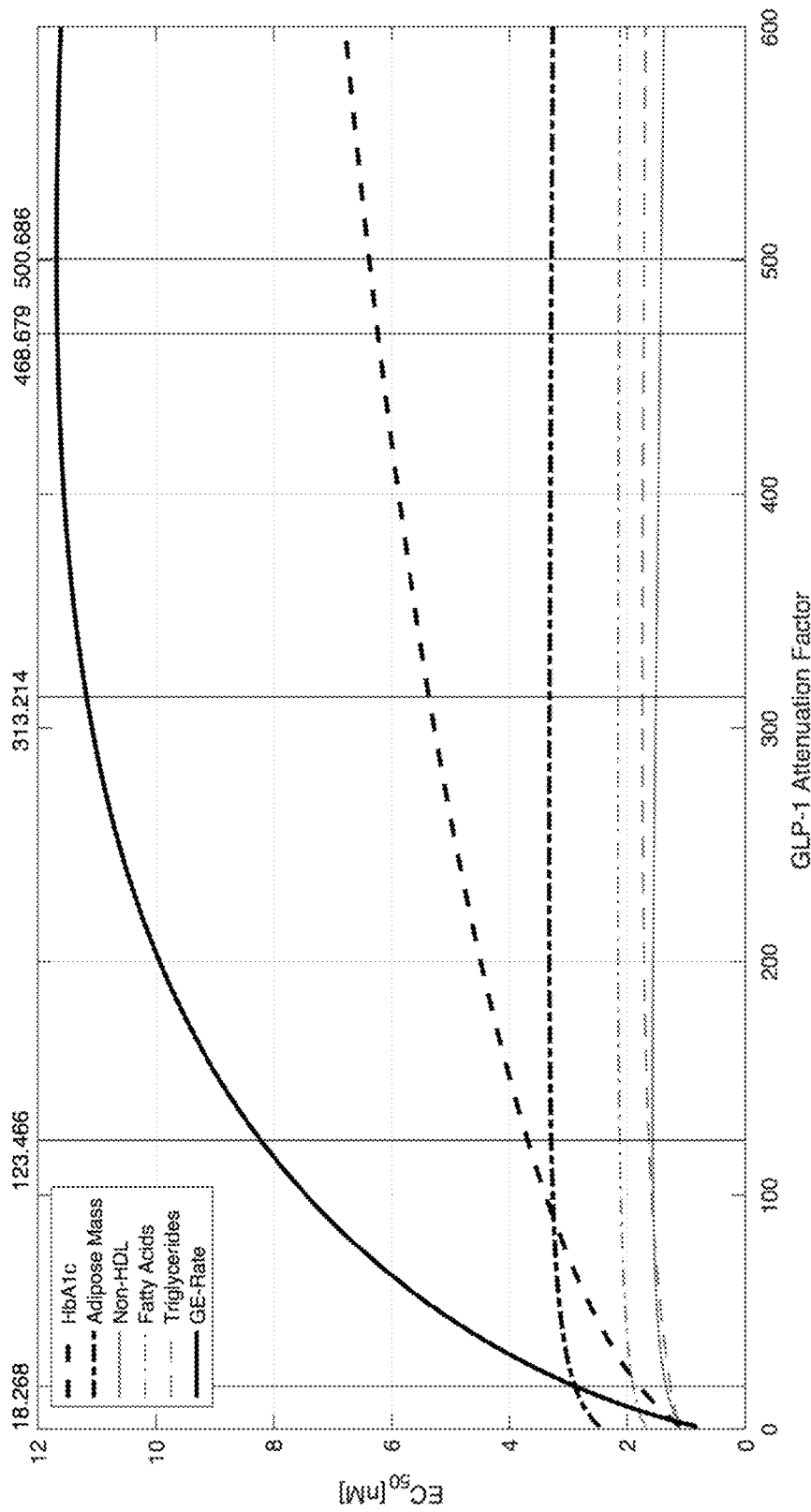
Figure 4:
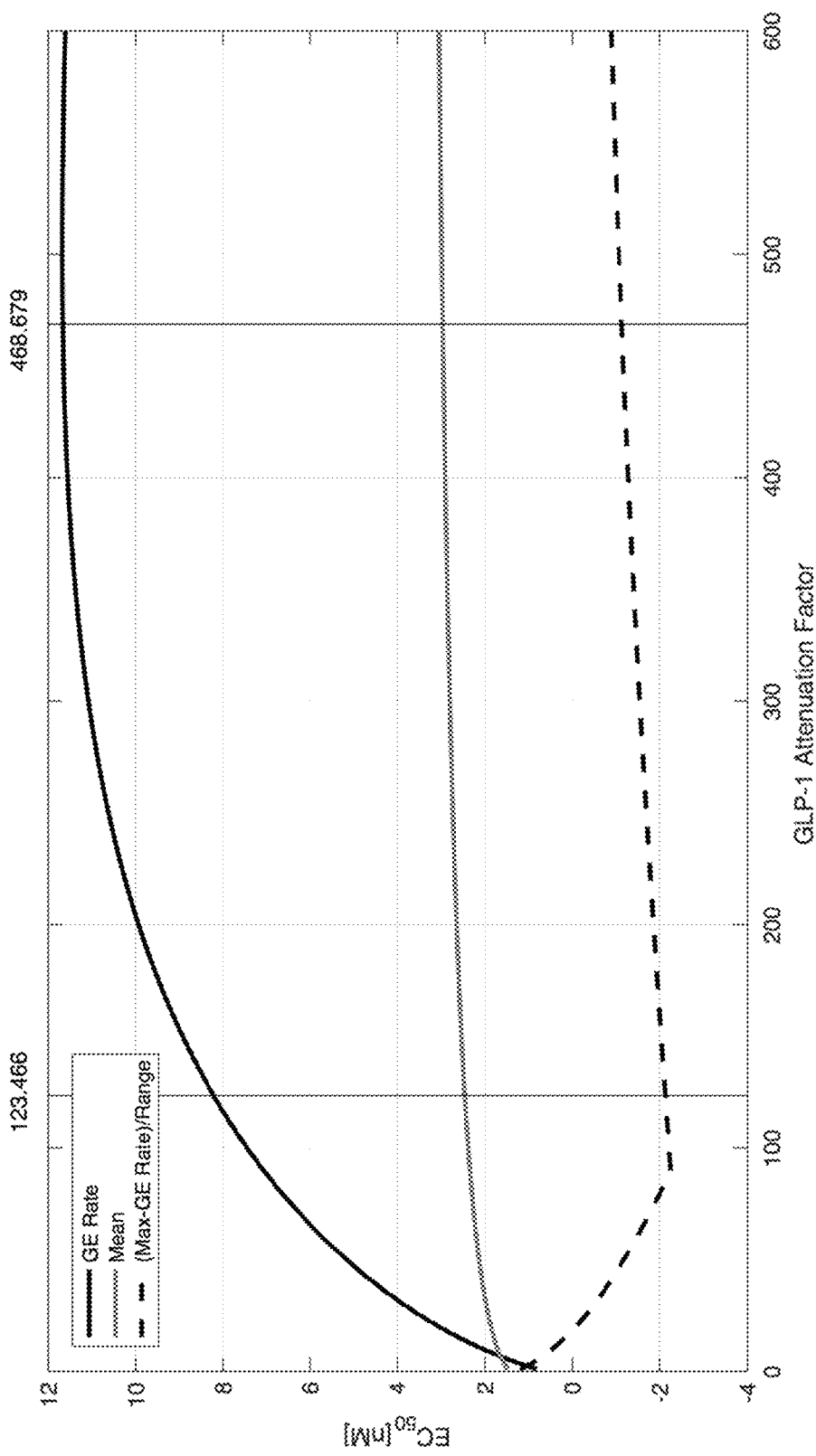

FIG. 3 is a graph showing EC50 of the adverse effect (gastric emptying (GE) rate) and pharmacodynamics (HbA1c, Triglycerides, Fatty Acids, Non-HDL, Adipose Mass) depending on GLP-1 attenuation factor (3-months simulation):

For GLP-1 attenuation factors greater than 18.268 (can be rounded to 18), EC50 of GLP-1-mediated gastrointestinal adverse effect (gastric emptying; GE-Rate) was greater than EC50 of pharmacodynamic effects (i.e., HbA1c, Adipose Mass, Non-HDL, Fatty Acids, Triglycerides);

Maximal distance between maximum of pharmacodynamics (HbA1c) and adverse effect (GE-Rate) normalized by spreading of FGF21- (lipids) and GLP-1-mediated effects (HbA1c) was 123.466; i.e. at 123.466 (can be rounded to 123), there is a maximal distance between maximum of pharmacodynamics effects (HbA1c) and adverse effect (GE-Rate) at a minimum distance between GLP-1-mediated effects (HbA1c) and mean FGF21-mediated effects (i.e., Adipose Mass, Non-HDL, Fatty Acids, Triglycerides) (see FIG. 4);

Maximal distance between maximum of pharmacodynamics (HbA1c) and adverse effect (GE-Rate) was 313.214 (can be rounded to 313);

Maximal distance between mean pharmacodynamics (i.e., HbA1c, Adipose Mass, Non-HDL, Fatty Acids, Triglycerides) and adverse effect (GE-Rate) was 468.679 (see FIG. 4; can be rounded to 469);

Maximum of gastric emptying rate at 500.686 (can be rounded to 501)

(all: vertical lines).

FIG. 4 is a graph showing EC50 of gastric emptying (GE) rate and mean pharmacodynamic effects (i.e., HbA1c, Triglycerides, Fatty Acids, Non-HDL, Adipose Mass) depending on GLP-1 attenuation factor (3-months simulation):

Maximal distance between mean pharmacodynamics (i.e. HbA1c, Adipose Mass, Non-HDL, Fatty Acids, Triglycerides) and adverse effect (GE-Rate) was 468.679 (right vertical line; can be rounded to 469);

Maximal distance between maximum of pharmacodynamics (HbA1c) and adverse effect (GE-Rate) normalized by spreading of FGF21- (lipids) and GLP-1-mediated effects (HbA1c) was 123.466 (left vertical line; can be rounded to 123). The curve "(Max-GE Rate)/Range" represents the ratio between the maximum distance between HbA1c and GE-Rate and the minimum distance between HbA1c and mean FGF21-mediated effects (i.e., Adipose Mass, Non-HDL, Fatty Acids, Triglycerides). At the minimum of the "(Max-GE Rate)/Range" curve (i.e. at 123.466), there is a maximal distance between maximum of pharmacodynamics effects (HbA1c) and adverse effect (GE-Rate) at a minimum distance between GLP-1-mediated effects (HbA1c) and FGF21-mediated effects (i.e., Adipose Mass, Non-HDL, Fatty Acids, Triglycerides).

Figure 5A:
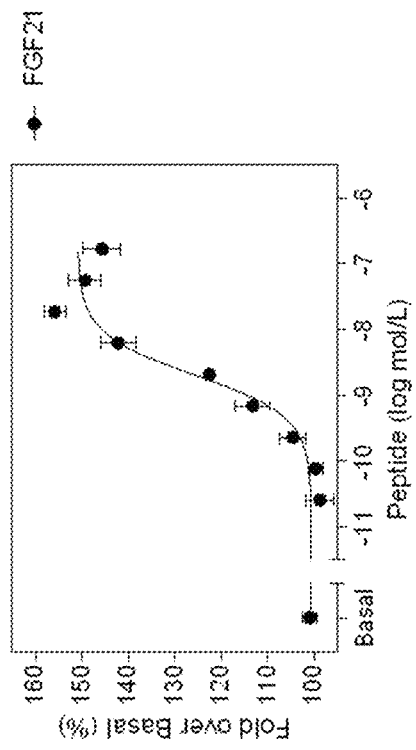
Figure 5B:
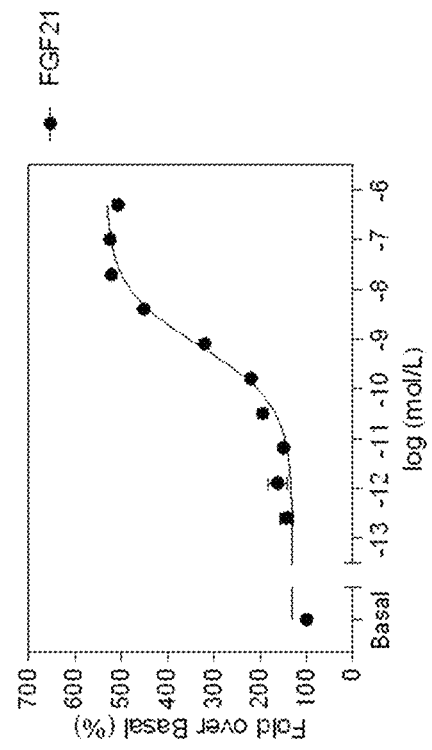

FIGS. 5A-5B show dose-response curves of FGFR auto-phosphorylation (FIG. 5A) or ERK1/2-phosphorylation (FIG. 5B) in CHO cells overexpressing human FGFR1c and beta-klotho after stimulus with mature human FGF21 (SEQ ID NO: 2) measured via In-Cell Western.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, certain elements of the present invention will be described. These elements may be listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

The terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (Sambrook, J. et al. (2001) Molecular Cloning: A Laboratory Manual, 3rd Ed., Cold Spring Harbor Laboratory Press, Cold Spring Harbor, N.Y.).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

By using a systems pharmacology approach that integrated key components of GLP-1 receptor signaling and FGF21 production and action in the context of diabetic pathophysiology, the inventors succeeded in determining the optimal GLP-1R agonist/FGF21 compound activity ratio in order to achieve the beneficial effects of both active agents (e.g., in terms of body weight, lipids, glycemic control) while avoiding potential adverse effects (e.g., nausea and vomiting).

The term "combination", as used herein, is meant to include means that allow to apply the combination comprising the FGF21 compound and the GLP-1R agonist either by separate administration of the FGF21 compound and the GLP-1R agonist to the patient or in the form of combination products in which the FGF21 compound and the GLP-1R agonist are present, e.g., in one pharmaceutical composition or in the form of a fusion molecule/protein. When administered separately, administration may occur simultaneously or sequentially, in any order. The amount of the FGF21 compound and the GLP-1R agonist as well as the relative timings of administration will be selected in order to achieve the desired combined therapeutic effect. The administration of the combination may be concomitantly in: (1) a unitary pharmaceutical composition including all active pharmaceutical ingredients; or (2) separate pharmaceutical compositions each including at least one of the active pharmaceutical ingredients. Alternatively, the combination may be administered separately in a sequential manner wherein one treatment agent is administered first and the other second or vice versa. Such sequential administration may be close in time or remote in time. In one embodiment, the combination is provided in the form of a kit, e.g., a kit as defined herein.

The term "fibroblast growth factor 21" or "FGF21", as used herein, refers to any FGF21 protein known in the art and particularly refers to human FGF21. In one embodiment, human FGF21 has the amino acid sequence of SEQ ID NO: 1.

The term "FGF21 compound", as used herein, generally refers to a compound having FGF21 activity.

In one embodiment, the FGF21 compound is a peptidic compound, i.e., a peptide or protein.

The term "peptide", as used herein, refers to a polymeric form of amino acids of any length, for example, comprising two or more, or 3 or more, or 4 or more, or 6 or more, or 8 or more, or 9 or more, or 10 or more, or 13 or more, or 16 or more, or 21 or more amino acids joined covalently by peptide bonds. A peptide may, for example, consist of up to 100 amino acids. The term "polypeptide" refers to large peptides, preferably to peptides with more than 100 amino acid residues. The terms "polypeptide" and "protein" are used interchangeably herein.

In one embodiment, the FGF21 compound is native FGF21 or an FGF21 variant having at least 80% or at least 90% or at least 91% or at least 92% or at least 93% or at least 94% or at least 95% or at least 96% or at least 97% or at least 98% amino acid sequence identity to the amino acid sequence of native FGF21.

The term "native FGF21", as used herein, refers to a naturally occurring FGF21, e.g., human wild-type FGF21 with the amino acid sequence of SEQ ID NO: 1 (also referred to as "full-length human wild-type FGF21"). The term "native FGF21", as used herein, also includes mature FGF21, i.e., a naturally occurring FGF21 lacking the natural signal sequence (also referred to as signal peptide). In one embodiment, the native FGF21 is mature human wild-type FGF21 lacking amino acids 1 to 28 (M1 to A28) of SEQ ID NO: 1, and is represented by SEQ ID NO: 2.

"Sequence identity" between two amino acid sequences indicates the percentage of amino acids that are identical between the sequences. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

An FGF21 variant may be based on the deletion, addition and/or substitution of at least one amino acid residue in/to the native FGF21 (e.g., of SEQ ID NO: 1 or 2).

Such deletion, addition and/or substitution may contribute to an increased stability, e.g., proteolytic and/or thermal stability, of the variant as compared to the native FGF21 (e.g., SEQ ID NO: 1 or 2). This may be achieved, for example, by the prevention of protease cleavage at or in proximity to the substituted amino acid or by formation of one or more additional disulfide bridges.

The term "amino acid" or "amino acid residue", as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

When used in connection with amino acids, the term "naturally occurring" refers to the 20 conventional amino acids (i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y)), as well as selenocysteine, pyrrolysine (PYL), and pyrroline-carboxylysine (PCL).

The term "unnatural amino acid", as used herein, is meant to refer to amino acids that are not naturally encoded or found in the genetic code of any organism. They may, for example, be purely synthetic compounds. Examples of unnatural amino acids include, but are not limited to, hydroxyproline, gamma-carboxyglutamate, 0-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, D-ornithine, D-arginine, p-aminophenylalanine, pentylglycine, pipecolic acid and thioproline.

The term "amino acid analogue", as used herein, refers to compounds that have the same basic chemical structure as a naturally occurring amino acid. Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(betamethylester), N-ethylglycine, alanine carboxamide, homoserine, norleucine and methionine methyl sulfonium.

The term "amino acid mimetics", as used herein, refers to chemical compounds that have a structure that is different from the general chemical structure of an amino acid, but function in a manner similar to a naturally occurring amino acid.

In some embodiments, the variant comprises at least one additional amino acid at its N-terminus. In one embodiment, the at least one additional amino acid is selected from naturally occurring amino acids except proline, unnatural amino acids, amino acid analogues and amino acid mimetics. In one embodiment, the at least one additional amino acid is selected from the group consisting of G, A, N and C. In a particular embodiment, the at least one additional amino acid is G.

Suitable FGF21 variants for use in the present invention are described, e.g., in PCT/EP2016/079551, which is incorporated herein by reference.

In one embodiment, the FGF21 compound is an FGF21 variant comprising or consisting of an amino acid sequence selected from the group consisting of SEQ ID NOs: 3, 4, 5 and 6.

The FGF21 compound comprised in the combinations, pharmaceutical compositions and fusion molecules of the invention exhibits FGF21 activity which is the same or substantially the same as the FGF21 activity of native FGF21 (e.g., SEQ ID NO: 2). In one embodiment, the FGF21 activity refers to the FGF21 activity of the FGF21 compound when it is not comprised in (is not a component of) a fusion molecule as defined herein and/or when it is not further modified (see below).

The term "substantially the same", as used herein, refers to an FGF21 activity which is in the range of 50 to 150% or 60 to 140% or 65 to 135% of the FGF21 activity of native FGF21 (e.g., SEQ ID NO: 2).

In one embodiment, the term "FGF21 activity" (or "FGF21 potency"), as used herein, refers to activation of the FGF21 receptor (FGFR, e.g., FGFR1c). In one embodiment, the FGF21 receptor is a human FGF21 receptor. In one embodiment, the term refers to the activity/potency in vitro. In another embodiment, the term refers to the activity/potency in vivo. In one embodiment, activation of the FGF21 receptor is determined by measuring FGF21 receptor autophosphorylation upon contact with the FGF21 compound in vitro. In one embodiment, FGF21 activity/potency is determined by using an In-Cell Western (ICW) assay. In one embodiment, the activity/potency is quantified by determining the EC50 value.

The term "In-Cell Western (ICW) assay", as used herein, refers to an immunocytochemical assay, more particularly a quantitative immunofluorescence assay, usually performed in microplates (e.g., in a 96- or 384-well format). It combines the specificity of Western blotting with the reproducibility and throughput of ELISA (see, for example, Aguilar H. N. et al. (2010) PLoS ONE 5(4): e9965). Appropriate ICW assay systems are commercially available (e.g., from LI-COR Biosciences, USA). In one embodiment, an anti-pFGFR and/or and anti-pERK is/are used in the ICW assay. In one embodiment, a pFGFR ICW assay is performed. In one embodiment, the ICW assay is performed essentially as described in Example 3.

In one embodiment, the FGF21 compound having an FGF21 activity which is the same or substantially the same as the FGF21 activity of native FGF21 may be defined in terms of its EC50 value of FGF21 receptor activation. For example, an FGF21 compound having an FGF21 activity in the range of 50 to 150% or 60 to 140% or 65 to 135% of the FGF21 activity of native FGF21 (e.g., SEQ ID NO: 2) may also be referred to herein as an FGF21 compound which activates the FGF21 receptor with an EC50 of 2.40 to 7.20 nmol/L or 2.88 to 6.72 nmol/L or 3.12 to 6.48 nmol/L, respectively, in a pFGFR ICW assay, e.g., as essentially described in Example 3. In one embodiment, the EC50 value is given as EC50±SD. In one embodiment, SD is the assay-dependent standard deviation. In one embodiment, the EC50 is 2.40±SD to 7.20±SD nmol/L or 2.88±SD to 6.72±SD nmol/L or 3.12±SD to 6.48±SD nmol/L, respectively, in a pFGFR ICW assay, e.g., as essentially described in Example 3. In one embodiment, SD is 1.8 nmol/L.

In accordance with the present invention, the FGF21 compound may be further modified, e.g., fused/conjugated to another entity/molecule, such as a polymer (e.g., PEG) or a peptide/polypeptide, such as human serum albumin (HSA) or an Fc region/domain of an immunoglobulin or a variant thereof, e.g., as described further below. In one embodiment, the FGF21 activity of the FGF21 compound referred to herein is the FGF21 activity of the FGF21 compound without such further modification, also referred to herein as "pure FGF21 compound".

The term "fused to", as used herein, refers, in particular, to genetic fusion, e.g., by recombinant DNA technology. The amino acid sequence of a (poly)peptide half-life extension module may be introduced at any position within the amino acid sequence of the variant, and may, for example, take the shape of a loop within the encoded protein structure, or it may be N-terminally or C-terminally fused.

The term "conjugated to", as used herein, refers, in particular, to chemical and/or enzymatic conjugation resulting in a stable covalent link between a (poly-)peptide and another molecule, e.g., the variant and the half-life extension module. Such conjugation may occur at the N- or C-terminus or at particular side chains of a (poly-)peptide, e.g., at lysine, cysteine, tyrosine or unnatural amino acid residues.

The term "GLP-1R agonist" (in short: "GLP-1RA"), as used herein, generally refers to a compound which binds to and activates the GLP-1 receptor, such as GLP-1 (as the primary GLP-1R agonist).

In one embodiment, the GLP-1R agonist is a peptidic compound, i.e., a peptide or protein. In another embodiment, the GLP-1R agonist is a small molecule, i.e., an organic compound with a molecular weight of less than 900 Da.

The GLP-1R agonist comprised in the combinations, pharmaceutical compositions and fusion molecules of the invention exhibits a GLP-1R agonistic activity which is reduced as compared to that of native GLP-1(7-36) as defined herein. Value "x" in the expression "x-fold reduced", as used herein, may be referred to herein as "attenuation factor" or "reduction factor". In one embodiment, the GLP-1R agonistic activity which is reduced as compared to that of native GLP-1(7-36) as defined herein is exhibited when the GLP-1R agonist is a component of a fusion molecule as defined herein.

The term "native GLP-1(7-36)", as used herein, refers to a peptide having the amino acid sequence of SEQ ID NO: 7, which, optionally, comprises an amide group at its C-terminus.

In one embodiment, the term "GLP-1R agonistic activity" (or "GLP-1R agonistic potency"), as used herein, refers to the activation of the GLP-1 receptor. In one embodiment, the term refers to the agonistic activity/potency in vitro. In another embodiment, the term refers to the agonistic activity/potency in vivo. In one embodiment, activation of the GLP-1 receptor is determined by measuring the cAMP response of cells stably expressing GLP-1 receptor upon contact with the agonist in vitro. In one embodiment, the cells are from a HEK-293 cell line. In one embodiment, the GLP-1 receptor is human GLP-1 receptor. In one embodiment, activation of the GLP-1 receptor is determined essentially as described in Example 4. In one embodiment, the activity/potency is quantified by determining the EC50 value.

In one embodiment, the GLP-1R agonist having a GLP-1R agonistic activity which is reduced as compared to the GLP-1R agonistic activity of native GLP-1(7-36) may be defined in terms of its EC50 value of GLP-1 receptor activation, e.g., as indicated in Table 4. For example, a GLP-1R agonist having a GLP-1R agonistic activity which is 9- to 531-fold reduced as compared to the GLP-1R agonistic activity of native GLP-1(7-36) may also be referred to herein as a GLP-1R agonist which activates the GLP-1 receptor with an EC50 of 6.93 to 408.87 pmol/L, etc. In one embodiment, the EC50 value is determined as described above. In one embodiment, the EC50 value is given as EC50±SD. In one embodiment, SD is the assay-dependent standard deviation.

Suitable GLP-1R agonists having a GLP-1R agonistic activity which is reduced as compared to that of native GLP-1(7-36) can be identified by the assays described herein for determining GLP-1R agonistic activity, e.g., an assay as described in Example 4 or in Xiao et al. (2001) Biochemistry. 40(9): 2860-9 or Gault et al. (2013) J Biol Chem. 288(49): 35581-91, e.g., analysis of GLP-1R agonist-induced production of cytosolic cAMP, β-cell preserving action (apoptosis), or glucose-stimulated insulin secretion (GSIS) etc. They can be identified, for example, by producing variants of known peptidic GLP-1R agonists, such as native GLP-1(7-36), e.g., by random or site-directed mutagenesis or chemical synthesis (see, e.g., Example 5), and subsequent determination of their GLP-1R agonistic activity as described herein using native GLP-1(7-36) as control. Alternatively, they can be identified by screening of small molecule libraries in terms of GLP-1R agonistic activity using native GLP-1(7-36) as control. All of these assays can be performed in the form of high-throughput assays.

A variant of a known peptidic GLP-1R agonist (e.g., native GLP-1(7-36)) may be based on the deletion, addition and/or substitution of at least one amino acid residue in/to the amino acid sequence of the known peptidic GLP-1R agonist.

In one embodiment, the variant comprises up to 15, 14, 13, 12, 11, 10, 9, 8, 7, 6 or 5 substitutions of amino acid residues.

In one embodiment, the GLP-1R agonist is a variant of native GLP-1(7-36) comprising up to 15, 14, 13, 12, 11, 10, 9, 8, 7, 6 or 5 substitutions of amino acid residues in the sequence of native GLP-1(7-36). In one embodiment, the substitutions are selected from the group comprising or consisting of A8G, V16L, V16K, S18K, S18I, Y19Q, L20M, E21D, G22E, Q23E, A24R, A25V, K26R, K26Q, E27L, A30E, V33K, V33L, V33E, K34N, K34A, G35T and R36G and/or substitutions as listed in Table 5 (see description of SEQ ID NOs: 8 to 20).

In some embodiments, the variant comprises at least one additional amino acid residue at its N-terminus. In one embodiment, the at least one additional amino acid residue is selected from naturally occurring amino acids except proline, unnatural amino acids, amino acid analogues and amino acid mimetics. In one embodiment, the at least one additional amino acid residue is selected from the group consisting of G, A, N and C. In a particular embodiment, the at least one additional amino acid residue is (a single) G.

In some embodiments, the variant comprises a peptide extension at its C-terminus. The peptide extension may, for example, consist of up to 12, 11 or 10 amino acid residues. In one embodiment, the peptide extension has an amino acid sequence selected from the group consisting of PSSGAPPPS (SEQ ID NO: 38), PVSGAPPPS (SEQ ID NO: 39), PSSGEPPPES (SEQ ID NO: 40), PSSGEPPPE (SEQ ID NO: 41), PKKQRLS (SEQ ID NO: 42) and PKKIRYS (SEQ ID NO: 43).

In one embodiment, the GLP-1R agonist having a GLP-1R agonistic activity which is reduced as compared to that of native GLP-1(7-36) as defined herein comprises or consists of the amino acid sequence

```
                                              (SEQ ID NO: 37)
H-G-E-G-T-F-T-S-D-X10-S-X12-Q-X14-X15-E-E-X18-V-

X20-X21-F-I-E-W-L-X27-X28-X29-X30,
``` wherein
$X_{10}$ is any amino acid, e.g., L or K;
$X_{12}$ is any amino acid, e.g. K or I;
$X_{14}$ is any amino acid, e.g. L or M;
$X_{15}$ is any amino acid, e.g. E or D;
$X_{18}$ is any amino acid, e.g. A or R;
$X_{20}$ is any amino acid, e.g. R or Q;
$X_{21}$ is any amino acid, e.g. L or E;
$X_{27}$ is any amino acid, e.g., L, E, K or V;
$X_{28}$ is any amino acid, e.g., A, N or K;
$X_{29}$ is any amino acid, e.g. T or G;
$X_{30}$ is any amino acid, e.g. G or R;
wherein, optionally, the amino acid sequence comprises at least one additional amino acid residue at its N-terminus; and wherein, optionally, the amino acid sequence comprises a peptide extension consisting of up to 12, 11 or 10 amino acid residues at its C-terminus.

In one embodiment, $X_{27}$ is L, E or V, e.g., L. In one embodiment, $X_{28}$ is A or K, e.g., A.

In one embodiment, the at least one additional amino acid residue is selected from the group consisting of G, A, N and C. In a particular embodiment, the at least one additional amino acid residue is (a single) G.

In one embodiment, the peptide extension has an amino acid sequence selected from the group consisting of PSS-GAPPPS (SEQ ID NO: 38), PVSGAPPPS (SEQ ID NO: 39), PSSGEPPPES (SEQ ID NO: 40), PSSGEPPPE (SEQ ID NO: 41), PKKQRLS (SEQ ID NO: 42) and PKKIRYS (SEQ ID NO: 43).

Modifications as disclosed herein, such as introduction of G at the N-terminus or $X_{12}$=I, lead to suitable reduction of GLP-1R agonistic activity.

In one embodiment, the GLP-1R agonist having a GLP-1R agonistic activity which is reduced as compared to that of native GLP-1(7-36) as defined herein comprises or consists of an amino acid sequence selected from the group consisting of SEQ ID NOs: 9, 10, 12, 14, 15, 16, 17, 19 and 20.

In accordance with the present invention, the GLP-1R agonist may be further modified, e.g. as described above in connection with the FGF21 compound.

A pharmaceutical composition in accordance with the present invention comprises one or more carriers and/or excipients, all of which are pharmaceutically acceptable. The term "pharmaceutically acceptable", as used herein, refers to the non-toxicity of a material which, preferably, does not interact with the action of the active agent of the pharmaceutical composition.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a subject.

Possible carrier substances for parenteral administration are, e.g., sterile water, Ringer's solution, Lactated Ringer's solution, physiological saline, bacteriostatic saline (e.g., saline containing 0.9% benzyl alcohol), phosphate-buffered saline (PBS), Hank's solution, polyalkylene glycols, hydrogenated naphthalenes and, in particular, biocompatible lactide polymers, lactide/glycolide copolymers or polyoxyethylene/polyoxy-propylene copolymers.

The term "excipient", as used herein, is intended to include all substances which may be present in a pharmaceutical composition and which are not active ingredients, such as salts, binders (e.g., lactose, dextrose, sucrose, trehalose, sorbitol, mannitol), fillers, lubricants, thickeners, surface active agents, preservatives, emulsifiers, buffer substances, flavoring agents, or colorants.

Salts, which are not pharmaceutically acceptable, may be used for preparing pharmaceutically acceptable salts and are included in the invention. Pharmaceutically acceptable salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts. Salts may be added to adjust the ionic strength or tonicity.

Suitable preservatives for use in a pharmaceutical composition include antioxidants, citric acid, sodium citrate, benzalkonium chloride, chlorobutanol, cysteine, methionine, parabens, thimerosal, phenol, cresol, and mixtures thereof.

Suitable buffer substances for use in a pharmaceutical composition include acetic acid in a salt, citric acid in a salt, boric acid in a salt, phosphoric acid in a salt, and tris (hydroxymethyl)aminomethane (Tris, THAM, trometamol).

A pharmaceutical composition in accordance with the present invention is preferably sterile. Pharmaceutical compositions may be provided in a uniform dosage form and may be prepared in a manner known per se. A pharmaceutical composition may, e.g., be in the form of a solution or suspension.

The pharmaceutical composition may also be formulated as a stable lyophilized product that is reconstituted with an appropriate diluent, which, optionally, comprises one or more excipients as defined above.

A pharmaceutical composition in accordance with the present invention may further comprise at least one other active pharmaceutical ingredient.

The term "active pharmaceutical ingredient" (API), us used herein, includes any pharmaceutically active chemical or biological compound and any pharmaceutically acceptable salt thereof and any mixture thereof, that provides some pharmacologic effect and is used for treating or preventing a condition, e.g., a disease or disorder as defined herein. Exemplary pharmaceutically acceptable salts include hydrochloric, sulfuric, nitric, phosphoric, hydrobromic, maleric, malic, ascorbic, citric, tartaric, pamoic, lauric, stearic, palmitic, oleic, myristic, lauryl sulfuric, naphthalinesulfonic, linoleic, linolenic acid, and the like. As used herein, the terms "active pharmaceutical ingredient", "active agent", "active ingredient", "active substance", "therapeutically active compound" and "drug" are meant to be synonyms, i.e., have identical meaning.

In accordance with the present invention, an active pharmaceutical ingredient is optionally selected from:

all drugs mentioned in the Rote Liste 2014, e.g. all antidiabetics mentioned in the Rote Liste 2014, chapter 12, all weight-reducing agents or appetite suppressants mentioned in the Rote Liste 2014, chapter 06, all lipid-lowering agents mentioned in the Rote Liste 2014, chapter 58, all antihypertensives mentioned in the Rote Liste 2014 chapter 17, all nephroprotectives mentioned in the Rote Liste, or all diuretics mentioned in the Rote Liste 2014, chapter 36;

insulin and insulin derivatives, for example: insulin glargine (e.g. Lantue®), higher than 100U/mL concentrated insulin glargine, e.g. 270-330U/mL of insulin glargine or 300 U/mL of insulin glargine (as disclosed in EP 2387989), insulin glulisine (e.g. Apidra®), insulin detemir (e.g. Levemir®), insulin lispro (e.g. Humalog®, Liprolog®), insulin degludec (e.g. Degludec-Plus®, IdegLira (NN9068)), insulin aspart and aspart formulations (e.g.) NovoLog®, basal insulin and analogues (e.g. LY2605541, LY2963016, NN1436), PEGylated insulin lispro (e.g. LY-275585), long-acting insulins (e.g. NN1436, Insumera (PE0139), AB-101, AB-102, Sensulin LLC), intermediate-acting insulins (e.g. Humulin® N, Novolin® N), fast-acting and short-acting insulins (e.g. Humulin® R, Novolin® R, Linjeta® (VIAject®), PH20 insulin, NN1218, HinsBet®), premixed insulins, SuliXen®, NN1045, insulin plus Symlin®, PE-0139, ACP-002 hydrogel insulin, and oral, inhalable, transdermal and buccal or sublingual insulins (e.g. Exubera®, Nasulin®, Afrezza®, insulin tregopil, TPM-02 insulin, Capsulin®, Cobalamin® oral insulin, ORMD-0801, Oshadi oral insulin, NN1953, NN1954, NN1956, VIAtab®). also suitable are those insulin derivatives which are bonded to albumin or another protein by a bifunctional linker;

glucagon-like-peptide 1 (GLP-1), GLP-1 analogues, and GLP-1 receptor agonists, for example: GLP-1(7-37), GLP-1(7-36)amide, lixisenatide (e.g. Lyxumia®), exenatide (e.g. exendin-4, rExendin-4, Byetta®, Bydureon®, exenatide NexP), exenatide-LAR, liraglutide (e.g. Victoza®), semaglutide, taspoglutide, albiglutide, dulaglutide, albugon, oxyntomodulin, geniproside, ACP-003, CJC-1131, CJC-1134-PC, GSK-2374697, PB-1023, TTP-054, langlenatide (HM-112600), CM-3, GLP-1 Eligen, AB-201, ORMD-0901, NN9924, NN9926, NN9927, Nodexen, Viador-GLP-1, CVX-096, ZYOG-1, ZYD-1, ZP-3022, CAM-2036, DA-3091, DA-15864, ARI-2651, ARI-2255, exenatide-XTEN (VRS-859), exenatide-XTEN+Glucagon-XTEN (VRS-859+AMX-808) and polymer-bound GLP-1 and GLP-1 analogues;

dual GLP-1/GIP agonists (e.g. RG-7697 (MAR-701), MAR-709, BHM081, BHM089, BHM098); dual GLP-1/glucagon receptor agonists (e.g. BHM-034, OAP-189 (PF-05212389, TKS-1225), TT-401/402, ZP2929, LAPS-HMOXM25, MOD-6030);

dual GLP-1/gastrin agonists (e.g. ZP-3022);

gastrointestinal peptides such as peptide YY 3-36 (PYY3-36) or analogues thereof and pancreatic polypeptide (PP) or analogues thereof;

glucagon receptor agonists or antagonists, glucose-dependent insulinotropic polypeptide (GIP) receptor agonists or antagonists, ghrelin antagonists or inverse agonists, xenin and analogues thereof;

dipeptidyl peptidase-IV (DPP-4) inhibitors, for example: alogliptin (e.g. Nesina®, Kazano®), linagliptin (e.g. Ondero®, Trajenta®, Tradjenta®, Trayenta®), saxagliptin (e.g. Onglyza®, Komboglyze XR®), sitagliptin (e.g. Januvia®, Xelevia®, Tesavel®, Janumet®, Velmetia®, Juvisync®, Janumet XR®), anagliptin, teneligliptin (e.g. Tenelia®), trelagliptin, vildagliptin (e.g. Galvus®, Galvumet®), gemigliptin, omarigliptin, evogliptin, dutogliptin, DA-1229, MK-3102, KM-223, KRP-104, PBL-1427, Pinoxacin hydrochloride, and Ari-2243;

sodium-dependent glucose transporter 2 (SGLT-2) inhibitors, for example: canagliflozin, dapagliflozin, remogliflozin, remogliflozin etabonate, sergliflozin, empagliflozin, ipragliflozin, tofogliflozin, luseogliflozin, ertugliflozin, EGT-0001442, LIK-066, SBM-TFC-039, and KGA-3235 (DSP-3235);

dual inhibitors of SGLT-2 and SGLT-1 (e.g. LX-4211, LIK066).

SGLT-1 inhibitors (e.g. LX-2761, KGA-3235) or SGLT-1 inhibitors in combination with anti-obesity drugs such as ileal bile acid transfer (IBAT) inhibitors (e.g. GSK-1614235+GSK-2330672);

biguanides (e.g. metformin, buformin, phenformin);

thiazolidinediones (e.g. pioglitazone, rosiglitazone), glitazone analogues (e.g. lobeglitazone);

peroxisome proliferator-activated receptors (PPAR−)(alpha, gamma or alpha/gamma) agonists or modulators (e.g. saroglitazar (e.g. Lipaglyn®), GFT-505), or PPAR gamma partial agonists (e.g. Int-131);

sulfonylureas (e.g. tolbutamide, glibenclamide, glimepiride, Amaryl®, glipizide) and meglitinides (e.g. nateglinide, repaglinide, mitiglinide);

alpha-glucosidase inhibitors (e.g. acarbose, miglitol, voglibose);

amylin and amylin analogues (e.g. pramlintide, Symlin®);

G-protein coupled receptor 119 (GPR119) agonists (e.g. GSK-1292263, PSN-821, MBX-2982, APD-597, ARRY-981, ZYG-19, DS-8500, HM-47000, YH-Chem1);

GPR40 agonists (e.g. TUG-424, P-1736, P-11187, JTT-851, GW9508, CNX-011-67, AM-1638, AM-5262);

GPR120 agonists and GPR142 agonists;

systemic or low-absorbable TGR5 (GPBAR1=G-protein-coupled bile acid receptor 1) agonists (e.g. INT-777, XL-475, SB756050);

diabetes immunotherapeutics, for example: oral C—C chemokine receptor type 2 (CCR-2) antagonists (e.g. CCX-140, JNJ-41443532), interleukin 1 beta (IL-1β) antagonists (e.g. AC-201), or oral monoclonal antibodies (MoA) (e.g. methalozamide, VVP808, PAZ-320, P-1736, PF-05175157, PF-04937319);

anti-inflammatory agents for the treatment of the metabolic syndrome and diabetes, for example: nuclear factor kappa B inhibitors (e.g. Triolex®);

adenosine monophosphate-activated protein kinase (AMPK) stimulants, for example: Imeglimin (PXL-008), Debio-0930 (MT-63-78), R-118;

inhibitors of 11-beta-hydroxysteroid dehydrogenase 1 (11-beta-HSD-1) (e.g. LY2523199, BMS770767, RG-4929, BMS816336, AZD-8329, HSD-016, BI-135585);

activators of glucokinase (e.g. PF-04991532, TTP-399 (GK1-399), GKM-001 (ADV-1002401), ARRY-403 (AMG-151), TAK-329, TMG-123, ZYGK1);

inhibitors of diacylglycerol O-acyltransferase (DGAT) (e.g. pradigastat (LCQ-908)), inhibitors of protein tyrosine phosphatase 1 (e.g. trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase;

modulators of glucose transporter-4, somatostatin receptor 3 agonists (e.g. MK-4256);

one or more lipid lowering agents are also suitable as combination partners, for example: 3-hydroxy-3-methylglutaryl-coenzym-A-reductase (HMG-CoA-reductase) inhibitors such as simvastatin (e.g. Zocor®, Inegy®, Simcor®), atorvastatin (e.g. Sods®, Caduet®), rosuvastatin (e.g. Crestor®), pravastatin (e.g. Lipostat®, Selipran®), fluvastatin (e.g. Lescol®), pitavastatin (e.g. Livazo®, Livalo®), lovastatin (e.g. Mevacor®, Advicor®), mevastatin (e.g. Compactin®), rivastatin, cerivastatin (Lipobay®), fibrates such as bezafibrate (e.g. Cedur® retard), ciprofibrate (e.g. Hyperlipen®), fenofibrate (e.g. Antara®, Lipofen®, Lipanthyl®), gemfibrozil (e.g. Lopid®, Gevilon®), etofibrate, simfibrate, ronifibrate, clinofibrate, clofibride, nicotinic acid and derivatives thereof (e.g. niacin, including slow release formulations of niacin), nicotinic acid receptor 1 agonists (e.g. GSK-256073), PPAR-delta agonists, acetyl-CoA-acetyltransferase (ACAT) inhibitors (e.g. avasimibe), cholesterol absorption inhibitors (e.g. ezetimibe, Ezetrol®, Zetia®, Liptruzet®, Vytorin®, S-556971), bile acid-binding substances (e.g. cholestyramine, colesevelam), ileal bile acid transport (IBAT) inhibitors (e.g. GSK-2330672, LUM-002), microsomal triglyceride transfer protein (MTP) inhibitors (e.g. lomitapide (AEGR-733), SLx-4090, granotapide), modulators of proprotein convertase subtilisin/kexin type 9 (PCSK9) (e.g. alirocumab (REGN727/SAR236553), AMG-145, LGT-209, PF-04950615, MPSK3169A, LY3015014, ALD-306, ALN-PCS, BMS-962476, SPC5001, ISIS-394814, 1B20, LGT-210, 1D05, BMS-PCSK9Rx-2, SX-PCK9, RG7652), LDL receptor up-regulators, for example liver selective thyroid hormone receptor beta agonists (e.g. eprotirome (KB-2115), MB07811, sobetirome (QRX-431), VIA-3196, ZYT1), HDL-raising compounds such as: cholesteryl ester transfer protein (CETP) inhibitors (e.g. anacetrapib (MK0859), dalcetrapib, evacetrapib, JTT-302, DRL-17822, TA-8995, R-1658, LY-2484595, DS-1442), or dual CETP/PCSK9 inhibitors (e.g. K-312), ATP-binding cassette (ABC1) regulators, lipid metabolism modulators (e.g. BMS-823778, TAP-301, DRL-21994, DRL-21995), phospholipase A2 (PLA2) inhibitors (e.g. darapladib, Tyrisa®, varespladib, rilapladib), ApoA-I enhancers (e.g. RVX-208, CER-001, MDCO-216, CSL-112), cholesterol synthesis inhibitors (e.g. ETC-1002), lipid metabolism modulators (e.g. BMS-823778, TAP-301, DRL-21994, DRL-21995) and omega-3 fatty acids and derivatives thereof (e.g. icosapent ethyl (AMR101), Epanova®, AKR-063, NKPL-66, PRC-4016, CAT-2003);

bromocriptine (e.g. Cycloset®, Parlodel®), phentermine and phentermine formulations or combinations (e.g. Adipex-P, Ionamin, Qsymia®), benzphetamine (e.g. Didrex®), diethylpropion (e.g. Tenuate®), phendimetrazin (e.g. Adipost®, Bontril®), bupropion and combinations (e.g. Zyban®, Wellbutrin XL®, Contrave®, Empatic®), sibutramine (e.g. Reductil®, Meridia®), topiramat (e.g. Topamax®), zonisamid (e.g. Zonegran®), tesofensine, opioid antagonists such as naltrexone (e.g. Naltrexin®, naltrexone+bupropion), cannabinoid receptor 1 (CB1) antagonists (e.g. TM-38837), melanin-concentrating hormone (MCH-1) antagonists (e.g. BMS-830216, ALB-127158(a)), MC4 receptor agonists and partial agonists (e.g. AZD-2820, RM-493), neuropeptide Y5 (NPY5) or NPY2 antagonists (e.g. velneperit, S-234462), NPY4 agonists (e.g. PP-1420), beta-3-adrenergic receptor agonists, leptin or leptin mimetics, agonists of the 5-hydroxytryptamine 2c (5HT2c) receptor (e.g. lorcaserin, Belviq®), pramlintide/metreleptin, lipase inhibitors such as cetilistat (e.g. Cametor®), orlistat (e.g. Xenical®, Calobalin®), angiogenesis inhibitors (e.g. ALS-L1023), betahistidin and histamine H3 antagonists (e.g. HPP-404), AgRP (agouti related protein) inhibitors (e.g. TTP-435), serotonin re-uptake inhibitors such as fluoxetine (e.g. Fluctine®), duloxetine (e.g. Cymbalta®), dual or triple monoamine uptake inhibitors (dopamine, norepinephrine and serotonin re-uptake) such as sertraline (e.g. Zoloft®), tesofensine, methionine aminopeptidase 2 (MetAP2) inhibitors (e.g. beloranib), and antisense oligonucleotides against production of fibroblast growth factor receptor 4 (FGFR4) (e.g. ISIS-FGFR4Rx) or prohibitin targeting peptide-1 (e.g. Adipotide®);

nitric oxide donors, AT1 antagonists or angiotensin II (AT2) receptor antagonists such as telmisartan (e.g. Kinzal®, Micardis®), candesartan (e.g. Atacand®, Blopress®), valsartan (e.g. Diovan®, Co-Diovan®), losartan (e.g. Cosaar®), eprosartan (e.g. Teveten®), irbesartan (e.g. Aprovel®, CoAprovel®), olmesartan (e.g. Votum®, Olmetec®), tasosartan, azilsartan (e.g. Edarbi®), dual angiotensin receptor blockers (dual ARBs), angiotensin converting enzyme (ACE) inhibitors, ACE-2 activators, renin inhibitors, prorenin inhibitors, endothelin converting enzyme (ECE) inhibitors, endothelin receptor (ET1/ETA) blockers, endothelin antagonists, diuretics, aldosterone antagonists, aldosterone synthase inhibitors, alpha-blockers, antagonists of the alpha-2 adrenergic receptor, beta-blockers, mixed alpha-/beta-blockers, calcium antagonists, calcium channel blockers (CCBs), nasal formulations of the calcium channel blocker diltiazem (e.g. CP-404), dual mineralocorticoid/CCBs, centrally acting antihypertensives, inhibitors of neutral endopeptidase, aminopeptidase-A inhibitors, vasopeptide inhibitors, dual vasopeptide inhibitors such as neprilysin-ACE inhibitors or neprilysin-ECE inhibitors, dual-acting AT receptor-neprilysin inhibitors, dual AT1/ETA antagonists, advanced glycation end-product (AGE) breakers, recombinant renalase, blood pressure vaccines such as anti-RAAS (renin-angiotensin-aldosteron-system) vaccines, AT1- or AT2-vaccines, drugs based on hypertension pharmacogenomics such as modulators of genetic polymorphisms with antihypertensive response, thrombocyte aggregation inhibitors, and others or combinations thereof are suitable.

The term "fusion molecule" generally refers to molecules created by joining, in particular covalently linking, two or more distinct molecules (e.g., proteins and/or peptides) resulting in a single molecule with functional properties derived from each of the original molecules. In the case of proteins and/or peptides, the fusion molecule is referred to as "fusion protein". Fusion molecules may be generated by genetic fusion (e.g., by recombinant DNA technology) or by chemical and/or enzymatic conjugation. The two or more distinct molecules may also be linked by suitable linker molecules, e.g., peptide linkers or non-peptidic polymers, such as polyethylene glycol (PEG).

In general, peptide linkers are designed to provide flexibility and protease resistance. In one embodiment, the peptide linker has a length of 1 to 30, 1 to 25 or 1 to 20 amino acid residues. In one embodiment, the peptide linker comprises at least 5 amino acid residues. In one embodiment, the peptide linker is a glycine-serine-rich linker, wherein at least 50%, preferably at least 60%, more preferably at least 70%, more preferably at least 80%, even more preferably at least 85% of the amino acids are a glycine or serine residue, respectively. In one embodiment, the peptide linker comprises an alanine residue at its C-terminus. In another embodiment, the amino acids are selected from glycine and serine, i.e., the peptide linker is exclusively composed of glycine and serine (referred to as a glycine-serine linker). In one embodiment, the peptide linker comprises or consists of the amino acid sequence of SEQ ID NO: 22 or SEQ ID NO: 23. Peptide linkers may further comprise one or more specific protease cleavage sites.

In one embodiment, the fusion molecule is a fusion protein. In one embodiment, the fusion protein further comprises an Fc region/domain of an immunoglobulin (e.g., IgG1 or IgG4) or a variant thereof. In one embodiment, the variant of the Fc region/domain comprises up to 5, 4 or 3 mutations as compared to the wildtype sequence of the Fc region/domain. In one embodiment, said mutations are selected from the group consisting of amino acid substitutions and deletions, e.g., N- or C-terminal deletions. In one embodiment, a variant of the Fc region/domain of IgG4 (also referred to as "IgG4 Fc variant") comprises or consists of the amino acid sequence of SEQ ID NO: 21. In one embodiment, the FGF21 compound and the GLP-1R agonist are linked via the structure L1-Fc-L2, wherein L1 and L2 are peptide linkers (L1 and L2 being the same or different) and Fc is an Fc region/domain of an immunoglobulin or a variant thereof.

In one embodiment, the fusion protein comprises or consists of an amino acid sequence selected from the group consisting of SEQ ID NOs: 25, 26, 28, 30, 31, 32, 33, 35 and 36.

Further features of fusion proteins according to the present invention are described, e.g., in WO 2014/037373 A1 and WO 2017/093465 A1, which are incorporated herein by reference.

A "nucleic acid molecule" is according to the invention preferably deoxyribonucleic acid (DNA) or ribonucleic acid (RNA). A nucleic acid molecule may according to the invention be in the form of a molecule which is single-stranded or double-stranded and linear or covalently closed to form a circle.

The term "DNA" relates to a molecule which comprises deoxyribonucleotide residues and preferably is entirely or substantially composed of deoxyribonucleotide residues. "Deoxyribonucleotide" relates to a nucleotide which lacks a hydroxyl group at the 2'-position of a beta-D-ribofuranosyl group. The term "DNA" comprises isolated DNA such as partially or completely purified DNA, essentially pure DNA, synthetic DNA, and recombinantly generated DNA and includes modified DNA which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogues or analogues of naturally-occurring DNA. When used in connection with nucleotides, the term "naturally occurring" refers to the bases adenine (A), cytosine (C), guanine (G), thymine (T), and uracil (U).

The term "RNA" relates to a molecule which comprises ribonucleotide residues and preferably is entirely or substantially composed of ribonucleotide residues. "Ribonucleotide" relates to a nucleotide with a hydroxyl group at the 2'-position of a beta-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxy-nucleotides. These altered RNAs can be referred to as analogues or analogues of naturally-occurring RNA. According to the invention, "RNA" refers to single-stranded RNA or double stranded RNA. In one embodiment, the RNA is mRNA, e.g., in vitro transcribed RNA (IVT RNA) or synthetic RNA. The RNA may also be modified, e.g., with one or more modifications increasing the stability (e.g., the half-life) of the RNA. Such modifications are known to a person skilled in the art and include, for example, 5'-caps or 5'cap analogues The nucleic acid molecule according to the present invention may be contained/comprised in a vector. The term "vector", as used herein, includes all vectors known to the skilled person, including plasmid vectors, cosmid vectors, phage vectors, such as lambda phage, viral vectors, such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

Alternatively, the nucleic acid molecule according to the present invention may be integrated into a genome, e.g., the genome of a host cell. Means and methods to integrate a particular nucleic acid molecule into a genome are known to a person skilled in the art.

The term "cell" or "host cell" preferably relates to an intact cell, i.e., a cell with an intact membrane that has not released its normal intracellular components such as enzymes, organelles, or genetic material. An intact cell preferably is a viable cell, i.e. a living cell capable of carrying out its normal metabolic functions. Preferably, said term relates according to the invention to any cell which can be transfected or transformed with an exogenous nucleic acid. Preferably, the cell when transfected or transformed with an exogenous nucleic acid and transferred to a recipient can express the nucleic acid in the recipient. The term "cell" includes prokaryotic cells, such as bacterial cells, and eukaryotic cells, such as yeast cells, fungal cells or mammalian cells. Suitable bacterial cells include cells from gram-negative bacterial strains, such as strains of *Escherichia coli*, *Proteus*, and *Pseudomonas*, and gram-positive bacterial strains, such as strains of *Bacillus*, *Streptomyces*, *Staphylococcus*, and *Lactococcus*. Suitable fungal cells include cells from the species of *Trichoderma*, *Neurospora*, and *Aspergillus*. Suitable yeast cells include cells from the species of *Saccharomyces* (for example, *Saccharomyces cerevisiae*), *Schizosaccharomyces* (for example, *Schizosaccharomyces pombe*), *Pichia* (for example, *Pichia pastoris* and *Pichia methanolica*), and *Hansenula*. Suitable mammalian cells include for example CHO cells, BHK cells, HeLa cells, COS cells, HEK293 and the like. In one embodiment, HEK293 cells are used. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T cell receptor (TCR).

The "cell" or "host cell" may be isolated or part of a tissue or organism, in particular a "non-human organism".

The term "non-human organism", as used herein, is meant to include non-human primates or other animals, in particular mammals, such as cows, horses, pigs, sheep, goats, dogs, cats, rabbits or rodents, such as mice, rats, guinea pigs and hamsters.

As used herein, the term "kit of parts (in short: kit)" refers to an article of manufacture comprising one or more containers and, optionally, a data carrier. Said one or more containers may be filled with one or more of the above mentioned (re-)agents. Additional containers may be included in the kit that contain, e.g., diluents, buffers and further reagents. Said data carrier may be a non-electronical data carrier, e.g., a graphical data carrier such as an information leaflet, an information sheet, a bar code or an access code, or an electronical data carrier such as a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the agents of the present invention, e.g., combinations, pharmaceutical compositions and fusion molecules as well as related agents, such as nucleic acid molecules and host cells, as described herein.

The agents and compositions described herein may be administered via any conventional route, e.g., orally, pulmonary, by inhalation or parenterally, including by injection or infusion. In one embodiment, parenteral administration is used, e.g., intravenously, intraarterially, subcutaneously, intradermally or intramuscularly. The agents and compositions described herein may also be administered through sustained release administration.

Pharmaceutical compositions suitable for parenteral administration usually comprise a sterile aqueous or non-aqueous preparation of the active compound, which is preferably isotonic to the blood of the recipient. Examples of compatible carriers/solvents/diluents are sterile water, Ringer's solution, Lactated Ringer's solution, physiological saline, bacteriostatic saline (e.g., saline containing 0.9% benzyl alcohol), phosphate-buffered saline (PBS) and Hank's solution. In addition, usually sterile, fixed oils may be used as solution or suspension medium.

The agents and compositions described herein are usually administered in therapeutically effective amounts. A "therapeutically effective amount" refers to the amount, which achieves a desired therapeutic reaction or a desired therapeutic effect alone or together with further doses, preferably without causing unacceptable side-effects. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. An effective amount of an agent or composition described herein will depend on the condition to be treated, the severeness of the disease, the individual parameters of the subject, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a subject is insufficient with an initial dose, higher doses (or effectively higher doses achieved by a different, more localized route of administration) may be used.

According to the invention, the term "disease or disorder" refers to any pathological or unhealthy state, in particular obesity, being overweight, metabolic syndrome, diabetes mellitus, diabetic retinopathy, hyperglycemia, dyslipidemia, Non-Alcoholic SteatoHepatitis (NASH) and/or atherosclerosis.

The term "obesity" refers to a medical condition in which excess body fat has accumulated to the extent that it may have a negative effect on health. In terms of a human (adult) subject, obesity can be defined as a body mass index (BMI) greater than or equal to 30 kg/m$^2$ (BMI≥30 kg/m$^2$).

The term "overweight" refers to a medical condition in which the amount of body fat is higher than is optimally healthy. In terms of a human (adult) subject, obesity can be defined as a body mass index (BMI) greater than or equal to 25 kg/m$^2$ (e.g., 25 kg/m$^2$≤BMI<30 kg/m$^2$).

The BMI is a simple index of weight-for-height that is commonly used to classify overweight and obesity in adults. It is defined as a person's weight in kilograms divided by the square of his/her height in meters (kg/m$^2$).

"Metabolic syndrome" can be defined as a clustering of at least three of the following medical conditions: abdominal (central) obesity (e.g., defined as waist circumference ≥94 cm for Europid men and ≥80 cm for Europid women, with ethnicity specific values for other groups), elevated blood pressure (e.g., 130/85 mmHg or higher), elevated fasting plasma glucose (e.g., at least 100 mg/dL), high serum triglycerides (e.g., at least 150 mg/dL), and low high-density lipoprotein (HDL) levels (e.g., less than 40 mg/dL for males and less than 50 mg/dL for females).

"Diabetes mellitus" (also simply referred to as "diabetes") refers to a group of metabolic diseases characterized by high levels of blood glucose resulting from defects in insulin production, insulin action, or both. In one embodiment, diabetes mellitus is selected from the group consisting of type 1 diabetes mellitus, type 2 diabetes mellitus, gestational diabetes mellitus, late onset autoimmune diabetes in the adult (LADA), maturity onset diabetes of the young (MODY) and other types of diabetes resulting from specific genetic conditions, drugs, malnutrition, infections and other illnesses.

The current WHO diagnostic criteria for diabetes mellitus are as follows: fasting plasma glucose ≥7.0 mmol/l (126 mg/dL) or 2-h plasma glucose ≥11.1 mmol/l (200 mg/dL).

"Type 1 diabetes mellitus" (also known as "insulin-dependent diabetes (IDDM)" or "juvenile diabetes") is a condition characterized by high blood glucose levels caused by total lack of insulin. This occurs when the body's immune system attacks the insulin producing beta cells in the pancreas and destroys them. The pancreas then produces little or no insulin. Pancreatic removal or disease may also lead to loss of insulin-producing beta cells. Type 1 diabetes mellitus accounts for between 5% and 10% of cases of diabetes.

"Type 2 diabetes mellitus" (also known as "non-insulin-dependent diabetes (NIDDM)" or "adult-onset diabetes") is a condition characterized by excess glucose production in spite of the availability of insulin, and circulating glucose levels remain excessively high as a result of inadequate glucose clearance (insulin action). Type 2 diabetes mellitus may account for about 90% to 95% of all diagnosed cases of diabetes.

"Gestational diabetes" is a condition in which women without previously diagnosed diabetes exhibit high blood glucose levels during pregnancy (especially during the third trimester). Gestational diabetes affects 3-10% of pregnancies, depending on the population studied.

"Late onset autoimmune diabetes in the adult (LADA)" (also referred to as "slow onset type 1 diabetes") is a form of type 1 diabetes mellitus that occurs in adults, often with a slower course of onset.

"Maturity onset diabetes of the young (MODY)" refers to a hereditary form of diabetes caused by mutations in an autosomal dominant gene disrupting insulin production.

"Diabetic retinopathy" is an ocular disease induced by the metabolic disarrangements occurring in diabetic patients and leads to progressive loss of vision.

The term "hyperglycemia" refers to an excess of sugar (glucose) in the blood.

The term "dyslipidemia" refers to a disorder of lipoprotein metabolism, including lipoprotein overproduction ("hyperlipidemia") or deficiency ("hypolipidemia"). Dyslipidemias may be manifested by elevation of the total cholesterol, low-density lipoprotein (LDL) cholesterol and/or triglyceride concentrations, and/or a decrease in high-density lipoprotein (HDL) cholesterol concentration in the blood.

Non-Alcoholic SteatoHepatitis (NASH) is a liver disease characterized by an accumulation of fat (lipid droplets), along with inflammation and degeneration of hepatocytes. Once installed, the disease is accompanied with a high risk of cirrhosis, a state where the liver functions are altered and can progress to liver insufficiency. Thereafter, NASH often progresses to liver cancer.

"Atherosclerosis" is a vascular disease characterized by irregularly distributed lipid deposits called plaque in the intima of large and medium-sized arteries that may cause narrowing of arterial lumens and proceed to fibrosis and calcification. Lesions are usually focal and progress slowly and intermittently. Occasionally plaque rupture occurs leading to obstruction of blood flow resulting in tissue death distal to the obstruction. Limitation of blood flow accounts for most clinical manifestations, which vary with the distribution and severity of the obstruction.

The term "medicament", as used herein, refers to a substance/composition used in therapy, i.e., in the treatment of a disease or disorder.

By "treat" is meant to administer a compound or composition or a combination of compounds or compositions to a subject in order to prevent or eliminate a disease or disorder; arrest or slow a disease or disorder in a subject; inhibit or slow the development of a new disease or disorder in a subject; decrease the frequency or severity of symptoms and/or recurrences in a subject who currently has or who previously has had a disease or disorder; and/or prolong, i.e., increase, the lifespan of the subject.

In particular, the term "treating/treatment of a disease or disorder" includes curing, shortening the duration, ameliorating, preventing, slowing down or inhibiting progression or worsening, or preventing or delaying the onset of a disease or disorder or the symptoms thereof.

The term "subject" means according to the invention a subject for treatment, in particular a diseased subject (also referred to as "patient"), including human beings, non-human primates or other animals, in particular mammals, such as cows, horses, pigs, sheep, goats, dogs, cats, rabbits or rodents, such as mice, rats, guinea pigs and hamsters. In one embodiment, the subject/patient is a human being.

The present invention is now further described by reference to the following Examples, which are intended to illustrate, not to limit the scope of the present invention.

EXAMPLES

Example 1: Determining the Optimal GLP-1RA/FGF21 Activity Ratio by Systems Pharmacology Modelling Improved mechanistic insights into pharmacological effects of GLP-1RA/FGF21 fusion proteins in humans were used to identify the optimal GLP-1RA/FGF21 potency ratio. A mechanistic systems pharmacology model was developed describing effects of GLP-1 and FGF21 on glucose, lipid, and energy metabolism in humans (Cuevas-Ramos et al. (2009) Curr Diabetes Rev 5(4): 216-220; Deacon et al. (2011) Rev Diabet Stud 8(3): 293-306; Kim et al. (2008) Pharmacol Rev 60(4): 470-512; Kharitonenkov et al. (2014) Mol Metab 3(3): 221-229).

The model represented relevant pathways for GLP-1 and FGF21 effects. Glycemic control (i.e., HbA1c, fasting plasma glucose, postprandial glucose), lipid parameters (i.e., plasma triglycerides, fatty acids, cholesterol), and energy balance (i.e., body weight, food intake, energy expenditure) were captured to assess therapeutic response to simulated drug treatment (e.g., GLP-1RA/FGF21 fusion protein, Liraglutide, FGF21 analog LY2405319). For LY2405319, see Kharitonenkov et al. (2013) PLoS ONE 8(3): e58575.

The model covered key aspects of glucose homeostasis controlled by the hormones insulin, glucagon, and incretins (GLP-1, GIP). Major model endpoint regarding glycemic control was HbA1c. HbA1c is a common clinical endpoint used to estimate average plasma glucose concentrations over the previous few months. HbA1c was estimated within the model using the linear correlation between mean plasma glucose and HbA1c as reported by Nathan et al. (2008) Diabetes Care 31(8): 1473-1478.

The model incorporated triglyceride and fatty acid metabolism at a level appropriate to handle basic lipid metabolism, including the representation of cholesterol. HDL and non-HDL, i.e., LDL plus VLDL cholesterol, are the circulating lipoproteins. The representation of lipid metabolism allowed simulating the impact of FGF21 compounds on lipids and the interaction with statins. FGF21 compounds had significant effects on lipid concentrations (Gaich et al. (2013) Cell Metab 18(3): 333-340; Fisher et al. (2011) Endocrinology 152(8): 2996-3004).

Weight loss or gain in the model was measured as changes in body adipose mass. There was a direct relationship between fat mass and body weight (Broyles et al. (2011) Br J Nutr 105(8): 1272-1276). Food intake was based on basal and resting metabolic rate (Amirkalali et al. (2008) Indian J Med Sci 62(7): 283-290). The body adipose mass stayed constant, when energy expenditure equaled caloric intake. Therapy effects on food intake were implemented in the model using the formulation of (Gobel et al. (2014) Obesity (Silver Spring) 22(10): 2105-2108).

Food was considered to be carbohydrate (glucose equivalents), fat (fatty acid equivalents), and protein (amino acid equivalents). All nutrients entered the stomach, passed through a delay node and then a three-compartment gastrointestinal tract. The gastrointestinal tract design was based on work done by (Bastianelli et al. (1996) J Anim Sci 74(8): 1873-1887; Worthington (1997) Med Inform (Lond) 22(1): 35-45) with food digestion and absorption.

Nutrients, hormones, drugs, and disease conditions can cause delays in gastric emptying. Under healthy conditions, the gastric emptying rate depended on the size of the meal, its energy density, and the amount of nutrients in the stomach (Achour et al. (2001) Eur J Clin Nutr 55(9):

769-772; Fouillet et al. (2009) Am J Physiol Regul Integr Comp Physiol 297(6): R1691-1705). Individuals with diabetes often had a delay in glucose absorption seen with an oral glucose tolerance test or meal test (Bharucha et al. (2009) Clin Endocrinol (Oxf) 70(3): 415-420; Chang et al. (2012) Diabetes Care 35(12): 2594-2596). This delay was attributed to a slowing of gastric emptying. A delay between the stomach and small intestine was added in the model to account for delayed gastric emptying in diabetic subjects. Drugs and hormones (GLP-1) can affect the vagal tone of the stomach, which reduces mechanical mixing and/or peristalsis, and this also slows gastric emptying (Jelsing et al. (2012) Diabetes Obes Metab 14(6): 531-538; Little et al. (2006) J Clin Endocrinol Metab 91(5): 1916-1923; Nauck et al. (2011) Diabetes 60(5): 1561-1565; van Can et al. (2013) Int J Obes (Lond) 38(6): 784-93).

One aim of this investigation was preventing GLP-1 related adverse effects, i.e., nausea and vomiting (Lean et al. (2014) Int J Obes (Lond) 38(5): 689-697). Gastric emptying measures provided an estimate of adverse events such as nausea and vomiting that correlated with low rates of gastric emptying. Hence, a marker for gastric adverse events in the model was the sum of gastric emptying rate.

Different virtual patients were implemented in the model platform representing healthy and type 2 diabetic patients at different stages of the disease. Moreover, the virtual patients covered different degrees of obesity and dyslipidemia. The virtual patients represented variability in disease severity and pathophysiology and phenotypic variability observed in the clinic.

Several therapies were implemented in the model, i.e., GLP-1RA/FGF21 fusion protein, Liraglutide, FGF21 analog LY2405319, Metformin, Atorvastatin, Sitagliptin, human insulin. These therapies could be switched on or off in the simulations. The virtual patient was assumed to be on a background of Metformin and Atorvastatin when administering the GLP-1RA/FGF21 fusion protein.

Virtual GLP-1RA/FGF21 fusion proteins were implemented in the model. The fusion protein contained both, FGF21 and GLP-1 agonistic activities, and it had the same effects as both, FGF21 and GLP-1 receptor agonists. The pharmacokinetic profiles of the virtual fusion proteins were assumed to be similar to Dulaglutide (Geiser et al. (2016) Clin Pharmacokinet 55(5): 625-34).

The model was validated by comparison with numerous data sets. The simulation results were qualitatively consistent with relevant data and knowledge, e.g., Hellerstein et al. (1997) J Clin Invest 100(5): 1305-1319; Muscelli et al. (2008) Diabetes 57(5): 1340-1348. The model matched relevant quantitative test data, e.g., Aschner et al. (2006) Diabetes Care 29(12): 2632-2637; Dalla Man, Caumo et al. (2005) Am J Physiol Endocrinol Metab 289(5): E909-914; Dalla Man et al. (2005) Diabetes 54(11): 3265-3273; Fiallo-Scharer (2005) J Clin Endocrinol Metab 90(6): 3387-3391; Hahn et al. (2011) Theor Biol Med Model 8: 12; Herman et al. (2005) Clin Pharmacol Ther 78(6): 675-688; Herman et al. (2006) J Clin Pharmacol 46(8): 876-886 and J Clin Endocrinol Metab 91(11): 4612-4619; Hojlund et al. (2001) Am J Physiol Endocrinol Metab 280(1): E50-58; Monauni et al. (2000) Diabetes 49(6): 926-935; Nauck et al. (2009) Diabetes Care 32(1): 84-90; Nauck et al. (1993) J Clin Invest 91(1): 301-307; Nauck et al. (2004) Regul Pept 122(3): 209-217; Tzamaloukas et al. (1989) West J Med 150(4): 415-419; Sikaris (2009) J Diabetes Sci Technol 3(3): 429-438; Vicini and Cobelli (2001) Am J Physiol Endocrinol Metab 280(1): E179-186; Vollmer et al. (2008) Diabetes 57(3): 678-687.

Existing therapies were implemented in the model for direct comparison, including FGF21 analog and GLP-1 receptor agonist. The FGF21 analog's effects were validated with clinical data, e.g., Gaich et al. 2013. The GLP-1 receptor agonist Liraglutide was a direct competitor for the target, and its implementation was compared with various clinical data, e.g., Jacobsen et al. (2009) Br J Clin Pharmacol 68(6): 898-905; Elbrond et al. (2002) Diabetes Care 25(8): 1398-1404; Chang et al. (2003) Diabetes 52(7): 1786-1791; Kolterman et al. (2003) J Clin Endocrinol Metab 88(7): 3082-3089; Degn et al. (2004) Diabetes 53(5): 1187-1194; Kolterman et al. (2005) Am J Health Syst Pharm 62(2): 173-181; Vilsboll et al. (2008) Diabet Med 25(2): 152-156; Buse et al. (2009) Lancet 374(9683): 39-47; Jelsing et al. (2012) Diabetes Obes Metab 14(6): 531-538; Hermansen et al. (2013) Diabetes Obes Metab 15(11): 1040-1048; Suzuki et al. (2013) Intern Med 52(10): 1029-1034; van Can et al. (2013) Int J Obes (Lond) 38(6): 784-93); Zinman et al. (2009) Diabetes Care 32(7): 1224-1230; Russell-Jones et al. (2009) Diabetologia 52(10): 2046-2055; Pratley et al. (2011) Int J Clin Pract 65(4): 397-407; Nauck et al. (2013) Diabetes Obes Metab 15(3): 204-212; Flint et al. (2011) Adv Ther 28(3): 213-226; Kapitza et al. (2011) Adv Ther 28(8): 650-660; Astrup et al. (2012) Int J Obes (Lond) 36(6): 843-854.

The model platform allowed simulating beneficial and adverse effects of virtual GLP-1 RA/FGF21 fusion proteins with varying activity ratios. Effective FGF21-mediated EC50 values were set constant derived from Gaich et al. (2013) Cell Metab 18(3): 333-340. Effective GLP-1-mediated EC50 values were reduced by a factor of 2 to 600 in increments of 1 relative to endogenous GLP-1 (Table 1).

TABLE 1

GLP-1R agonist/FGF21 fusion protein pharmacodynamics (EC50 values).

| | Effective GLP-1-Mediated EC50 Values | | | | Effective |
|---|---|---|---|---|---|
| Potency Ratio* | Peripheral Glucose Uptake | Insulin Release | Gastric Emptying | Food Intake | FGF21-Mediated EC50 Values** |
| 1 | 35 pM | 20 pM | 50 pM | 80 pM | 3547 pM |
| 100 | 3500 pM | 2000 pM | 5000 pM | 8000 pM | 3547 pM |

*Relative to endogenous GLP-1
**FGF21 EC50 values were set assuming half maximal effect per Gaich et al. (2013) Cell Metab 18(3): 333-340

Figure 1:
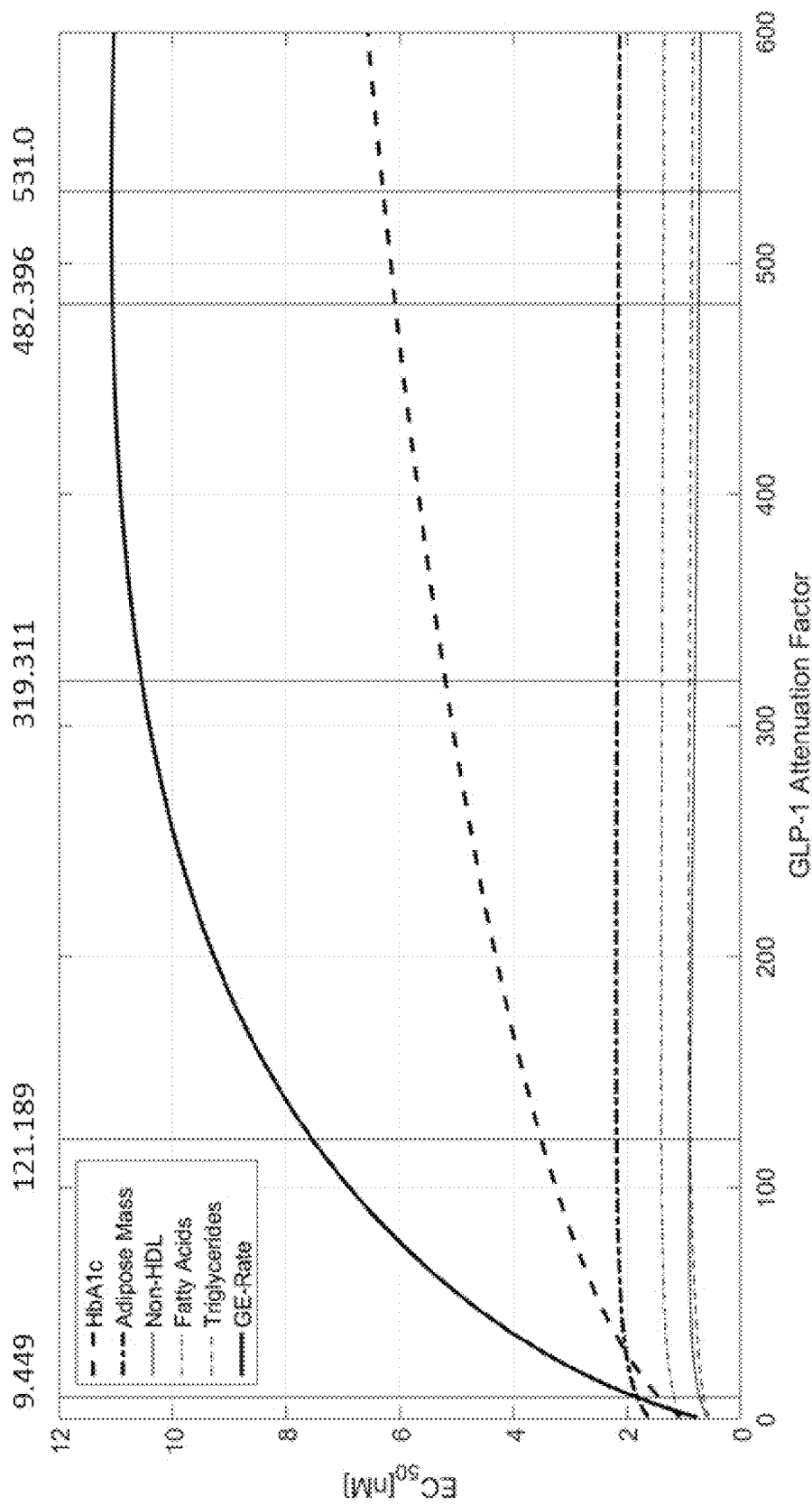
FIG. 1 is a graph showing EC50 of the adverse effect (gastric emptying (GE) rate) and pharmacodynamics (i.e., HbA1c, Triglycerides, Fatty Acids, Non-HDL, Adipose Mass) depending on the GLP-1 attenuation factor (12-months simulation)

For each virtual fusion protein, the exposure-response relation was simulated for relevant pharmacodynamic endpoints, i.e., HbA1c, triglycerides, fatty acids, non-HDL cholesterol, and adipose mass. As marker for GLP-1-mediated adverse events, the gastric emptying rate was used. 52 weeks treatment of an average obese dyslipidemic type 2 diabetic virtual patient with GLP-1RA/FGF21 fusion proteins was simulated for a broad dose range. After treatment for 52 weeks, all relevant pharmacodynamics endpoints are expected to reach steady state. For each endpoint the half maximal effective concentration (EC50 value) was determined from the exposure-response curves. The EC50 values varied with the activity ratio, especially for the mainly GLP-1-mediated endpoints HbA1c and gastric emptying rate. FIG. 1 depicts the EC50 values depending on the GLP-1 attenuation factor. An increased GLP-1 attenuation factor indicates a reduction in GLP-1R agonistic activity.

This procedure allowed identifying relevant activity ratios, for which adverse effects kick in at higher plasma levels as compared to pharmacodynamics effects. For GLP-1 attenuation factors greater than 9, EC50 of GLP-1-mediated gastrointestinal adverse effect was greater than EC50 of pharmacodynamic effects. Hence, gastric adverse effects kicked in at higher plasma levels than pharmacodynamics effects. It is possible to find a dose providing all desirable pharmacodynamic effects while avoiding GLP-1-mediated gastrointestinal adverse effects. Therefore, activity ratios below 1:10 were not relevant.

The maximal EC50 value for gastric emptying rate was reached at attenuation factor 531. The maximal distance between adverse and mean pharmacodynamics effects was reached at attenuation factor 482 (FIG. 2). Therefore, activity ratios beyond 1:482 were not relevant. Maximal distance between maximum of pharmacodynamics (HbA1c) and adverse effect was 319. Maximal distance between maximum of pharmacodynamics (HbA1c) and adverse effect normalized by spreading of FGF21- (lipids) and GLP-1-mediated effects (HbA1c) was 121.

GLP-1RA/FGF21 fusion proteins with potency ratios between 1:10 and 1:482 were predicted to be most beneficial in improving lipid profile, body weight, and glucose metabolism and likely caused no significant adverse events based on gastric emptying response. Lower potency ratios were likely not a good candidate based on its predicted strong inhibition of gastric emptying and potential for adverse events. Higher potency ratios were likely to be not sufficiently effective and therefore not competitive.

Moreover, 12-weeks treatment of an average obese dyslipidemic type 2 diabetic virtual patient with GLP-1RA/FGF21 fusion proteins was simulated for a broad dose range, since the mainly GLP-1 mediated parameter HbA1c clinically reaches steady state after 12-weeks treatment.

FIG. 3 depicts the EC50 values depending on the GLP-1 attenuation factor for 12-weeks simulation. For GLP-1 attenuation factors greater than 18, EC50 of GLP-1-mediated gastrointestinal adverse effect was greater than EC50 of pharmacodynamic effects. The maximal EC50 value for gastric emptying rate was reached at attenuation factor 501. The maximal distance between adverse and mean pharmacodynamics effects was reached at attenuation factor 469 (FIG. 4). Maximal distance between maximum of pharmacodynamics (HbA1c) and adverse effect was 313. Maximal distance between maximum of pharmacodynamics (HbA1c) and adverse effect normalized by spreading of FGF21- (lipids) and GLP-1-mediated effects (HbA1c) was 123.

Efficacy and potential for adverse events for GLP-1RA/FGF21 fusion proteins with different activity ratios were investigated by means of the described systems pharmacology approach. Fusion proteins with presumably calculated ideal potency ratios were identified, predicted to be beneficial in improving lipid profile, body weight, and glycemic control while likely not causing significant adverse GLP-1RA associated effects based on gastric emptying response. Therefore, compounds with the selected model-informed potency ratios were predicted to provide a good efficacy versus risk profile.

Example 2: Expression of GLP1RA-FGF21 Fusion Proteins in HEK293 Cells

The FGF21 protein of SEQ ID NO: 2 was fused either directly to a GLP1RA or a linker sequence was inserted between the GLP1RA and FGF21 sequence. In all constructs, the FGF21 construct was fused C-terminally to the GLP1RA sequence. If a linker was inserted, the GLP1RA was fused N-terminally to the linker sequence, and FGF21 was fused C-terminally to the linker sequence. The DNA sequence of the GLP1 RA-FGF21 fusion protein was fused N-terminal to an IL2 signal sequence followed by a Histidine-rich sequence (His-tag) and a Tev-cleavage site. The GLP1RA-FGF21 fusion proteins were produced by transient transfection of HEK293 cells. The signal sequence was required for secretion of the desired fusion protein into the culture medium. The desired fusion proteins were purified from the culture supernatant using immobilized metal-ion affinity chromatography (IMAC). After elution from the IMAC-column, the N-terminal His-tag may be cleaved by addition of Tev-protease. For construct screening purposes, the His-tag was cleaved by addition of Tev-protease directly into the incubation medium for the GLP1 RA-activity assay. Incubation time before starting the assay was 10-60 min to ensure complete cleavage of the His-tag. Constructs which have GLP1RA-activity in the desired range were produced at a larger scale. GLP1 RA-Fc-FGF21 fusion proteins were produced by transient transfection in HEK293 cells. The desired fusion proteins were purified from the culture supernatants using IMAC with cOmplete His-Tag purification resin (Roche). After cleavage of the His-tag, the cleavage reaction solution was passed a second time over an IMAC column (cOmplete™ His-Tag purification resin (Roche)), collecting the (his-tag-free) flow through fraction. The fusion protein was further purified using a gelfiltration column with phosphate buffered saline (PBS, Gibco) as running buffer. Fractions containing the desired fusion proteins were collected, pooled, concentrated and stored at −80° C. until further usage.

Example 3: In Vitro Cellular Assay for Human FGF21 Receptor Efficacy in CHO Cells (in-Cell Western)

The cellular in vitro efficacy of mature human FGF21 (SEQ ID NO: 2) or FGF21 variants was measured using a specific and highly sensitive In-Cell Western (ICW) assay. The ICW assay is an immunocytochemical assay usually performed in microplate format. CHO Flp-In cells (Invitrogen, Darmstadt, Germany) stably expressing the human FGFR1c (=FGF receptor 1c isoform) together with human beta-Klotho (KLB) were used for an FGF21 receptor autophosphorylation assay using In-Cell Western (Aguilar H. N. et al. (2010) PLoS ONE 5(4): e9965). In order to determine the receptor autophosphorylation level or downstream activation of the MAP kinase ERK1/2, $2 \times 10^4$ cells/well were seeded into 96-well plates and grown for 48 h. Cells were serum starved with serum-free medium Ham's F-12 Nutrient Mix with GlutaMAX (Gibco, Darmstadt, Germany) for 3-4 h. The cells were subsequently treated with increasing concentrations of either mature human FGF21 (SEQ ID NO: 2) for 5 min at 37° C. After incubation, the medium was discarded, and the cells were fixed in 3.7% freshly prepared para-formaldehyde for 20 min. Cells were permeabilized with 0.1% Triton-X-100 in PBS for 20 min. Blocking was performed with Odyssey blocking buffer (LICOR, Bad Homburg, Germany) for 2 h at room temperature. A primary antibody (anti-pFGFR Tyr653/654 (New England Biolabs, Frankfurt, Germany) or anti-pERK Phospho-p44/42 MAP Kinase Thr202/Tyr204 (Cell Signaling)) was added and incubated overnight at 4° C. After incubation of the primary antibody, cells were washed with PBS plus 0.1% Tween20. The secondary anti-Mouse 800CW antibody (LICOR, Bad Homburg, Germany) was incubated for 1 h at room temperature. Subsequently, cells were washed again with PBS plus 0.1% Tween20, and infrared dye signals were quantified with an Odyssey imager (LICOR, Bad Homburg, Germany).

Results were normalized by quantification of DNA with TO-PRO3 dye (Invitrogen, Karlsruhe, Germany). Data were obtained as arbitrary units (AU), and EC50 values were obtained from dose-response curves and are summarized in Table 2. FIGS. 5A-5B show the results from an ICW with CHO cells overexpressing human FGFR1c plus KLB.

TABLE 2

EC50-values of mature human FGF21 (SEQ ID NO: 2) measured via ICW pFGFR or ICW pERK in CHO cells overexpressing human FGFR1c and KLB.

| Protein | pFGFR ICW EC50 (nmol/L) | pERK ICW EC50 (nmol/L) |
|---|---|---|
| FGF21, human (SEQ ID NO: 2) | 4.8 ± 0.23 (n = 59) | 0.18 ± 0.02 (n = 61) |

Example 4: In Vitro Cellular Assay for Human GLP-1 Receptor Efficacy

Agonism of compounds for human glucagon-like peptide-1 (GLP-1) receptor was determined by functional assays measuring cAMP response in a HEK-293 cell line stably expressing human GLP-1 receptor.

The cAMP content of cells was determined using a kit from Cisbio Corp. (cat. no. 62AM4PEC) based on HTRF (Homogenous Time Resolved Fluorescence). For preparation, cells were split into T175 culture flasks and grown overnight to near confluence in medium (DMEM/10% FBS). Medium was then removed and cells washed with PBS lacking calcium and magnesium, followed by proteinase treatment with accutase (Sigma-Aldrich cat. no. A6964). Detached cells were washed and resuspended in assay buffer (1×HBSS; 20 mM HEPES, 0.1% BSA, 2 mM IBMX) and cellular density determined. They were then diluted to $4 \times 10^5$ cells/mL and 25 µL-aliquots dispensed into the wells of 96-well plates. For measurement, 25 µL of test compound in assay buffer was added to the wells, followed by incubation for 30 minutes at room temperature. After addition of HTRF reagents diluted in lysis buffer (kit components), the plates were incubated for 1 h, followed by measurement of the fluorescence ratio at 665/620 nm. In vitro potency of agonists was quantified by determining the concentrations that caused 50% activation of maximal response ($EC_{50}$). Results are summarized in Table 3.

TABLE 3

EC50-values of GLP-1 receptor agonists (SEQ ID NO: 7 and 24-36) measured via detection of cAMP response in a HEK-293 cell line stably expressing human GLP-1 receptor. Corresponding ratios of GLP-1R agonistic activity (native GLP-1(7-36)/GLP-1R agonist) are shown as well. A ratio X means that GLP-1R agonistic activity is X-fold reduced as compared to the GLP-1R agonistic activity of native GLP-1(7-36).

| SEQ ID NO | Ratio GLP-1R agonistic activity: native GLP-1(7-36)/tested GLP-1R agonist | EC50 (pmol/L) |
|---|---|---|
| 7 | 1.0 | 0.77 |
| 24 | 6.7 | 5.15 |
| 31 | 9.5 | 7.30 |
| 36 | 18.9 | 14.59 |
| 25 | 54.1 | 41.66 |
| 26 | 78.6 | 60.54 |
| 32 | 81.9 | 63.03 |
| 33 | 163.6 | 125.98 |

TABLE 3-continued

EC50-values of GLP-1 receptor agonists (SEQ ID NO: 7 and 24-36) measured via detection of cAMP response in a HEK-293 cell line stably expressing human GLP-1 receptor. Corresponding ratios of GLP-1R agonistic activity (native GLP-1(7-36)/GLP-1R agonist) are shown as well. A ratio X means that GLP-1R agonistic activity is X-fold reduced as compared to the GLP-1R agonistic activity of native GLP-1(7-36).

| SEQ ID NO | Ratio GLP-1R agonistic activity: native GLP-1(7-36)/tested GLP-1R agonist | EC50 (pmol/L) |
|---|---|---|
| 35 | 174.1 | 134.03 |
| 30 | 224.6 | 172.97 |
| 28 | 256.4 | 197.44 |
| 29 | 767.8 | 591.19 |
| 27 | 877.1 | 675.33 |
| 34 | 1279.0 | 984.80 |

TABLE 4

Selected ratios of GLP-1R agonistic activity (native GLP-1(7-36)/GLP-1R agonist) and corresponding calculated EC50-values (based on the results obtained above). A ratio X means that GLP-1R agonistic activity is X-fold reduced as compared to the GLP-1R agonistic activity of native GLP-1(7-36).

| Ratio GLP-1R agonistic activity: native GLP-1(7-36)/tested GLP-1R agonist | EC50 (pmol/L) |
|---|---|
| 9 | 6.93 |
| 18 | 13.86 |
| 121 | 93.17 |
| 123 | 94.71 |
| 313 | 241.01 |
| 319 | 245.63 |
| 469 | 361.13 |
| 482 | 371.14 |
| 501 | 385.77 |
| 531 | 408.87 |

Example 5: Synthesis of Peptidic Compounds

Whereas fusion proteins were produced by recombinant methods (see Example 2), isolated peptidic GLP-1R agonists were chemically synthesized.

More particularly, peptides were synthesized by a manual synthesis procedure:

0.3 g Desiccated Rink amide MBHA Resin (0.66 mmol/g) was placed in a polyethylene vessel equipped with a polypropylene filter. Resin was swollen in DCM (15 ml) for 1 h and DMF (15 ml) for 1h. The Fmoc group on the resin was de-protected by treating it twice with 20% (v/v) piperidine/DMF solution for 5 and 15 min. The resin was washed with DMF/DCM/DMF (6:6:6 time each). A Kaiser test (quantitative method) was used for the conformation of removal of Fmoc from solid support. The C-terminal Fmoc-amino acid (5 equiv. excess corresponding to resin loading) in dry DMF was added to the de-protected resin and coupling of the next Fmoc-amino acid was initiated with 5 equivalent excess of DIC and HOBT in DMF. The concentration of each reactant in the reaction mixture was approximately 0.4 M. The mixture was rotated on a rotor at room temperature for 2 h. Resin was filtered and washed with DMF/DCM/DMF (6:6:6 time each). Kaiser test on peptide resin aliquot upon completion of coupling was negative (no colour on the resin). After the first amino acid attachment, the unreacted amino group, if any, in the resin was capped used acetic anhydride/pyridine/DCM (1:8:8) for 20 minutes to avoid any deletion of the sequence. After capping, resin was washed with DCM/DMF/DCM/DMF (6/6/6/6 time each). The Fmoc group on the C-terminal amino acid attached peptidyl resin was deprotected by treating it twice with 20% (v/v) piperidine/DMF solution for 5 and 15 min. The resin was washed with DMF/DCM/DMF (6:6:6 time each). The Kaiser test on peptide resin aliquot upon completion of Fmoc-deprotection was positive.

The remaining amino acids in target sequence on Rink amide MBHA Resin were sequentially coupled using Fmoc AA/DIC/HOBt method using 5 equivalent excess corresponding to resin loading in DMF. The concentration of each reactant in the reaction mixture was approximately 0.4 M. The mixture was rotated on a rotor at room temperature for 2 h. Resin was filtered and washed with DMF/DCM/DMF (6:6:6 time each). After each coupling step and Fmoc deprotection step, a Kaiser test was carried out to confirm the completeness of the reaction. After the completion of the linear sequence, the ε-amino group of lysine used as branching point or modification point was deprotected by using 2.5% hydrazine hydrate in DMF for 15 min×2 and washed with DMF/DCM/DMF (6:6:6 time each). The γ-carboxyl end of glutamic acid was attached to the ε-amino group of Lys using Fmoc-Glu(OH)—OtBu with DIC/HOBt method (5 equivalent excess with respect to resin loading) in DMF. The mixture was rotated on a rotor at room temperature for 2 h. The resin was filtered and washed with DMF/DCM/DMF (6×30 ml each). The Fmoc group on the glutamic acid was de-protected by treating it twice with 20% (v/v) piperidine/DMF solution for 5 and 15 min (25 ml each). The resin was washed with DMF/DCM/DMF (6:6:6 time each). A Kaiser test on peptide resin aliquot upon completion of Fmoc-deprotection was positive.

If the side-chain branching also contains one more γ-glutamic acid, a second Fmoc-Glu(OH)—OtBu was used for the attachment to the free amino group of γ-glutamic acid with DIC/HOBt method (5 equivalent excess with respect to resin loading) in DMF. The mixture was rotated on a rotor at room temperature for 2 h. Resin was filtered and washed with DMF/DCM/DMF (6×30 ml each). The Fmoc group on the γ-glutamic acid was de-protected by treating it twice with 20% (v/v) piperidine/DMF solution for 5 and 15 min (25 mL). The resin was washed with DMF/DCM/DMF (6:6:6 time each). A Kaiser test on peptide resin aliquot upon completion of Fmoc-deprotection was positive.

Final Cleavage of Peptide from the Resin:

The peptidyl resin synthesized by manual synthesis was washed with DCM (6×10 ml), MeOH (6×10 ml) and ether (6×10 ml) and dried in vacuum desiccators overnight. The cleavage of the peptide from the solid support was achieved by treating the peptide-resin with reagent cocktail (80% TFA/5% thioanisole/5% phenol/2.5% EDT/2.5% DMS/5% DCM) at room temperature for 3 h. Cleavage mixture was collected by filtration and the resin was washed with TFA (2 ml) and DCM (2×5 ml). The excess TFA and DCM was concentrated to small volume under nitrogen and a small amount of DCM (5-10 ml) was added to the residue and evaporated under nitrogen. The process was repeated 3-4 times to remove most of the volatile impurities. The residue was cooled to 0° C. and anhydrous ether was added to precipitate the peptide. The precipitated peptide was centrifuged and the supernatant ether was removed and fresh ether was added to the peptide and re-centrifuged. The crude sample was preparative HPLC purified and lyophilized. The identity of peptide was confirmed by LCMS.

TABLE 5

List of Sequences.

| SEQ ID NO | Description | Sequence |
|---|---|---|
| 1 | full-length human wild-type FGF21 (including signal sequence Met1-Ala28) | MDSDETGFEH SGLWVSVLAG LLLGACQAHP IPDSSPLLQF GGQVRQRYLY TDDAQQTEAH LEIREDGTVG GAADQSPESL LQLKALKPGV IQILGVKTSR FLCQRPDGAL YGSLHFDPEA CSFRELLLED GYNVYQSEAH GLPLHLPGNK SPHRDPAPRG PARFLPLPGL PPAPPEPPGI LAPQPPDVGS SDPLSMVGPS QGRSPSYAS |
| 2 | mature human wild-type FGF21, FGF21(His29-Ser209) | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 3 | FGF21(His29-Ser209) A59C, G71C | ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 4 | FGF21(His29-Ser209) Q55C, N149, CG198Y | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPLHLPG CKSPHRDPAP RGPARFLPLP GLPPAPPEPP GILAPQPPDV GSSDPLSMVY PSQGRSPSYA S |
| 5 | FGF21(His29-Ser209) Q55C, P147C, delP199 | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPLHLCG NKSPHRDPAP RGPARFLPLP GLPPAPPEPP GILAPQPPDV GSSDPLSMVG SQGRSPSYAS |
| 6 | FGF21(His29-Ser209) Q55C, N149C, delP199 | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPLHLPG CKSPHRDPAP RGPARFLPLP GLPPAPPEPP GILAPQPPDV GSSDPLSMVG SQGRSPSYAS |
| 7 | GLP-1(7-36) | HAEGTFTSDV SSYLEGQAAK EFIAWLVKGR |
| 8 | GLP1(7-36) A8G, V16L, S18K, Y19Q, L20M, G22E, Q23E, A25V, K26R, E27L, A30E, V33K, K34N, R36G, insPSSGAPPPS | HGEGTFTSDL SKQMEEEAVR LFIEWLKNGG PSSGAPPPS |
| 9 | GLP1(7-36) A8G, V16L, S18K, Y19Q, G22E, Q23E, A25V, K260, E27L, A30E, V33L, K34A, G35T, R36G, insPSSGAPPPS | HGEGTFTSDL SKQLEEEAVQ LFIEWLLATG PSSGAPPPS |

TABLE 5-continued

List of Sequences.

| SEQ ID NO | Description | Sequence |
|---|---|---|
| 10 | GLP1(7-36) A8G, V16L, S18I, Y19Q, E21 D, G22E, Q23E, A25V, K26R, E27L, A30E, V33L, K34A, G35T, R36G, insPVSGAPPPS | HGEGTFTSDL SIQLDEEAVR LFIEWLLATG PVSGAPPPS |
| 11 | GLP1(7-36) A8G, V16L, S18I, Y19Q, E21 D, G22E, Q23E, A25V, K26R, E27L, A30E, V33L, K34A, G35T, R36G, insPVSGAPPPS | HGEGTFTSDL SIQLDEEAVR LFIEWLEATG PVSGAPPPS |
| 12 | GLP1(7-36) insG, A8G, V16L, S18I, Y19Q, G22E, Q23E, A25V, K26R, E27L, A30E, V33L, K34A, R36G, insPSSGAPPPS | GHGEGTFTSD LSIQLEEEAV RLFIEWLLAG GPSSGAPPPS |
| 13 | GLP1(7-36) insG, A8G, V16L, S18I, Y19Q, G22E, Q23E, A25V, K26R, E27L, A30E, V33L, K34A, G35T, R36G, insPSSGAPPPS | GHGEGTFTSD LSIQLEEEAV RLFIEWLLAT GPSSGAPPPS |
| 14 | GLP1(7-36) A8G, V16L, S18K, Y19Q, E21 D, G22E, Q23E, A25V, K26Q, E27L, A30E, V33L, K34A, G35T, R36G, insPSSGEPPPES | HGEGTFTSDL SKQLEEEAVQ LFIEWLLATG PSSGEPPPES |
| 15 | GLP1(7-36) A8G, V16L, S18K, Y19Q, L20M, E21D, G22E, Q23E, A25V, K26R, E27L, A30E, V33K, K34N, R36G | HGEGTFTSDL SKQMEEEAVR LFIEWLKNGG |

TABLE 5-continued

List of Sequences.

| SEQ ID NO | Description | Sequence |
|---|---|---|
| 16 | GLP1(7-36) A8G, V16L, S18K, Y19Q, G22E, Q23E, A25V, K26Q, E27L, A30E, V33L, K34A, G35T, R36G | HGEGTFTSDL SKQLEEEAVQ LFIEWLLATG |
| 17 | GLP1(7-36) A8G, V16L, S18K, Y19Q, G22E, Q23E, A25V, K26Q, E27L, A30E, V33L, K34A, G35T, R36G, insPSSGEPPPE | HGEGTFTSDL SKQLEEEAVQ LFIEWLLATG PSSGEPPPE |
| 18 | GLP1(7-36) insG, A8G, V16L, S18K, Y19Q, G22E, Q23E, A24R, A25V, K26Q, A30E, insPSSGAPPPS | GHGEGTFTSD LSKQLEEERV QEFIEWLVKG RPSSGAPPPS |
| 19 | GLP1(7-36) A8G, V16L, S18K, Y19Q, G22E, Q23E, A25V, K26Q, E27L, A30E, V33E, K34A, G35T, R36G, insPSSGAPPPS | HGEGTFTSDL SKQLEEEAVQ LFIEWLEATG PSSGAPPPS |
| 20 | GLP1(7-36) insG, A8G, V16L, S18I, Y19Q, G22E, Q23E, A25V, K26R, E27L, A30E, V33L, K34A, R36G, insPKKQRLS | GHGEGTFTSD LSIQLEEEAV RLFIEWLLAG GPKKQRLS |
| 21 | IgG4 Fc variant, IGHG4 HUMAN (Glu99-Gly326) | ESKYGPPCPP CPAPEFEGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLG |

TABLE 5-continued

List of Sequences.

| SEQ ID NO | Description | Sequence |
|---|---|---|
| 22 | (G7S)(G4S)(G4S) A Linker (19GS) | GGGGGGGSGG GGSGGGGSA |
| 23 | (G3S)(GS)A Linker (7GS) | GGGSGSA |
| 24 | GLP1(7-36) A8G, V16L, S18K, Y19Q, L20M, G22E, Q23E, A25V, K26R, E27L, A30E, V33L, K34N, R36G, insPSSGAPPPS_[19GS]_IgG4 Fc variant [7GS]_FGF21(His29-Ser209)_A59C, G71C | HGEGTFTSDL SKQMEEEAVR LFIEWLKNGG PSSGAPPPSG GGGGGGSGGG GSGGGGSAES KYGPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCCSVMHE ALHNHYTQKS LSLSLGGGGS VKTSRFLCQR PDGALYGSLH FDPEACSFRE LLEDGYNVY QTECHLEIRE DGTVGCAADQ SPESLLQLKA LKPGVIQILG EPPGILAPQP PDVGSSDPLS MVGPSQGRSP SYAS QSEAHGLPLH LPGNKSPHRD PAPRGPARFL |
| 25 | GLP1(7-36) A8G, V16L, S18K, Y19Q, G22E, Q23E, A25V, K26Q, E27L, A30E, V33L, K34A, G35T, R36G, insPSSGAPPPS_[19GS]_IgG4 Fc variant [7GS]_FGF21(His29-Ser209)Q55C, N149C, G198Y | HGEGTFTSDL SKQLEEEAVQ LFIEWLLATG PSSGAPPPSG GGGGGGSGGG GSGGGGSAES KYGPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCCSVMHE ALHNHYTQKS LSLSLGGGGS VKTSRFLCQR PDGALYGSLH FDPEACSFRE LLEDGYNVY QTEAHLEIRE DGTVGGAADQ SPESLLQLKA LKPGVIQILG EPPGILAPQP PDVGSSDPLS MVYPSQGRSP YAS QSEAHGLPLH LPGCKSPHRD PAPRGPARFL |
| 26 | GLP1(7-36) A8G, V16L, S18I, Y19Q, E21D, G22E, Q23E, A25V, K26R, E27L, A30E, V33L, K34A, G35T, R36G, insPVSGAPPPS_[19GS]_IgG4 Fc variant [7GS]_FGF21(His29-Ser209)Q55C, P147C, delP199 | HGEGTFTSDL SIQLDEEAVR LFIEWLLATG PVSGAPPPSG GGGGGGSGGG GSGGGGSAES KYGPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCCSVMHE ALHNHYTQKS LSLSLGGGGS VKTSRFLCQR PDGALYGSLH FDPEACSFREL LLEDGYNVY QTEAHLEIRE LCGNKSPHRD SPESLLQLKA LKPGVIQILG EPPGILAPQP PDVGSSDPLS MVGSQGRSP YAS QSEAHGLPLH PAPRGPARFL |
| 27 | GLP1(7-36) A8G, V16L, S18I, | HGEGTFTSDL SIQLDEEAVR LFIEWLEATG PVSGAPPPSG GGGGGGSGGG GSGGGGSAES KYGPCPPCP APEFEGGPSV FLFPPKPKDT LMISRTPEVT CVVVDVSQED PEVQFNWYVD GVEVHNAKTK PREEQFNSTY RVVSVLTVLH QDWLNGKEYK |

TABLE 5-continued

List of Sequences.

| SEQ ID NO | Description | Sequence |
|---|---|---|
| | Y19Q, E21D, G22E, Q23E, A25V, K26R, E27L, A30E, V33L, K34A, G35T, R36G, insPVSGAPPPS_[19GS]_IgG4 Fc variant [7GS]_FGF21(His29-Ser209)Q55C, N149C, delP199 | CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCCSVMHE ALHNHYTQKS LSLSLGGGGS GSAHPIPDSS PLLQFGGQVR QRYLYTDDAC QTEAHLEIRE DGTVGGAADQ SPESLLQLKA LKPGVIQILG VKTSRFLCQR PDGALYGSLH FDPEACSFRE LLEDGYNVY QSEAHGLPLH LPGCKSPHRD PAPRGRAFL PLPGLPPAPP EPPGILAPQP PDVGSSDPLS MVGSQGRSPS YAS |
| 28 | GLP1(7-36) insG, A8G, V16L, S18I, Y19Q, G22E, Q23E, A25V, K26R, E27L, A30E, V33L, K34A, R36G, insPSSGAPPPS_[19GS]_IgG4 Fc variant [7GS]_FGF21(His29-Ser209)Q55C, N149C, delP199 | GHGEGTFTSD LSIQLEEEAV RLFIEWLLAG GPSSGAPPPS GGGGGGGSGG GGSGGGGSAE SKYGPPCPPC PAPEFEGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV EWESNGQPEN NYKTTPPVLD SDGSFFLYSR LTVDKSRWQE GNVFSCSVMH EALHNHYTQK SLSLSLGGGG SSGAHPIPDS SPLLQFGGQV RQRYLYTDDA CQTEAHLEIR EDGTVGGAAD QSPESLLQLK ALKPGVIQIL GVKTSRFLCQ RPDGALYGSL HFDPEACSFR ELLEDGYNV YQSEAHGLPL HLPGCKSPHR DPAPRGPARF LPLPGLPPAP PEPPGILAPQ PDVGSSDPL SMVGSQGRSP SYAS |
| 29 | GLP1(7-36) insG, A8G, V16L, S18I, Y19Q, G22E, Q23E, A25V, K26R, E27L, A30E, V33L, K34A, 35I, R36G, insPSSGAPPPS_[19GS]_IgG4 Fc variant [7GS]_FGF21(His29-Ser209)Q55C, P147C, delP199 | GHGEGTFTSD LSIQLEEEAV RLFIEWLLAT GPSSGAPPPS GGGGGGGSGG GGSGGGGSAE SKYGPPCPPC PAPEFEGGPS VFLFPPKPKD TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV EWESNGQPEN NYKTTPPVLD SDGSFFLYSR LTVDKSRWQE GNVFSCSVMH EALHNHYTQK SLSLSLGGGG SSGAHPIPDS SPLLQFGGQV RQRYLYTDDA CQTEAHLEIR EDGTVGGAAD QSPESLLQLK ALKPGVIQIL GVKTSRFLCQ RPDGALYGSL HFDPEACSFR ELLEDGYNV YQSEAHGLPL HLCGNKSPHR DPAPRGPARF LPLPGLPPAP PEPPGILAPQ PPDVGSSDPL SMVGSQGRSP SYAS |
| 30 | GLP1(7-36) A8G, V16L, S18K, Y19Q, E21D, G22E, Q23E, A25V, K26O, E27L, A30E, V33L, K34A, A35T, R36G, insPSSGEPPPS_[19GS] | HGEGTFTSDL SKQLEEEAVQ LFIEWLLATG PSSGEPPPES GGGGGGGSGG GGSGGGGSAE SKYGPPCPPC PAPEFEGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV EWESNGQPEN NYKTTPPVLD SDGSFFLYSR LTVDKSRWQE GNVFSCSVMH EALHNHYTQK SLSLSLGGGG SSGAHPIPDS SPLLQFGGQV RQRYLYTDDA CQTEAHLEIR EDGTVGGAAD QSPESLLQLK ALKPGVIQIL GVKTSRFLCQ RPDGALYGSL HFDPEACSFR ELLEDGYNV YQSEAHGLPL HLPGCKSPHR DPAPRGPARF LPLPGLPPAP PEPPGILAPQ PPDVGSSDPL SMVYPSQGRS PSYAS |

TABLE 5-continued

List of Sequences.

| SEQ ID NO | Description | Sequence |
|---|---|---|
| | IgG4 Fc_variant [7GS]_FGF21(His29-Ser209)Q55C, N149C, G198Y | |
| 31 | GLP1(7-36) A8G, V16L, S18K, Y19Q, L20M, E21D, G22E, Q23E, A25V, K26R, E27L, A30E, V33K, K34N, R36G [19GS]_IgG4 Fc_variant [7GS]_FGF21(His29-Ser209)Q55C, N149C, G198Y | HGEGTFTSDL SKQMEEEAVR LFIEWLKNGG GGGGGGGSGG GGSGGGGSAE SKYGPPCPPC PAPEFEGGPS VFLPPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV EWESNGQPEN NYKTTPPVLD SDGSFFLYSR LTVDKSRWQE GNVFSCSVMH EALHNHYTQK SLSLSLGGGG SGSAHPIPDS SPLLQFGGQV RQRYLYTDDA CQTEAHLEIR EDGTVGGAAD QSPESLLQLK ALKPGVIQIL GVKTSRFLCQ RPDGALYGSL HFDPEACSFR ELLLEDGYNV YQSEAHGLPL HLPGCKSPHR DPAPRGPARF LPLPGLPPAP PEPPGILAPQ PPDVGSSDPL SMVYPSQGRS PSYAS |
| 32 | GLP1(7-36) A8G, V16L, S18K, Y19Q, G22E, Q23E, A25V, K26Q, E27L, A30E, V33L, K34A, G35T, R36G [19GS]_IgG4 Fc_variant [7GS]_FGF21(His29-Ser209)Q55C, N149C, G198Y | HGEGTFTSDL SKQLEEEAVQ LFIEWLLATG GGGGGGGSGG GGSGGGGSAE SKYGPPCPPC PAPEFEGGPS VFLPPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV EWESNGQPEN NYKTTPPVLD SDGSFFLYSR LTVDKSRWQEG NVFSCSVMH EALHNHYTQK SLSLSLGGGG SGSAHPIPDS SPLLQFGGQV RQRYLYTDDA CQTEAHLEIR EDGTVGGAAD QSPESLLQLK ALKPGVIQIL GVKTSRFLCQ RPDGALYGSL HFDPEACSFR ELLLEDGYNV YQSEAHGLPL HLPGCKSPHR DPAPRGPARF LPLPGLPPAP PEPPGILAPQ PPDVGSSDPL SMVYPSQGRS PSYAS |
| 33 | GLP1(7-36) A8G, V16L, S18K, Y19Q, G22E, Q23E, A25V, K26Q, E27L, A30E, V33L, K34A, G35T, R36G, insPSSGEPPPE [19GS]_IgG4 Fc_variant [7GS]_FGF21(His29-Ser209)Q55C, N149C, G198Y | HGEGTFTSDL SKQLEEEAVQ LFIEWLLATG PSSGEPPPEG GGGGGGGSGG GGSGGGGSAE SKYGPPCPPC PAPEFEGGPSV FLPPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVE WESNGQPENN YKTTPPVLDS DGSFFLYSRL TVDKSRWQEG NVFSCSVMHE ALHNHYTQKS LSLSLGGGGS GSAHPIPDSS PLLQFGGQVR QRYLYTDDAC QTEAHLEIRE DGTVGGAADQ SPESLLQLKA LKPGVIQILG VKTSRFLCQR PDGALYGSLH FDPEACSFRE LLLEDGYNVY QSEAHGLPLH LPGCKSPHRD PAPRGPARFL PLPGLPPAPP EPPGILAPQP PDVGSSDPLS MVYPSQGRSP SYAS |
| 34 | GLP1(7-36) insG, A8G, V16L, Y19Q, G22E, A24R, A25V, Q23E, K26Q, A30E, | GHGEGTFTSD LSKQLEEERV QEFIEMLVKG RPSSGAPPPS GGGGGGGSGG GGSGGGGSAE SKYGPPCPPC PAPEFEGGPS TLMISRTPEV TCVVVDVSQE DPEVQFNWV DGVEVHNAKT KPREEQFNST YRVVSVLTVL HQDWLNGKEY VFLPPPKPKD KCKVSNKGLP SSIEKTISKA LTVDKSRWQE GNVFSCSVMH EALHNHYTQK KGQPREPQVY TLPPSQEEMT KNQVSLTCLV EWESNGQPEN NYKTTPPVLD SDGSFFLYSR SPLLQFGGQV RQRYLYTDDA SLSLSLGGGG SGSAHPIPDS CQTEAHLEIR EDGTVGGAAD QSPESLLQLK ALKPGVIQIL GVKTSRFLCQ RPDGALYGSL HFDPEACSFR ELLLEDGYNV |

TABLE 5-continued

List of Sequences.

| SEQ ID NO | Description | Sequence |
|---|---|---|
|  | insPSSGAPPPS_[19GS]_IgG4 Fc_variant [7GS]_FGF21(His29-Ser209)Q55C, N149C, delP199 | YQSEAHGLPL HLPGCKSPHR DPAPRGPARF LPLPGLPPAP PEPPGILAPQ PPDVGSSDPL SMVGSQGRSP SYAS |
| 35 | GLP1(7-36) A8G, V16L, S18K, Y19Q, G22E, Q23E, A25V, K26Q, E27L, A30E, V33E, K34A, G35T, R36G, insPSSGAPPPS_[19GS]_IgG4 Fc_variant [7GS]_FGF21(His29-Ser209)Q55C, N149C, delP199 | HGEGTFTSDL SKQLEEEAVQ LFIEWLEATG PSSGAPPPSG GGGGGSGGG GSGGGGSAES KYGPPCPPCP APEFEGGPSV FLPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGGGGS GSAHPIPDSS PLLQFGGQVR QRYLYTDDAC QTEAHLEIRE DGTVGGAADQ SPESLLQLKA LKPGVIQILG VKTSRFLCQR PDGALYGSLH FDPEACSFRE LLLEDGYNVY QSEAHGLPLH LPGCKSPHRD PAPRGPARFL PLPGLPPAPP EPPGILAPQP PDVGSSDPLS MVGSQGRSPS YAS |
| 36 | GLP1(7-36) insG, A8G, V16L, S18I, Y19Q, G22E, Q23E, A25V, K26R, E27L, A30E, V33L, K34A, R36G, insPKKQRLS_[19GS]_IgG4 Fc_variant [7GS]_FGF21(His29-Ser209)Q55C, N149C, delP199 | GHGEGTFTSD LSIQLEEEAV RLFIEWLLAG GPKKQRLSGG GGGGGSGGGG SGGGGSAESK YGPPCPPCPA PEFEGGPSVF LPPKPKDTL MISRTPEVTC VVVDVSQEDP EVQFNWYVDG VEVHNAKTKP REEQFNSTYR VVSVLTVLHQ DWLNGKEYKC KVSNKGLPSS IEKTISKAKG QPREPQVYTL PPSQEEMTKN QVSLTCLVKG FYPSDIAVEW ESNGQPENNY KTTPPVLDSD GSFFLYSRLT VDKSRWQEGN VFSCSVMHEA LHNHYTQKSL SLSLGGGGSG SAHPIPDSSP LLQFGGQVRQ RYLYTDDACQ TEAHLEIRED GTVGGAADQS PESLLQLKAL KPGVIQILGV KTSRFLCQRP DGALYGSLHF DPEACSFREL LLEDGYNVYQ SEAHGLPLHL PGCKSPHRDP APRGPARFLP LPGLPPAPPE PPGILAPQPP DVGSSDPLSM VGSQGRSPSY AS |

TABLE 5-continued

List of Sequences.

| SEQ ID NO | Description | Sequence |
|---|---|---|
| 37 | GLP-1 RA, general sequence | HGEGTFTSDX SXQXXEEXVX XFIEWLXXXX |
| 38 | C-terminal peptide extension I | PSSGAPPPS |
| 39 | C-terminal peptide extension II | PVSGAPPPS |
| 40 | C-terminal peptide extension III | PSSGEPPPES |
| 41 | C-terminal peptide extension IV | PSSGEPPPE |
| 42 | C-terminal peptide extension V | PKKQRLS |
| 43 | C-terminal peptide extension VI | PKKIRYS |

The invention claimed is:

1. A combination comprising a fibroblast growth factor 21 (FGF21) compound and a glucagon-like peptide-1 receptor (GLP-1R) agonist,
   wherein the FGF21 compound has an FGF21 activity which is the same or substantially the same as the FGF21 activity of native FGF21, and
   wherein the GLP-1R agonist has a GLP-1R agonistic activity which is 9- to 531-fold reduced as compared to the GLP-1R agonistic activity of native GLP-1(7-36), and wherein the GLP-1R agonist comprises or consists of the amino acid sequence H-G-E-G-T-F-T-S-D-$X_{10}$-S-$X_{12}$-Q-$X_{14}$-$X_{15}$-E-E-$X_{18}$-V-$X_{20}$-$X_{21}$-F-I-E-W-L-$X_{27}$-$X_{28}$-$X_{29}$-$X_{30}$ (SEQ ID NO: 37), wherein $X_{10}$ is L or K;
$X_{12}$ is K or I;
$X_{14}$ is L;
$X_{15}$ is E or D;
$X_{15}$ is A or R;
$X_{20}$ is R or Q;
$X_{21}$ is L or E;
$X_{27}$ is L, E, K or V;

$X_{28}$ is A;
$X_{29}$ is T or G; and
$X_{30}$ is G or R.

2. The combination according to claim 1, wherein the GLP-1R agonist has a GLP-1R agonistic activity which is 9- to 482-fold or 9- to 319-fold or 9- to 121-fold reduced as compared to the GLP-1R agonistic activity of native GLP-1(7-36).

3. The combination according to claim 1, wherein the GLP-1R agonist has a GLP-1R agonistic activity which is 18- to 501-fold or 18- to 469-fold or 18- to 313-fold or 18- to 123-fold reduced as compared to the GLP-1R agonistic activity of native GLP-1(7-36).

4. The combination according to claim 1, wherein the FGF21 compound is native FGF21 or an FGF21 variant having at least 80% or at least 90% or at least 95% amino acid sequence identity to the amino acid sequence of native FGF21.

5. The combination according to claim 1, wherein the GLP-1R agonist comprises or consists of an amino acid sequence selected from the group consisting of SEQ ID NOs: 9, 10, 12, 14, 16, 17, 19 and 20.

6. The combination according to claim 1, wherein the amino acid sequence comprises at least one additional amino acid residue at its N-terminus.

7. The combination according to claim 1, wherein the amino acid sequence comprises a peptide extension consisting of up to 12, 11 or 10 amino acid residues at its C-terminus.

8. The combination according to claim 1, wherein the amino acid sequence comprises at least one additional amino acid residue at its N-terminus and a peptide extension consisting of up to 12, 11 or 10 amino acid residues at its C-terminus.

9. A method for treating a disease or disorder selected from the group consisting of obesity, being overweight, metabolic syndrome, diabetes mellitus, diabetic retinopathy, hyperglycemia, dyslipidemia, Non-Alcoholic SteatoHepatitis (NASH) and atherosclerosis, the method comprising administering the combination according to claim 1 to a subject in need thereof.

10. The method according to claim 9, wherein the diabetes mellitus is type 1 diabetes mellitus or type 2 diabetes mellitus.

11. The method according to claim 9, wherein the diabetes mellitus is type 2 diabetes mellitus.

12. A pharmaceutical composition comprising a fibroblast growth factor 21 (FGF21) compound and a glucagon-like peptide-1 receptor (GLP-1R) agonist together with a pharmaceutically acceptable carrier and/or excipient,
wherein the FGF21 compound has an FGF21 activity which is the same or substantially the same as the FGF21 activity of native FGF21, and
wherein the GLP-1R agonist has a GLP-1R agonistic activity which is 9- to 531-fold reduced as compared to the GLP-1R agonistic activity of native GLP-1(7-36), and wherein the GLP-1R agonist comprises or consists of the amino acid sequence H-G-E-G-T-F-T-S-D-$X_{10}$-S-$X_{12}$-Q-$X_{14}$-$X_{15}$-E-E-$X_{18}$-V-$X_{20}$-$X_{21}$-F-I-E-W-L-$X_{27}$-$X_{28}$-$X_{29}$-$X_{30}$ (SEQ ID NO: 37), wherein
$X_{10}$ is L or K;
$X_{12}$ is K or I;
$X_{14}$ is L;
$X_{15}$ is E or D;
$X_{18}$ is A or R;
$X_{20}$ is R or Q;
$X_{21}$ is L or E;
$X_{27}$ is L, E, K or V;
$X_{28}$ is A;
$X_{29}$ is T or G; and
$X_{30}$ is G or R.

13. The pharmaceutical composition according to claim 12, wherein the amino acid sequence comprises at least one additional amino acid residue at its N-terminus.

14. The pharmaceutical composition according to claim 12, wherein the amino acid sequence comprises a peptide extension consisting of up to 12, 11 or 10 amino acid residues at its C-terminus.

15. The pharmaceutical composition according to claim 12, wherein the amino acid sequence comprises at least one additional amino acid residue at its N-terminus and a peptide extension consisting of up to 12, 11 or 10 amino acid residues at its C-terminus.

16. A method of treating a disease or disorder selected from the group consisting of obesity, being overweight, metabolic syndrome, diabetes mellitus, diabetic retinopathy, hyperglycemia, dyslipidemia, Non-Alcoholic SteatoHepatitis (NASH) and atherosclerosis, the method comprising administering the pharmaceutical composition according to claim 12 to a subject in need thereof.

17. The method according to claim 16, wherein the diabetes mellitus is type 2 diabetes mellitus.

18. A glucagon-like peptide-1 receptor (GLP-1R) agonist having a GLP-1R agonistic activity which is 9- to 531-fold reduced as compared to the GLP-1R agonistic activity of native GLP-1(7-36), wherein the GLP-1R agonist comprises or consists of the amino acid sequence H-G-E-G-T-F-T-S-D-$X_{10}$-S-$X_{12}$-Q-$X_{14}$-$X_{15}$-E-E-$X_{18}$-V-$X_{20}$-$X_{21}$-F-I-E-W-L-$X_{27}$-$X_{28}$-$X_{29}$-$X_{30}$ (SEQ ID NO: 37), wherein
$X_{10}$ is L or K;
$X_{12}$ is K or I;
$X_{14}$ is L;
$X_{15}$ is E or D;
$X_{18}$ is A or R;
$X_{20}$ is R or Q;
$X_{21}$ is L or E;
$X_{27}$ is L, E, K or V;
$X_{28}$ is A;
$X_{29}$ is T or G; and
$X_{30}$ is G or R.

19. The GLP-1R agonist according to claim 18, comprising or consisting of an amino acid sequence selected from the group consisting of SEQ ID NOs: 9, 10, 12, 14, 16, 17, 19 and 20.

20. The GLP-1R agonist according to claim 18, wherein the amino acid sequence comprises at least one additional amino acid residue at its N-terminus.

21. The GLP-1R agonist according to claim 18, wherein the amino acid sequence comprises a peptide extension consisting of up to 12, 11 or 10 amino acid residues at its C-terminus.

22. The GLP-1R agonist according to claim 18, wherein the amino acid sequence comprises at least one additional amino acid residue at its N-terminus and a peptide extension consisting of up to 12, 11 or 10 amino acid residues at its C-terminus.

* * * * *